(12) United States Patent
Wong et al.

(10) Patent No.: US 10,342,858 B2
(45) Date of Patent: Jul. 9, 2019

(54) GLYCAN CONJUGATES AND METHODS OF USE THEREOF

(71) Applicant: Academia Sinica, Taipei (TW)

(72) Inventors: Chi-Huey Wong, Rancho Santa Fe, CA (US); Chung-Yi Wu, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 57 days.

(21) Appl. No.: 14/832,993

(22) Filed: Aug. 21, 2015

(65) Prior Publication Data

US 2016/0213763 A1    Jul. 28, 2016

Related U.S. Application Data

(60) Provisional application No. 62/107,378, filed on Jan. 24, 2015.

(51) Int. Cl.

| | |
|---|---|
| C07H 5/02 | (2006.01) |
| C07H 5/04 | (2006.01) |
| C07H 5/06 | (2006.01) |
| A61K 39/00 | (2006.01) |
| C07H 15/04 | (2006.01) |
| C07H 15/26 | (2006.01) |
| C07K 16/30 | (2006.01) |
| C07K 16/44 | (2006.01) |
| C08B 37/00 | (2006.01) |
| A61K 31/715 | (2006.01) |
| A61K 31/7028 | (2006.01) |

(52) U.S. Cl.
CPC ...... *A61K 39/0011* (2013.01); *A61K 31/7028* (2013.01); *A61K 31/715* (2013.01); *C07H 5/02* (2013.01); *C07H 5/04* (2013.01); *C07H 5/06* (2013.01); *C07H 15/04* (2013.01); *C07H 15/26* (2013.01); *C07K 16/3076* (2013.01); *C07K 16/44* (2013.01); *C08B 37/006* (2013.01); *A61K 2039/55511* (2013.01); *A61K 2039/6037* (2013.01); *A61K 2039/627* (2013.01)

(58) Field of Classification Search
CPC ...... C07D 309/02; C07D 309/08; C07H 3/06; A61K 31/7028; A61K 31/715; A61K 39/385; A61K 39/39
See application file for complete search history.

(56) References Cited

U.S. PATENT DOCUMENTS

| | | | |
|---|---|---|---|
| 3,773,919 A | 11/1973 | Boswell et al. | |
| 3,896,111 A | 7/1975 | Kupchan et al. | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,270,537 A | 6/1981 | Romaine | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| RE30,985 E | 6/1982 | Cartaya | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,376,110 A | 3/1983 | David et al. | |

(Continued)

FOREIGN PATENT DOCUMENTS

| | | |
|---|---|---|
| EP | 0404097 A2 | 12/1990 |
| EP | 0341735 B1 | 9/1992 |

(Continued)

OTHER PUBLICATIONS

Lee, H.-Y., et al., Journal of the American Chemical Society, 136: 16844-16853, Nov. 2014.*
Huang, Y.-L., et al., Proc. Natl. Acad. Sci., 110(7): 2517-2522, Feb. 2013.*
Pan, Y., et al., J. Med. Chem., 48(3): 875-883, 2005.*
Harvey, David J., "Matrix-Assisted Laser Desorption/Ionization Mass Spectrometry of Sphingo- and Glycosphingo-Lipids" Journal of Mass Spectrometry (1995) vol. 30 pp. 1311-1324 (Year: 1995).*
Kannagi et al., "Stage-specific embryonic antigens (SSEA-3 and -4) are epitopes of a unique globo-series ganglioside isolated from human teratocarcinoma cells" EMBO Journal vol. 2 No. 12 pp. 2355-2361 (Year: 1983).*

(Continued)

Primary Examiner — Eric Olson
(74) Attorney, Agent, or Firm — Duane Morris LLP

(57) ABSTRACT

The present disclosure is directed to vaccines, antibodies, and/or immunogenic conjugate compositions targeting the SSEA3/SSEA4/GloboH associated epitopes (natural and modified) which elicit antibodies and/or binding fragment production useful for modulating the globo-series glycosphingolipid synthesis. The present disclosure relates to methods and compositions which can modulate the globo-series glycosphingolipid synthesis. Particularly, the present disclosure is directed to glycoenzyme inhibitor compound and compositions and methods of use thereof that can modulate the synthesis of globo-series glycosphingolipid SSEA3/SSEA4/GloboH in the biosynthetic pathway; particularly, the glycoenzyme inhibitors target the alpha-4GalT; beta-4GalNAcT-I; or beta-3GalT-V enzymes in the globo-series synthetic pathway. Moreover, the present disclosure is also directed to the method of using the compositions described herein for the treatment or detection of hyperproliferative diseases and/or conditions.

43 Claims, 7 Drawing Sheets

(56) References Cited

U.S. PATENT DOCUMENTS

| | | |
|---|---|---|
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 * | 12/2010 | Danishefsky ........ A61K 31/715 424/193.1 |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |

(56) References Cited

U.S. PATENT DOCUMENTS

| | | | |
|---|---|---|---|
| 8,101,179 B2 | 1/2012 | Numazaki et al. | |
| 8,268,969 B2 * | 9/2012 | Wong et al. | 530/387.1 |
| 8,383,554 B2 | 2/2013 | Wong et al. | |
| 8,507,660 B2 | 8/2013 | Wong et al. | |
| 8,680,020 B2 | 3/2014 | Wong et al. | |
| 8,715,963 B2 | 5/2014 | Sethuraman | |
| 8,716,465 B2 | 5/2014 | Rossi et al. | |
| 8,802,438 B2 | 8/2014 | Rossi et al. | |
| 8,815,941 B2 | 8/2014 | Withers | |
| 8,883,506 B2 | 11/2014 | Rossi et al. | |
| 8,906,832 B2 | 12/2014 | Wong et al. | |
| 8,907,111 B2 | 12/2014 | Withers | |
| 9,187,552 B2 | 11/2015 | Stadheim | |
| 9,221,859 B2 | 12/2015 | Withers | |
| 9,382,284 B2 | 7/2016 | Withers | |
| 9,434,786 B2 | 9/2016 | Wang | |
| 9,759,726 B2 | 9/2017 | Wong et al. | |
| 9,803,177 B2 | 10/2017 | Rossi et al. | |
| 9,914,956 B2 | 3/2018 | Wong et al. | |
| 10,005,847 B2 | 6/2018 | Wong | |
| 10,023,892 B2 | 7/2018 | Wong | |
| 10,118,969 B2 | 11/2018 | Wong | |
| 2002/0025313 A1 | 2/2002 | Micklus et al. | |
| 2002/0038086 A1 | 3/2002 | Hynynen et al. | |
| 2002/0065259 A1 | 5/2002 | Schatzberg et al. | |
| 2003/0073713 A1 | 4/2003 | Schoenhard | |
| 2003/0083299 A1 | 5/2003 | Ferguson | |
| 2003/0104402 A1 | 6/2003 | Zauderer et al. | |
| 2003/0118592 A1 | 6/2003 | Ledbetter et al. | |
| 2003/0129186 A1 | 7/2003 | Beliveau et al. | |
| 2003/0162695 A1 | 8/2003 | Schatzberg et al. | |
| 2003/0175884 A1 | 9/2003 | Umana et al. | |
| 2003/0219433 A1 | 11/2003 | Hansen et al. | |
| 2004/0072290 A1 | 4/2004 | Umana et al. | |
| 2004/0086423 A1 | 5/2004 | Wohlstadter | |
| 2004/0131692 A1 | 7/2004 | Kreuter et al. | |
| 2004/0137557 A1 | 7/2004 | DeFrees et al. | |
| 2004/0204354 A1 | 10/2004 | Nelson et al. | |
| 2004/0259142 A1 | 12/2004 | Chai et al. | |
| 2005/0085413 A1 | 4/2005 | Jin et al. | |
| 2005/0089473 A1 | 4/2005 | Black et al. | |
| 2005/0106108 A1 | 5/2005 | Hansen et al. | |
| 2005/0123546 A1 | 6/2005 | Umana et al. | |
| 2005/0124533 A1 | 6/2005 | Schatzberg et al. | |
| 2005/0221337 A1 | 10/2005 | Seeberger et al. | |
| 2005/0221397 A1 | 10/2005 | Saito | |
| 2005/0255491 A1 | 11/2005 | Lee | |
| 2006/0019256 A1 | 1/2006 | Clarke et al. | |
| 2006/0073122 A1 | 4/2006 | Koezuka et al. | |
| 2006/0073161 A1 | 4/2006 | Breton | |
| 2006/0211856 A1 | 9/2006 | Tsuji et al. | |
| 2006/0286140 A1 | 12/2006 | Wickstrom et al. | |
| 2006/0286637 A1 | 12/2006 | Hamilton | |
| 2007/0059769 A1 | 3/2007 | Blixt et al. | |
| 2007/0065949 A1 | 3/2007 | Hutchens | |
| 2007/0207090 A1 | 9/2007 | Giudice | |
| 2007/0213278 A1 | 9/2007 | Wong et al. | |
| 2007/0213297 A1 | 9/2007 | Wong et al. | |
| 2007/0219351 A1 | 9/2007 | Fiume et al. | |
| 2007/0224189 A1 | 9/2007 | Lazar et al. | |
| 2007/0238871 A1 | 10/2007 | Tsuji et al. | |
| 2008/0070324 A1 | 3/2008 | Floyd | |
| 2008/0145838 A1 | 6/2008 | Suda et al. | |
| 2008/0220988 A1 | 9/2008 | Zhou | |
| 2008/0260774 A1 | 10/2008 | Wong et al. | |
| 2009/0035179 A1 | 2/2009 | Rakow et al. | |
| 2009/0081255 A1 | 3/2009 | Bublot et al. | |
| 2009/0123439 A1 | 5/2009 | Yun et al. | |
| 2009/0285837 A1 | 11/2009 | Kao et al. | |
| 2009/0298797 A1 | 12/2009 | Zheng et al. | |
| 2009/0317837 A1 | 12/2009 | Wong et al. | |
| 2010/0009339 A1 | 1/2010 | Bovin et al. | |
| 2010/0022026 A1 | 1/2010 | Rump et al. | |
| 2010/0047827 A1 | 2/2010 | Laine et al. | |
| 2010/0047828 A1 | 2/2010 | Sorenson et al. | |
| 2010/0068806 A1 | 3/2010 | Laine et al. | |
| 2010/0112195 A1 | 5/2010 | Kodas et al. | |
| 2010/0113397 A1 | 5/2010 | Wong et al. | |
| 2010/0136009 A1 | 6/2010 | Papkoff et al. | |
| 2010/0136042 A1 | 6/2010 | Wong et al. | |
| 2010/0173323 A1 | 7/2010 | Strome | |
| 2011/0086408 A1 | 4/2011 | Powers | |
| 2011/0104188 A1 | 5/2011 | Tashiro et al. | |
| 2011/0124116 A1 | 5/2011 | Wohlstadter et al. | |
| 2011/0137570 A1 | 6/2011 | Lapadula et al. | |
| 2011/0237459 A1 | 9/2011 | Nova et al. | |
| 2011/0263828 A1 | 10/2011 | Wong et al. | |
| 2012/0046346 A1 | 2/2012 | Rossi et al. | |
| 2012/0171201 A1 | 7/2012 | Sapra | |
| 2012/0178705 A1 | 7/2012 | Liang et al. | |
| 2012/0178802 A1 | 7/2012 | Withers et al. | |
| 2012/0226024 A1 | 9/2012 | Wang et al. | |
| 2012/0294859 A1 | 11/2012 | Goletz et al. | |
| 2012/0322864 A1 | 12/2012 | Rossi et al. | |
| 2012/0322865 A1 | 12/2012 | Rossi et al. | |
| 2012/0328646 A1 | 12/2012 | Wong et al. | |
| 2013/0189258 A1 | 7/2013 | Rother et al. | |
| 2013/0196356 A1 | 8/2013 | Jackson et al. | |
| 2013/0230886 A1 | 9/2013 | Votsmeier et al. | |
| 2013/0337018 A1 | 12/2013 | Fox | |
| 2014/0051127 A1 | 2/2014 | Wong et al. | |
| 2014/0086916 A1 | 3/2014 | Zha | |
| 2014/0127241 A1 | 5/2014 | Leuschner et al. | |
| 2014/0178365 A1 | 6/2014 | Ghaderi et al. | |
| 2014/0227290 A1 | 8/2014 | Sethuraman | |
| 2014/0302028 A1 | 10/2014 | Zha | |
| 2014/0308746 A1 | 10/2014 | Rossi et al. | |
| 2015/0087814 A1 | 3/2015 | Wang | |
| 2015/0160217 A1 | 6/2015 | Wong et al. | |
| 2015/0225766 A1 | 8/2015 | Wong et al. | |
| 2015/0309041 A1 | 10/2015 | Wong et al. | |
| 2015/0344544 A1 | 12/2015 | Wong et al. | |
| 2015/0344551 A1 | 12/2015 | Wong et al. | |
| 2015/0344559 A1 | 12/2015 | Wong et al. | |
| 2015/0344585 A1 | 12/2015 | Wong et al. | |
| 2015/0344587 A1 | 12/2015 | Wong et al. | |
| 2016/0102151 A1 | 4/2016 | Wong et al. | |
| 2016/0215061 A1 | 7/2016 | Shaeen | |
| 2016/0274121 A1 | 9/2016 | Wong et al. | |
| 2016/0280794 A1 | 9/2016 | Wong et al. | |
| 2016/0289340 A1 | 10/2016 | Wong et al. | |
| 2017/0275389 A1 * | 9/2017 | Wong | C08B 37/0024 |
| 2017/0283878 A1 | 10/2017 | Wong et al. | |
| 2017/0362330 A1 | 12/2017 | Liu | |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 | 12/1993 |
| JP | 11-343295 A | 12/1999 |
| JP | 2005-06008 | 5/2000 |
| JP | 2002-371087 A | 12/2002 |
| JP | 2008-025989 A | 2/2008 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |

(56) References Cited

FOREIGN PATENT DOCUMENTS

| | | |
|---|---|---|
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO2010/029302 A2 | 3/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO2013/106937 A1 | 7/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2014/031762 A1 | 2/2017 |

OTHER PUBLICATIONS

Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.

Frank, Natasha et al., The Therapeutic Promise of the Cancer Stem Cell Concept, Journal of Clinical Investigation, 120(1) 41-50, Jan. 2010.

Hsu, Nien-Yeen et al., Desorption Ionization of Biomolecules on Metals, Anal. Chem., 80, 5203-5210, 2008.

Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.

Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Merck, MAB4304, Anti-Stage-Specific Embryonic Antigen-4 Antibody, Clone MC-813-70, 4 Pages, 2017.

Moal, E. LE et al., Enhanced Fluorescence Cell Imaging with Metal-Coated Slides, Biophysical Journal, vol. 92, 2150-2161, Mar. 2007.

Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.

Shevinsky, LH et al., Monoclonal Antibody to Murine Embryos Defines a Stage-Specific Embryonic Antigen Expressed on Mouse Embryos and Human Teratocarinoma Cells., Cell vol. 30, Issue 3, Oct. 1982, pp. 697-705.

Zhang, Hai-Long et al., A Novel Combined Conjugate Vaccine: Enhanced Immunogenicity of bFGF with CRM197 as a Carrier Protein, Molecular Medicine Reports, 4, 857-863, 2011.

U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 30, 2016, Wong et al.

Abbas et al., "Functional diversity of helper T lymphocytes," *Nature*, Oct. 31, 1996, 383(6603):787-793.

Abrahmsén et al, "Analysis of signals for secretion in the staphylococcal protein A gene," *EMBO J.*, Dec. 30, 1985, 4(13B):3901-3906.

Achtman, M., Epidemic Spread and Antigenic Variability of Neisseria Meningitidis, Trends Microbial 1995, 3, 186-192.

Adam et al., "Proteomic profiling of mechanistically distinct enzyme classes using a common chemotype," *Nat. Biotechnol.*, Aug. 2002, 20(8):805-809.

Agard, N. et al., A Strain-Promoted [3+2]Azide-Alkyne Cycloaddition for Covalent Modification of Biomolecules in Living Systems, J. Am. Chem. Soc. 2004, 126, 15046-15047.

Ahmadi, T. S. et al., Shape-Controlled Synthesis of Colloidal Platinum Nanoparticles, Science, 272, 1924 (1996).

Ahmed et al.,Structural Characterization of Anti-Inflammatory Immunoglobulin G Fc Proteins, K Mol Biol (2014) 426, 3166-3179.

Altevogt, Peter et al., Different Patterns of Lectin Binding and Cell Surface Sialylation Detected on Related High- and Low-Metastatic Tumor Lines, Cancer Res. 43, 5138-5144, 1983.

Altschul SF et al., "Basic local alignment search tool", *J Mol Biol.* Oct. 5, 1990;215(3):403-10.

Altschul SF, et al., "Gapped BLAST and PSI-BLAST: a new generation of protein database search programs", *Nucleic Acids Res.* Sep. 1, 1997;25(17):3389-402.

Amin, M. N. et al. Synthetic glycopeptides reveal the glycan specificity of HIV-neutralizing antibodies. Nat. Chem. Biol. 9, 521-526, (2013).

Anderson et al., "Stimulation of Natural Killer T Cells by Glycolipids", *Molecules*, May 2013, 18(12), 15662-15688.

(56) References Cited

OTHER PUBLICATIONS

Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," *Chem. Rev.*, Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1$^+$ CD4$^+$ CD8$^-$ thymocytes with specific lymphokine secretion," *Eur. J. Immunol.*, Jan. 1993, 23(1):307-310.
Arié et al., "Chaperone function of FkpA, a heat shock prolyl isomerase, in the periplasm of *Escherichia coli*," *Mol. Microbiol.*, Jan. 2001, 39(1):199-210.
Aspeslagh et al., "Galactose-modified iNKT cell agonists stabilized by an induced fit of CD1d prevent tumour metastasis," *EMBO J.*, Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bachmann *Cellular and Molecular Biology, vol. 2, Chapter 72: Derivations and Genotypes of Some Mutant Derivatives of Escherichia coli K-12*, Neidhardt et al., eds., 1987, pp. 1190-1219, American Society for Microbiology, Washington, D.C.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Baldwin et al., "Monoclonal antibodies in cancer treatment," *Lancet*, Mar. 15, 1986, 327(8481):603-605.
Banchereau et al., "Dendritic cells and the control of immunity," *Nature*, Mar. 19, 1998, 392(6673):245-252.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barnes et al., "Methods for growth of cultured cells in serum-free medium," *Anal. Biochem.*, Mar. 1, 1980, 102(2):255-270.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.
Baskin, J.M.; Amacher, S. L.; Bertozzi, C.R."In vivo imaging of membraneassociated glycans in developing zebrafish." Science 2008, 320, 664-667.
Bass et al., "Hormone phage: an enrichment method for variant proteins with altered binding properties," *Proteins*, 1990, 8(4):309-314.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beck A., "Biosimilar, biobetter and next generation therapeutic antibodies" *MAbs*. Mar.-Apr. 2011;3(2):107-10. Epub Mar. 1, 2011.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Berra et al., "Correlation between ganglioside distribution and histological grading of human astrocytomas," *Int. J. Cancer*, Sep. 15, 1985, 36(3):363-366.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Birklé et al., "Role of tumor-associated gangliosides in cancer progression," *Biochimie*, Mar.-Apr. 2003, 85(3-4):455-463.
Blixt, O. et al. Printed covalent glycan array for ligand profiling of diverse glycan binding proteins. Proc. Natl. Acad. Sci. U.S. A. 101, 17033-17038, (2004.
Bobo et al., "Convection-enhanced delivery of macromolecules in the brain," *Proc. Natl. Acad. Sci. U.S.A.*, Mar. 15, 1994, 91(6) 2076-2080.
Boens, N. et al., "Fluorescent indicators based on BODIPY." Chem. Soc. Rev. 2012, 41, 1130-1172.
Boerner et al., "Production of antigen-specific human monoclonal antibodies from in vitro-primed human splenocytes," *J. Immunol.*, Jul. 1, 1991, 147(1):86-95.
Borg et al., "CD1d-lipid-antigen recognition by the semi-invariant NKT T-cell receptor," *Nature*, Jul. 5, 2007, 448(7149):44-49.
Bosmann et al., "Enzyme activity in invasive tumors of human breast and colon," *Proc. Natl. Acad. Sci. USA*, May 1974, 71(5):1833-1837.
Bost, Kenneth et al., Antibodies Against a Peptide Sequence Within the HIV Envelope Protein Crossreacts With Human Interleukin-2, Immunol Invest., 17: 577-586, (1988).
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Brennan et al., "Preparation of bispecific antibodies by chemical recombination of monoclonal immunoglobulin G$_1$ fragments," *Science*, Jul. 5, 1985, 229(4708):81-83.
Bricard et al., "Enrichment of human CD4$^+$ Vα24/Vβ11 invariant NKT cells in intrahepatic malignant tumors," *J. Immunol.*, Apr. 15, 2009, 182(2):5140-5151.

(56) References Cited

OTHER PUBLICATIONS

Brimble et al., "The cell surface glycosphingolipids SSEA-3 and SSEA-4 are not essential for human ESC pluripotency," Stem Cells, Jan. 2007, 25(1):54-62.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Bruchez, Marcel et al. Semiconductor Nanocrystals as Fluorescent Biological Labels, Science 281:2013-2016, 1998.
Brüggemann et al., "Designer mice: the production of human antibody repertoires in transgenic animals," Year in Immunol., 1993, 7:33-40.
Buchini et al., "Towards a new generation of specific Trypanosoma cruzi trans-sialidase inhibitors," Angew. Chem. Int. Ed. Engl., 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Capel PJ et al., "Heterogeneity of human IgG Fc receptors" Immunomethods. Feb. 1994;4(1):25-34.
Carlsson, Jan et al., Protein Thiolation and Reversible Protein-Protein Conjugation, Biochem J 173: 723-737 (1978).
Carter et al., "High level Escherichia coli expression and production of a bivalent humanized antibody fragment," Nature Biotechnology, Feb. 1992, 10(2):163-167.
Carter et al., "Humanization of an anti-p185$^{HER2}$ antibody for human cancer therapy," Proc. Natl. Acad. Sci. U.S.A., May 15, 1992, 89(10):4285-4289.
Carter PJ. "Potent antibody therapeutics by design" Nat Rev Immunol. May 2006;6(5):343-357.
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" MMWR, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," Proc. Natl. Acad. Sci. USA, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari Ravi et al., Immunoconjugates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.

Chen et al., "Chaperone activity of DsbC," J. Bio. Chem., Jul. 9. 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Cheng, Peter et al., Oseltamivir-and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Canonical structures for the hypervariable regions of immunoglobulins," J. Mol. Biol., Aug. 20, 1987, 196(4):901-917.
Chothia et al., "Domain association in immunoglobulin molecules. The packing of variable domains," J. Mol. Biol., Dec. 5, 1985, 186(3):651-663.
Clackson et al., "Making antibody fragments using phage display libraries," Nature, Aug. 15, 1991, 352(6336):624-628.
Clark EA et al., "Structure, function, and genetics of human B cell-associated surface molecules" Adv Cancer Res. 1989;52:81-149.
Clynes R, et al., "Fc receptors are required in passive and active immunity to melanoma" Proc Natl Acad Sci U S A. Jan. 20, 1998;95(2):652-6.
Codelli, J. A. et al., Second-Generation Difluorinated Cyclooctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2. 6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.

(56) References Cited

OTHER PUBLICATIONS

Cunningham et al., "High-resolution epitope mapping of hGH-receptor interactions by alanine-scanning mutagenesis," *Science*, Jun. 2, 1989, 244(4908):1081-1085.
Cyranoski, Threat of Pandemic Brings Flu Drug Back to Life, Nat. Med. Sep. 2005, 11(9): 909.
Daëron, "Fc receptor biology," *Annu. Rev. Immunol.*, 1997, 15:203-234.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine αβT cells expressing invariant TCR alpha-chains," *J. Immunol.*, Jun. 15, 1997, 158(12):5603-5611.
De Almeida et al., "Thiacycloalkynes for copper-free click chemistry," *Angew. Chem. Int. Ed. Engl.*, Mar. 5, 2012, 51(10):2443-2447.
Debets, M. F. et al., Bioconjugation with Strained Alkenes and Alkynes, Acc. Chem. Res. 2011, 44, 805-815.
De Haas et al., "Fcγ receptors of phagocytes," *J. Lab. Clin. Med.*, Oct. 1995, 126(4):330-341.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant Vα24-JαQ/Vβ11 T cell receptor is expressed in all individuals by clonally expanded CD4−8$^{31}$ T cells," *J. Exp. Med.*, Sep. 1, 1994, 180(3):1171-1176.
Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "α-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," *J. Exp. Med.*, Jun. 16, 2003, 197(12):1667-1676.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Donimerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Durrant et al., "Immunology in the clinic review series; focus on cancer: glycolipids as targets for tumour immunotherapy," *Clin. Exp. Immunol.*, Feb. 2012, 167(2):206-215.
Eberl et al., "Selective bystander proliferation of memory CD4$^+$ and CD8$^+$ T cells upon NK T or T cell activation," *J. Immunol.*, Oct. 15, 2000, 165(8):4305-4311.
Eberl et al., "Selective induction of NK cell proliferation and cytotoxicity by activated NKT cells," *Eur. J. Immunol.*, Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)],"*Angew. Chem. Int. Ed Engl.*, Jun. 1989, 28(6):716-734.
European Search Report issued in connection with corresponding European Patent Application No. 15181446.4, dated Dec. 7, 2015, 10 pages.
Evans, Michael et al., "Mechanism-based profiling of enzyme families," *Chem. Rev.*, Aug. 2006, 106(8):3279-3301.
Evans, "The rise of azide-alkyne 1,3-dipolar 'click' cycloaddition and its application to polymer science and surface modification," *Australian J. Chem.*, Jun. 2007, 60(6):384-395.
Extended European Search Report dated Jan. 5, 2016 in European Patent Application No. 13830785.5, in 10 pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from *Streptococcus pneumoniae*, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fishwild et al., "High-avidity human IgGκ monoclonal antibodies from a novel strain of minilocus transgenic mice," *Nature Biotechnol.*, Jul. 1996, 14(7):845-851.

(56) References Cited

OTHER PUBLICATIONS

Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fujita M et al., "A novel disaccharide substrate having 1,2-oxazoline moiety for detection of transglycosylating activity of endoglycosidases" Biochim Biophys Acta. Sep. 3, 2001;1528(1):9-14.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Galfrè et al., "Preparation of monoclonal antibodies: strategies and procedures," *Methods Enzymol.*, 1981, 73(Pt B):3-46.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Gazzano-Santoro et al., "A non-radioactive complement-dependent cytotoxicity assay for anti-CD20 nonclonal antibody," *J. Immunol. Methods*, Mar. 28, 1997, 202(2):163-171.
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [*Streptomyces plicatus*]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP 212855.1, "Putative exported alpha-L-fucosidase protein [Bacteroides fragilis NCTC 9343]," Mar. 2, 2014.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Gill et al., "Direct brain infusion of glial cell line-derived neurotrophic factor in Parkinson disease," *Nature Med.*, May 2003, 9(5):589-595 and Addendum from Apr. 2006, 12(4):479.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goding, *Monoclonal Antibodies: Principles and Practice* $2^{nd}$ ed., *Chapter 3: Production of Monoclonal Antibodies*, 1986, pp. 59-103, Academic Press, London.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J.*, Mar. 2013, 41(3):656-663.
Govorkova et al, Combination chemotherapy for influenza. Viruses. Aug. 2010;2(8):1510-29.
Graham et al., "Characteristics of a human cell line transformed by DNA from human adenovirus type 5," *J. Gen. Virol.*, Jul. 1977, 36(1):59-72.
Graham, Duncan et al., Surface-Enhanced Resonance Raman Scattering as a Novel Method of DNA Discrimination, Angew. Chem., 2000, 112(6), 1103-1105.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Grandjean, C. et al., On the Preparation of Carbohydrate-Protein Conjugates Using the Traceless Staudinger Ligation, J Org Chem 2005, 70, 7123-7132.
Green, "Targeting targeted therapy," *N. Engl J. Med.*, May 20, 2004, 350(21):2191-2193.
Greenbaum et al., "Chemical approaches for functionally probing the proteome," *Mol. Cell. Proteomics*, 2002, 1:60-68.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.

(56) References Cited

OTHER PUBLICATIONS

Gulland, Fire Cases of Spread of Oseltamivir Resistant Swine Flu Between Patients are Reported in Wales, BMJ, Nov. 23, 2009:339:b4975.
Guss et al., "Structure of the IgG-binding regions of streptococcal protein G," EMBO J., Jul. 1986, 5(7):1567-1575.
Guyer et al., "Immunoglobulin binding by mouse intestinal epithelial cell receptors," J. Immunol., Aug. 1976, 117(2):587-593.
Ha, Ya et al., X-Ray Structures of H5 Avian and I-19 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," J. Immuol., May 1, 1995, 154(9):4322-4332.
Hakomori et al., "Glycosphingolipid antigens and cancer therapy," Chem. Biol., Feb. 1997, 4(2):97-104.
Hakomori, "Glycosylation defining cancer malignancy: new wine in an old bottle," Proc. Natl. Acad. Sci. U.S.A., Aug. 6, 2002, 99(16):10231-10233.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hara et al., "Overproduction of penicillin-binding protein 7 suppresses thermosensitive growth defect at low osmolarity due to an spr mutation of *Escherichia coli*," Microbial Drug Resistance, Spring 1996, 2(1):63-72.
Harris, "Production of humanized monoclonal antibodies for in vivo imaging and therapy," Biochem. Soc. Transactions, Nov. 1995, 23(4):1035-1038.
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Hawkins et al., "Selection of phage antibodies by binding affinity. Mimicking affinity maturation," J. Mol. Biol., 1992, 226(3):889-896.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Heiner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Heyman, "Complement and Fc-receptors in regulation of the antibody response," Immunol. Lett., Dec. 1996, 54(2-3):195-199.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hogrefe et al., "A bacteriophage lambda vector for the cloning and expression of immunoglobulin Fab fragments on the surface of filamentous phage," Gene, Jun. 15, 1993, 128(1):119-126.
Holliger et al., "'Diabodies': small bivalent and bispecific antibody fragments," Proc. Natl. Acad. Sci. U.S.A., Jul. 15, 1993, 90(14):6444-6448.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Honegger et al., "Yet another numbering scheme for immunoglobulin variable domains: an automatic modeling and analysis tool," J. Mol. Biol., Jun. 8, 2001, 309:657-670.
Hoogenboom et al., "By-passing immunisation: Human antibodies from synthetic repertoires of germline $V_H$ gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," Immunol. Today, Jun. 1992, 13(6):198-200.
Hsu et al., "Alkynyl sugar analogs for the labeling and visualization of glycoconjugates in cells," Proc. Natl. Acad. Sci. USA, Feb. 20, 2007, 104(8), 2614-2619.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Hung et al., "Investigation of SSEA-4 binding protein in breast cancer cells," J. Am. Chem. Soc., Apr. 24, 2013, 135(16):5934-5937.
Hurle et al., "Protein engineering techniques for antibody humanization," Curr. Opin. Biotechnol., Aug. 1994, 5(4):428-433.
Immunogenicity, Wikipedia p. 1-3. Downloaded on Aug. 16, 2016 from https://en.wikipedia.org/wiki/Immunogenicity. (2016).
Inouye et al., "Single-step purification of $F(ab')_{2u}$ fragments of mouse monoclonal antibodies (immunoglobulins M) by hydrophobic interaction high-performance liquid chromatography using TSKgel Ether-5PW," J. Biochem. Biophys. Methods, Feb. 1993, 26(1):27-39.
International Search Report and Written Opinion issued for International application No. PCT/US2015/011748, dated Aug. 21, 2015, 17 pages.
International Search Report and Written Opinion issued for International application No. PCT/US2015/032737, dated Oct. 1, 2015, 13 pages.
International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.
International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.

(56) References Cited

OTHER PUBLICATIONS

International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihero et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," *J. Immunol.*, Apr. 1, 1995, 154(7):3310-3319.
Jacobs et al., "Metabolic labeling of glycoproteins with chemical tags through unnatural sialic acid biosynthesis," *Methods Enzymol.*, 2000, 327:260-275.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jenkins N, Curling EM., "Glycosylation of recombinant proteins: problems and prospects", *Enzyme Microb Technol.* May 1994;16(5):354-64.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.

Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Kam et al., "Carbon nanotubes as multifunctional biological transporters and near-infrared agents for selective cancer cell destruction," *Proc. Nati. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kawakami et al., "Critical role of Vα14+ natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of $v_\alpha 14$ NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karlin S. et al., "Methods for assessing the statistical significance of molecular sequence features by using general scoring schemes", *Proc Natl Acad Sci USA.* Mar. 1990;87(6):2264-8.
Karmakar, M. et al., Current Trends in Research and Application of Microbial Cellulases, Research Journal of Microbiology, (2001) 6(1): 41-53.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.

(56) References Cited

OTHER PUBLICATIONS

Kiick, K.L. et al., Identificationof an Expanded Set of Translationally Active Methionine Analogues in *Escherichia coli*, tetrahedron 56:9487, 2001.
Kim et al., "Localization of the site of the murine IgG1 molecule that is involved in binding to the murine intestinal Fe receptor," *Eur. J. Immunol.*, 1994, 24:2429-2434.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "α-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Köhler et al., "Continuous cultures of fused cells secreting antibody of predefined specificity," *Nature*, Aug. 7, 1975, 256(5517):495-497.
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kontermann, "Intrabodies as therapeutic agents," *Methods*, Oct. 2004, 34(2):163-170.
Kos, "Regulation of adaptive immunity by natural killer cells," *Immunol. Res.*, 1998, 17(3):303-312.
Koshihara et al., 1984, Biochmica et biophysica acta, 792(1), pp. 92-97.
Kostelny et al., "Formation of a bispecific antibody by the use of leucine zippers," *J. Immunol.*, Mar. 1, 1992, 148(5):1547-1553.
Kotteas et al., Immunotherapy for pancreatic cancer, J cancer Res Clin Oncol, 142(8): 1795-1805, 2016.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.

Kudo et al., "Up-regulation of a set of glycosyltransferase genes in human colorectal cancer," *Lab. Invest.*, Jul. 1998, 78(7):797-811.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific $CD4^+$ and $CD4^-8^-$ T cells in mice and humans," *J. Exp. Med.*, Sep. 1, 1994, 180(3):1097-1106.
Lau et al., "N-Glycans in cancer progression," *Glycobiology*, Oct. 2008, 18(10):750-760.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected αω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-Rev-HIV-I antibody. Angew. Chem. Int. Ed. 43, 1000-1003, (2004.
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$. ed., 1975, pp. 73-75, Worth Publishers, New York.
Lemieux, R. U. et al., Halide ion catalyzed glycosidation reactions. Syntheses of a-linked disaccharides. J Am. Chem. Soc. 97(14), 4056-62, (1975).
Leung et al., "A method for random mutagenesis of a defined DNA segment using a modified polymerase chain reaction," *Technique—A Journal of Methods in Cell and Molecular Biology*, Aug. 1989, 1(1):11-15.
Lew et al., Discovery and Development of GS 4104 (oseltamivir): an Orally Active Influenza Neuraminidase Inhibitor, Curr Med Chem, Jun. 2000, 7(6):663-672.
Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification ofxanthone and xanthene-based fluorophores using click chemistry." Org. Lett. 2009, 11, 3008-3011.
Li, Lingling, et al., Syntheses and spectral properties of functionalized, water-soluble BODIPY derivatives." J. Org. Chem. 2008, 73, 1963-1970.

(56) References Cited

OTHER PUBLICATIONS

Li, L. et al. Efficient chemoenzymatic synthesis of an N-glycan isomer library. Chem. Sci. 6, 5652-5661 (2015).
Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.
Lin et al., A common glycan structure on immunoglobulin G for enhancement of effector functions, PNAS, Aug. 25, 2015, vol. 112, No. 34, p. 10611-10616.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood*. May 15, 2007;109(10):4336-42. Epub Jan. 23, 2007.
Liu et al., "Activity-based protein profiling: the serine hydrolases," *Proc. Natl. Acad. Sci. USA*, Dec. 21, 1999, 96(26):14694-14699.
Liu et al., "Eradication of large colon tumor xenografts by targeted delivery of maytansinoids," *Proc. Natl., Acad. Sci. U.S.A.*, Aug. 6, 1996, 93(16):8618-8623.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
LoBuglio et al., "Mouse/human chimeric monoclonal antibody in man: kinetics and immune response," *Proc. Natl. Acari. Sci. U.S.A.*, Jun. 1989, 86(11):4220-4224.
Lode et al., "Targeted therapy with a novel enediyne antibiotic calicheamicin $\Theta^{I}_{1}$ effectively suppresses growth and dissemination of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Louis et al., "The 2007 WHO classification of tumours of the central nervous system," *Acta. Neuropathol.*, Aug. 2007, 114(2):97-109.
Lu et al., "Design of a mechanism-based probe for neuraminidase to capture influenza viruses," *Angew. Chem. Int. Ed. Engl.*, Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
Lu et al., "Single chain anti-c-Met antibody conjugated nanoparticles for in vivo tumor-targeted imaging and drug delivery," *Biomaterials*, Apr. 2011, 32(12):3265-3274.

MacBeath, G. and Schreiber, S. L., Printing Proteins as Microarrays for High-Throughput Function Determination, Science, 289, 1760-1763, 2000.
Macfarlane GT, et al., "Formation of glycoprotein degrading enzymes by Bacteroides fragilis" *FEMS Microbiol Lett*. Jan. 15, 1991;61(2-3):289-93.
Makino et al., Predominant expression of invariant $V_\alpha 14^+$ TCR $\alpha$ chain in NK1.1$^+$ T cell populations, *Int. Immunol.*, Jul. 1995, 7(7):1157-1161.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Mandal, M., Dudkin, V. Y., Geng, X. & Danishefsky, S. J. In pursuit of carbohydrate-based HIV vaccines, part I: The total synthesis of hybrid-type gp 120 fragments. Anfew. Chem. Int. Ed. 43, 2557-2561, (2004).
Månsson et al., "Characterization of new gangliosides of the lactotetraose series in murine xenografts of a human glioma cell line," *FEBS Lett.*, May 26, 1986, 201(1):109-113.
Marasco et al., "Design, intracellular expression, and activity of a human antihuman immunodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.
Marcato et al., "Chapter 17: The Rocky Road from Cancer Stem Cell Discovery to Diagnostic Applicability," Cancer Stem Cells Theories and Practice, pp. 335-360, Mar. 22, 2011.
Marks et al., "By-passing immunization. Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 1992, 10(7):779-783.
Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 1980, 23(1):243-252.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matsuda et al., "Structure and physical map of 64 variable segments in the 3' 0.8-megabase region of the human immunoglobulin heavy-chain locus," *Nature Genet.*, Jan. 1993, 3(1):88-94.
Matz et al., "Fluorescent proteins from nonbioluminescent *Anthozoa* species," *Nat. Biotechnol.*, Oct. 1999, 17(10):969-973.
McCafferty et al., "Phage antibodies: Filamentous phage displaying antibody variable domains," *Nature*, Dec. 6, 1990, 348:552-554.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Meezan et al., "Comparative studies on the carbohydrate-containing membrane components of normal and virus-transformed mouse

(56) References Cited

OTHER PUBLICATIONS fibroblasts: II: Separation of glycoproteins and glycopeptides by Sephadex chromatography," *Biochemistry*, Jun. 1969, 8(6):2518-2524.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Meyer, "Malignant gliomas in adults," *N. Engl. J. Med.*, Oct. 23, 2008, 359(17):1850.
Milstein, C & Cuello, AC, Hybrid Hydridomas and their use in immunohistochemistry, Nature 305, 537-540, Oct. 1993.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant *Mycobacterium bovis* BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," *Nature*, Oct. 4, 2001, 413(6855):531-534.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morelle, W. et al., "The Mass Spectrometric Analysis of Glycoproteins and their Glycan Structures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of $F(ab')_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morphy et al., Designed multiple ligands. An emerging drug discovery paradigm. J Med Chem. Oct. 20, 2005 ;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Moscona, "Global transmission of oseltamivir-resistant influenza," *N Engl. J Med*, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Thi, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Munson et al., "Ligand: a versatile computerized approach for characterization of ligand-binding systems," *Anal. Biochem.*, Sep. 1, 1980, 107(1):220-239.
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Ni, Jing et al., Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^{I}_{1}$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Noto et al., "CD44 and SSEA-4 positive cells in an oral cancer cell line HSC-4 possess cancer stem-like cell characteristics," *Oral Oncol.*, Aug. 2013, 49(8):787-795.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," *Immunity*, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," *Adv. Immunol.*, 1998, 70:281-312.
Olden, Kenneth et al., Carbohydrate Moieties of Glycoproteins: A Re-Evaluation of Their Function, Biochem et Biophys Acta 650:209-232 (1982).
Orlandi et al., "Cloning immunoglobulin variable domains for expression by the polymerase chain reaction," *Proc. Natl. Acad. Sci. U.S.A.*, May 1989, 86(10):3833-3837.

(56) References Cited

OTHER PUBLICATIONS

Ørum et al., "Efficient method for constructing comprehensive murine Fab antibody libraries displayed on phage." *Nucleic Acids Res.*, Sep. 25, 1993, 21(19):4491-4498.
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, O. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Papanastassiou et al., "The potential for efficacy of the modified (ICP 34.5⁻) herpes simplex virus HSV1716 following intratumoural injection into human malignant glioma: a proof of principle study," *Gene Therapy*, Mar. 2002, 9(6):398-406.
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," *Biochemistry*, Jan. 16, 2007, 46(2):350-358.
Paulson, J. C., Blixt, 0. & Collins, B. E. Sweet spots in functional glycomics. Nat. Chem. Biol. 2, 238-248, (2006).
Pearlman et al., *Peptide and Protein Drug Delivery, Chapter 6: Analysis of Protein Drugs*, Lee, ed., 1991, pp. 247-301, Marcel Dekker Publishing, New York.
Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.
Peipp et al., "Antibody fucosylation differentially impacts cytotoxicity mediated by NK and PMN effector cells," *Blood*, 2008, 112(6):2390-2399.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.
Perlmutter, R.M. et al., Subclass Restriction of Murine Anti-Carbohydrate Antibodies, Journal of lmmunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology, vol. 113: The Pharacology of Monoclonal Antibodies, Chapter 11: Antibodies from Escherichia coli*, Rosenberg et al., ers., 1994, pp. 269-315, Springer-Verlag, Berlin.
Poloukhtine et al., "Selective labeling of living cells by a photo-triggered click reaction," *J. Am. Chem. Soc.*, Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium ( 4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene*, Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res*. Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.

(56) References Cited

OTHER PUBLICATIONS

Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human lgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Natl. Acad. Sci. U.S.A.*, Feb. 1, 1994, 91(3):969-973.
Romagnani, "Induction of $T_H$ and $T_H 2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N. E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," *Nature*, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials, J. Biol. Chem. 267, 5700-5711, 1992.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schenkel-Brunner, *Human Blood Groups Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Sell, "Cancer-associated carbohydrates identified by monoclonal antibodies," *Hum. Pathol.*, Oct. 1990, 21(10):1003-1019.
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.

(56) References Cited

OTHER PUBLICATIONS

Shieh, Peyton et al., Fluorogenic Azidofluoresceins for Biological Imaging, J. Am. Chem. Soc. 2012, 134, 17428-17431.

Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.

Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.

Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).

Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.

Shriver, Zachary et al., Glycomics: a Pathway to a Class of New and Improved Therapeutics, Nat Rev Drug Disc, 2004, 3, 863-873.

Sidhu et al., "Phage-displayed antibody libraries of synthetic heavy chain complementarity determining regions," *J. Mol. Biol.*, Apr. 23, 2004, 338(2):299-310.

Siebenlist et al., "*E. coli* RNA polymerase interacts homologously with two different promoters," *Cell*, Jun. 1980, 20(2):269-281.

Sieber et al., "Proteomic profiling of metalloprotease activities with cocktails of active-site probes," *Nat. Chem. Biol.*, May 2006, 2(5):274-281.

Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.

Sivakumar, Krishnamoorthy et al., "A fluorogenic 1,3-dipolar cycloaddition reaction of 3-azidocoumarins and acetylenes." Org. Lett. 2004,24, 4603-4606.

Skehel, John et al., Receptor Binding and Membrane Fusion in Virus Entry: The Influenza Hemagglutinin, Ann. Rev Biochem, 69:531, 2000.

Skerra, "Bacterial expression of immunoglobulin fragments," *Curr. Opinion in Immunol.*, Apr. 1993, 5(2):256-262.

Slamon DJ, et al., Human breast cancer: correlation of relapse and survival with amplification of the HER-2/neu oncogene, *Science*. Jan. 9, 1987; 235(4785):177-82.

Sletten et al., "Bioorthogonal Chemistry: Fishing for Selectivity in a Sea of Functionality," *Angew. Che. Int. Ed. Engl.*, Aug. 27, 2009, 48(38):6974-6998.

Smith RA et al., "The active form of tumor necrosis factor is a trimer" *J Biol Chem.* May 25, 1987;262(15):6951-4.

Smyth MJ, et al., "CD4+CD25+ T regulatory cells suppress NK cell-mediated immunotherapy of cancer" *J Immunol.* Feb. 1, 2006;176(3):1582-7.

Sok, Devin et al., SnapShot: Broadly Neutralizing Antibodies. Cell 155, 728-728, (2013).

Solomons, G. and Fryhle, C., Chapter 5 Titled, Stereochemistry: Chiral Molecules, p. 184-228, in "Organic Chemistry," 7th Edition, Wiley, Jun. 18, 2001.

Soriano del Amo, David et al. Chemoenzymatic synthesis of the sialyl Lewis X glycan and its derivatives. Carbohydr. Res. 345, 1107-13, (2010).

Spinosa, Maria Rita et al., The Neisseria Meningitidis Capsule is Important for Intracellular Survival in Huamn Cells, Infect Immun 2001, 75, 3594-3603.

Srinivasan, Quantitative et al., Biochemical Rationale for Differences in Transmissibility of 1918 Pandemic Influenza A Viruses, Proc. Natl. Acad. Sci., 105, 2800-2805, 2008.

Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.

Stein, K.E., Thymus-Independent and Thymus-Dependent Responses to Polysaccharide Antigens, J Infect Dis 1992, 165 Suppl 1, S49-52.

Stephens, David, Conquering the Meningococcus, FEALS Microbial Rev 2007, 31, 3-14.

Stephens, D.S. et al., Epidemic Meningitis, Meningococcaemia, and Neisseria Meningitidis, Lancet 2007, 369, 2196-2210.

Stephenson et al., "Neuraminidase inhibitor resistance after oseltamivir treatment of acute influenza A and B in children," Clin. Infect. Dis., Feb. 15, 2009, 48(4):389-396.

Stevanovic, Stefan, Identification of Tumour-Associated T-Cell Epitopes for Vaccine Development, Nat. Rev. Cancer, 2002, 2, 514-520.

Stevens, James et al., Structure of the Uncleaved Human H1 Hemagglutinin From the Extinct 1918 Influenza Virus, Science, 303:1866, 2004.

Stevens, James et al., Structure and Receptor Specificity of the Hemagglutinin From an H5N1 Influenza Virus, Science, 312:404, 2006.

Stevens et al., Glycan Microarray Analysis of the Hemagglutinins From Modern and Pandemic Influenza Viruses Reveals Different Receptor Specificities. Journal of Molecular Biology 355.5 (2006): 1143-1155

Stickings, P. et al., nfect. Immun. 2008, 76, 1766.

Stockmann, H. et al., Development and Evaluation of New Cyclootynes for Cell Surface Glycan Imaging in Cancer Cells, J. Chem. Sci. 2011, 2, 932-936.

Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.

Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.

Su, G. Hahner, W. Thou "Investigation of the pore formation in anodic aluminum oxide" J Mater. Chem. 2008, 18 5787-5795.

Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).

Supplementary European Search Report in European Application No. EP 13775664.9, dated Oct. 27, 2015, in 7 pages.

Suresh et al., "Bispecific monoclonal antibodies from hybrid hybridomas," *Methods in Enzymology*, 1986, 121:210-228.

Sutton, VR et al., Bcl-2 Prevents Apoptosis Induced by Perforin and Granzyme B, But Not That Mediated by Whole Cytotoxic Lymphocytes, J of Immunology 1997, 158(12), 5783.

Suzuki E, et al., "A nonfucosylated anti-HER2 antibody augments antibody-dependent cellular cytotoxicity in breast cancer patients" *Clin Cancer Res.* Mar. 15, 2007;13(6):1875-82.

Svennerholm et al., "Human brain gangliosides: Developmental changes from early fetal stage to advanced age," *Biochim. Biophys. Acta*, Sep. 25, 1989, 1005(2):109-117.

Syrigos et al., "Antibody directed enzyme prodrug therapy (ADEPT): a review of the experimental and clinical considerations," *Anticancer Research*, Jan.-Feb. 1999, 19(1A):605-614.

Tahir et al., "Loss of IFN-γ production by invariant NK T cells in advanced cancer," *J. Immunol.*, Oct. 1, 2001, 167(7):4046-4050.

Takakura, Yoshimitsu et al., Molecular cloning, expression and properties of an alpha/beta-Galactoside alpha 2,3-sialyltransferase from *Vibrio* sp. JT- FAJ-16. J. Biochem. 142, 403-412, (2007).

Takano, Ryo et al., Sialylation and Malignant Potential in Tumour Cell Glycosylation Mutants, Glycobiology 4, 665-674 (1994).

Takeda et al., "Construction of chimaeric processed immunoglobulin genes containing mouse variable and human constant region sequences," *Nature*, Apr. 4-10, 1985, 314(6010):452-454.

(56) References Cited

OTHER PUBLICATIONS

Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry≠an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Taylor-Papadimitriou et al., "Exploiting altered glycosylation patterns in cancer: Progress and challenges in diagnosis and therapy," Trends Biotechnol., Jun. 1994, 12(6):227-233.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thorpe, (1985) "Antibody Carriers of Cytotoxic Agents in Cancer Therapy: A Review," in Monoclonal Antibodies '84: Biological and Clinical Applications, A. Pinchera et al. (ed.s), pp. 475-506.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Tomlinson et al., "The repertoire of human germline $V_H$ sequences reveals about fifty groups of $V_H$ segments with different hypervariable loops," J. Mol. Biol., Oct. 5, 1992, 227(3):776-798.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Traunecker et al., "Bispecific single chain molecules (Janusins) target cytotoxic lymphocytes on HIV infected cells," EMBO J., Dec. 1991, 10(12):3655-3659.
Traylor et al., "Gangliosides of human cerebral astrocytomas," J. Neurochem., Jan. 1980, 34(1):126-131.
Trinchieri, "Interleukin-12: a proinflammatory cytokine with immunoregulatory functions that bridge innate resistance and antigen-specific adaptive immunity," Annu. Rev. Immunol., 1995, 13:251-276.
Tsai et al., "Design and synthesis of activity probes for glycosidases," Org. Lett., Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai Ti, et al., "Effective sugar nucleotide regeneration for the large-scale enzymatic synthesis of Globo H and SSEA4" J Am Chem Soc. Oct. 2, 2013;135(39):14831-9, Epub Sep. 17, 2013.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tutt et al., "Trispecific F(ab')$_3$ derivatives that use cooperative signaling via the TCR/CD3 complex and CD2 to activate and redirect resting cytotoxic T cells," J. Immunol., Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" Glycobiology. Jan. 1996;6(1):83-93.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
Urlaub et al., "Isolation of Chinese hamster cell mutants deficient in dihydrofolate reductase activity." Proc. Natl. Acad. Sci. U.S.A., Jul. 1980, 77(7):4216-4220.
Valentine MA, et al., "Phosphorylation of the CD20 phosphoprotein in resting B lymphocytes. Regulation by protein kinase C" J Biol Chem. Jul. 5, 1989;264(19):11282-7.
Van Beek et al., "Increased sialic acid density in surface glycoprotein of transformed and malignant cells—a general phenomenon?" Cancer Res., Nov. 1973, 33(11):2913-2922.
Van der Horst et al., "Photoaffinity labeling of a bacterial sialidase with an aryl azide derivative of sialic acid," J. Biol. Chem., Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Van Meir et al., "Exciting new advances in neuro-oncology: the avenue to a cure for malignant glioma," CA Cancer J. Clin., May-Jun. 2010, 60(3):166-193.
Van Slambrouck et al., "Clustering of monosialyl-Gb5 initiates downstream signalling events leading to invasion of MCF-7 breast cancer cells," Biochem. J., Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," Nature, Apr. 26, 2007, 446(7139):1023-1029.
Vasella et al., "Synthesis of a phosphoric acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vaswani et al., "Humanized antibodies as potential therapeutic drugs," Ann. Allergy, Asthma Immunol., Aug. 1998, 81(2):105-116, 119.
Vavricka, Christopher et al., Influenza Neuraminidase Operates Via a Nucleophilic Mechanism and Can Be Targeted by Covalent Inhibitors, Nature Communcations, 4:1491 (2013).
Verhoeyen et al., "Reshaping human antibodies: grafting an antilysozyme activity," Science, Mar. 25, 1988, 239(4847):1534-1536.
Vermeer AW et al., "The thermal stability of immunoglobulin: unfolding and aggregation of a multi-domain protein" Biophys J. Jan. 2000;78(1):394-404.
Vinogradova et al., "Molecular mechanism of lysosomal sialidase deficiency in galactosialidosis involves its rapid degradation," Biochem. J., Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).

(56) References Cited

OTHER PUBLICATIONS

Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "Glycan microarray of Globe H and related structures for quantitative analysis of breast cancer," *Proc. Natl. Acad. Sci. U.S.A.*, Aug. 19, 2008, 105(33):11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus Ni neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from *Escherichia coli,*" Nature, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the lgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," *Cancer Metastasis Rev.*, 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." *Eur. J. Immunol.*, Jul. 1993, 23(7):1456-1461.
Wiltshire, S. et al. Proc. Natl. Acad. Sci. (2000) 97, 10113-10119.
Winter et al., "Making antibodies by phage display technology," *Annu. Rev. Immunol.*, 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woof et al., "Human antibody-Fc receptor interactions illuminated by crystal structures," *Nat. Rev. Immunol.*, Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.

(56) References Cited

OTHER PUBLICATIONS

Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yansura et al., "Nucleotide sequence selection for increased expression of heterologous genes in *Escherichia coli*," Methods: A Companion to Methods in Enzymol., Aug. 1992, 4(2):151-158.
Yates AJ et al., Brain Tumors in Childhood. Childs Brain 5(1), 31-39 (1979).
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "$CD41^{pos}$, $NK1.1^{pos}$ T cells promptly produce interleukin 4 in response to in vivo challenge with anti-CD3," *J. Exp. Med.*, Apr. 1, 1994, 179(4):1285-1295.
Yu et al., "Anti-GD2 antibody with GM-CSF, interleukin-2, and isotretinoin for neuroblastoma," *N. Engl. J. Med.*, Sep. 30, 2010, 363(14):1324-1334.
Yuen et al., Human infection by avian influenza A H5N1. Hong Kong Med J. Jun. 2005;1 1(3):189-99.
Zapata et al., "Engineering linear F(ab')2 fragments for efficient production in *Escherichia coli* and enhanced antiproliferative activity," *Protein Eng.*, Oct. 1995, 8(10):1057-1062.
Zarei et al., "Separation and identification of GMIb pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "New cerebrosides from Acanthopanax gracilistylus," CAPLUS 156:225776 (2011).
Zhang et al., "Selection of tumor antigens as targets for immune attack using immunohistochemistry: I. Focus on gangliosides," *Int. J. Cancer*, Sep. 26, 1997, 73(1):42-49.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.
Bacteroides Fragilis NCTC 9343, Complete Genome., Mar. 3, 2005, XP002775523, Database Accession No. CR626927, 2 Pages.

Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, Aug. 7, 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
Greene, Theodora et al., Protective Groups in Organic Synthesis, pp. 42-51 and 96-100, 1991.
Schelhaas, Michael et al., Protecting Group Strategies in Organic Synthesis, Angew. Chem. Int. Ed. Engl. 1996, 35, 2056-2083.
Unverzagt, Carlo et al., A Double Regio- and Stereoselective Glycosylation Strategy for the Synthesis of N-Glycans, Chem. Eur. J., 2008, 14, 1304-1311.
Cheung et al., Meeting Info: 23rd International Symposium on Glycoconjugates, GLYCO 23. Split, Croatia. Sep. 15, 2015-Sep. 20, 2015, vol. 32, No. 5, pp. 323.
Tsai, Charng-Sheng et al., Cell-Permeable Probe for Identification and Imaging of Sialidases, PNAS, vol. 110, No. 7, 2013, 2466-2471.
European Application 14817316.4, Communication pursuant to Article 94(3), dated Apr. 16, 2018, 5 pages.
Hodoniczky J, Zheng YZ, James DC. "Control of recombinant monoclonal antibody effector functions by Fc N-glycan remodeling in vitro" Biotechnology Progress. 2005;21(6):1644-1652.
Komarova TV, et al. "Trastuzumab and pertuzumab plant biosimilars: Modification of Asn297-linked glycan of the mAbs produced in a plant with fucosyltransferase and xylosyltransferase gene knockouts" Biochemistry (Moscow). Apr. 1, 2017;82(4):510-520.
Liu L. "Antibody glycosylation and its impact on the pharmacokinetics and pharmacodynamics of monoclonal antibodies and Fc-fusion proteins" Journal of Pharmaceutical Sciences. Jun. 2015;104(6):1866-1884.
Raju TS. "Terminal sugars of Fc glycans influence antibody effector functions of IgGs" Current Opinion in Immunology. Aug. 1, 2008;20(4):471-478.
Zhou Q, et al. "Site-specific antibody—drug conjugation through glycoengineering" Bioconjugate Chemistry. Feb. 28, 2014;25(3):510-520.
Herter et al "Glycoengineering of therapeutic antibodies enhances monocyte/macrophage-mediated phagocytosis and cytotoxicity" J Immunol. Mar. 1, 2014, vol. 192 No. 5, pp. 2252-2260.
Jez et al "Significant Impact of Single N-Glycan Residues on the Biological Activity of Fc-based Antibody-like Fragments" Journal of Biological Chemistry Jul. 13, 2012, vol. 287 No. 29, pp. 24313-24319.

(56) References Cited

OTHER PUBLICATIONS

Junttila et al "Superior in vivo efficacy of afucosylated trastuzumab in the treatment of HER2-amplified breast cancer" Cancer Res. 2010, vol. 70 No. 11, pp. 4481-4489.
Komarova et al "Plant-Made Trastuzumab (Herceptin) Inhibits HER2/Neu+ Cell Proliferation and Retards Tumor Growth" PLOS ONE 2011,vol. 6 No. 3, p. e17541.
McConville, Malcolm J., and M. A. Ferguson. "The structure, biosynthesis and function of glycosylated phosphatidylinositols in the parasitic protozoa and higher eukaryotes." Biochemical Journal 294.Pt 2 (1993): 305.
Ochiai et al "Expeditious Chemoenzymatic Synthesis of Homogeneous N-Glycoproteins Carrying Defined Oligosaccharide Ligands" J. Am. Chem. Soc. 2008, vol. 130 No. 41, pp. 13790-13803.
Office Action dated Aug. 29, 2017, from corresponding Japanese Patent Application No. 2016-169045, 5 total pages.
Tebbey et al "Importance of manufacturing consistency of the glycosylated monoclonal antibody adalimumab (Humira®) and potential impact on the clinical use of biosimilars" GABI Journal 2016, vol. 5 Issue 2, pp. 70-73.
Wiseman, Gregory A., et al. "Radiation dosimetry results and safety correlations from (90) Y-ibritumomab tiuxetan radioimmunotherapy for relapsed or refractory non-Hodgkin's lymphoma: Combined data from 4 clinical trials" The Journal of Nuclear Medicine 44.3 (2003): 465-474.
Zhang et al "Glycoengineered Pichia produced anti-HER2 is comparable to trastuzumab in preclinical study" mAbs May-Jun. 2011, vol. 3 No. 3, pp. 289-298.

\* cited by examiner

GLYCAN CONJUGATES AND METHODS OF USE THEREOF

CROSS-REFERENCE TO RELATED APPLICATIONS

This application claims the benefit under 35 U.S.C. 119(e) of U.S. Provisional Patent Application No. 62/107,378, filed on Jan. 24, 2015, entitled NOVEL GLYCAN CONJUGATES AND METHODS OF USE THEREOF, the contents of which is hereby incorporated by reference as if set forth in its entirety.

FIELD

The present disclosure relates to methods and compositions which can modulate the globo-series glycosphingolipid synthesis. Particularly, the present disclosure is directed to glycoenzyme inhibitor compound and compositions and methods of use thereof that can modulate the synthesis of globo-series glycosphingolipid SSEA3/SSEA4/GloboH in the biosynthetic pathway; particularly, the glycoenzyme inhibitors target the alpha-4GalT; beta-4GalNAcT-I; or beta-3GalT-V enzymes in the globo-series synthetic pathway. Additionally, the present disclosure is also directed to vaccines, antibodies, and/or immunogenic conjugate compositions targeting the SSEA3/SSEA4/GloboH associated epitopes (natural and modified) which can elicit antibodies and/or binding fragment production useful for modulating the globo-series glycosphingolipid synthesis. Moreover, the present disclosure is also directed to the method of using the compositions described herein for the treatment or detection of hyperproliferative diseases and/or conditions.

BACKGROUND OF THE INVENTION

The carbohydrate antigens GloboH, stage-specific embryonic antigen-3 (SSEA3), and stage-specific embryonic antigen-4 (SSEA4) are closely related to one another in either structure or in function. GloboH, SSEA3 and SSEA4 are globo-series glycosphingolipids, with SSEA3 being the non-fucosylated pentasaccharide precursor structure of GloboH, SSEA4 is sialylated SSEA3 with sialic acid α2-3 links to the non-reducing end of galactose of SSEA3.

Stage-specific embryonic antigen-3 (SSEA3) was first identified and defined by the reactivity of an IgM monoclonal antibody generated in a rat immunized with 4- to 8-cell stage mouse embryos. This monoclonal antibody reacted with all mouse preimplantation embryos from oocytes up to the early blastocyst stage where its expression became more restricted, in the primitive endoderm after implantation. The SSEA3 antigenic determinant was determined to be a carbohydrate present on glycolipids and glycoproteins; it was also found on human teratocarcinoma cells and human erythrocytes. In a panel of structures isolated from the 2102Ep human teratocarcinoma cell line, the SSEA3 antibody had the highest affinity for Gal β (1-3)GalNAcβ (1-3)Gal α (1-4)Gal β (1-4)Glc β (1)Cer. This structure is also known as Gb5, galactosyl-globoside, or globopentaosylceramide.

Synthesis of SSEA3 occurs when β 1,3-galactosyltransferase V (β3GalT-V) transfers galactose to the GalNAc of globoside to form Gb5 or galactosyl-globoside. It was determined that SSEA3 was not expressed in hematopoietic or mesenchymal stem cells. Based on immortalized lymph node lymphocytes from primary lung cancer patients, generated hybridomas, and selected for antibody secreting clones; monoclonal antibodies were then generated from two of these clones—J309 and D579, which recognized the SSEA3 antigenic determinant. The antibodies recognized SSEA3 on several tumor cell lines including lung and breast cancer cell lines, and a teratocarcinoma cell line; in an immune adherence assay, rodent monoclonal SSEA3 antibody, also referred to as MC631, reacted against the same cell lines as the J309 and D579 antibodies. SSEA3 has also been found on testicular germ cell tumors, as well as in breast cancer and in BCSCs (breast cancer stem cells).

Chang et al. looked at SSEA3 expression on normal tissues using a tissue microarray because its location outside of cancer and development was largely unknown. The group found SSEA3 to be expressed on normal epithelium of colon, esophagus, small intestine, kidney, prostate, rectum, skin, testis, thymus, and uterine cervix. Expression was located only on the apical surfaces of epithelial cells or in the cytoplasm, which are considered immune system restricted or inaccessible sites. In an experiment using a KLH conjugated GloboH monovalent vaccine in mice, an antibody response was made to only the GloboH antigen. When α-GalCer was added as an adjuvant, the amount of overall antibody production increased and the mice made polyclonal antibodies to both the GloboH, the SSEA3 and the SSEA4 antigen structures, which vaccination was unable to generate in the absence of the adjuvant. This result showed that SSEA3, GloboH and SSEA4 could make promising targets for cancer vaccines and could be targeted simultaneously.

However, most tumor associated carbohydrate antigens have poor immunogenicity and many approaches have been developed to increase the immune response of carbohydrate-based vaccines, including conjugation with a carrier protein, administration with an immunologic adjuvant using unnatural glycosidic linkage, clustered antigens, unimolecular polyvalent vaccine or hetero-glycan multivalent vaccine. Using these strategies, a few carbohydrate-based vaccines that could elicit significant immune responses to target glycan structures were designed for cancer therapy and entered clinical trials. Among them, the clinical trials of Theratope and GMK with adjuvant QS-21 failed to produce statistically significant difference between time-to-disease and overall survival rate. Mot likely these two vaccines could not elicit robust T cell-dependent immune response in patients. Specifically, Theratope and GMK induced a higher level of IgM in patients but could not induce a strong immune IgG response, which is a major problem in carbohydrate-based vaccine development.

Previous studies showed that modification of carbohydrate antigen structures (MCAS) could effectively elicit a higher level of immune response. For example, in the modification study of the capsular polysaccharide of group B meningococci, the N-acetyl groups of α-(2,8)-linked polysialic acid (PSA) was replaced with the N-propinoyl group and such a modification elicited a high antibody response to recognize not only the N-propinoyl PSA, but also the nature N-acetyl PSA. Similar approaches were applied to STn and GM3 antigens to produce high antibody titers against modified and nature forms. The results indicated that N-phenylacetyl, N-fluoroacetyl or N-difluoroacetyl modifications on glycan antigens could improve the immunogenicity. Moreover, the Schultz group reported that incorporation of a p-nitrophenylalanine into the tumor necrosis factor-α (TNF-α) could break immune tolerance and induce more antibody response to TNF-α. Using glycans as antigens, although some progress has been achieved, most cases are the N-modification of disaccharide (STn), trisaccharide (GM3) and polysialic acid (PSA) and some are based on fluorinated MUC1 glycopeptide antigens.

Additionally, the present disclosure is also directed to vaccines and/or immunogenic conjugate compositions targeting the SSEA3/SSEA4/GloboH associated epitopes (natural and modified) which can elicit antibodies and/or binding fragment production useful for modulating the globo-series glycosphingolipid synthesis. Moreover, the present disclosure is also directed to the method of using the compositions described herein for the treatment or detection of hyperproliferative diseases and/or conditions.

Accordingly, the present invention features the design of antibodies against SSEA3 for treating cancers. The present invention also features novel compounds consisting of the modified carbohydrate antigens (SSEA3, SSEA4), glycan conjugates comprising such, and immunogenic compositions and vaccines thereof.

In one aspect, the present invention provides a compound of formula (I):

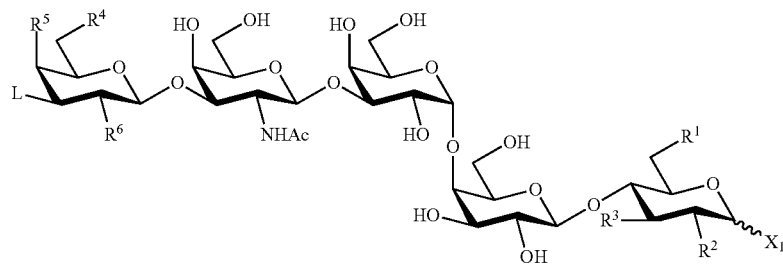

SUMMARY OF THE INVENTION

The present disclosure is based on the discovery that the modification of the stage-specific embryonic antigens (SSEA3 and SSEA4) with certain groups disclosed herein (I), or a salt thereof, wherein $X_1$, $R^1$, $R^2$, $R^3$, $R^4$, $R^5$, $R^6$ and L are as described herein. In certain embodiments, a compound of Formula (I) is useful for making an immunogenic composition for treating cancers.

In another aspect, the present invention provides a compound of Formula (II):

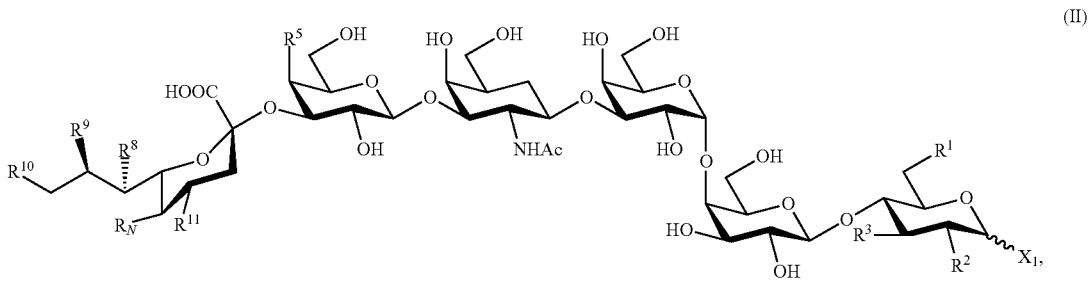

elicited robust IgG antibody response to specifically recognize SSEA3 and SSEA4, respectively. The antibodies induced by an immunogenic composition comprising such unnatural glycan moiety are able to mediate the complement-dependent cell cytotoxicity against tumor cells.

Accordingly, the present invention features the design of antibodies against SSEA3 and/or SSEA4 for treating cancers. The present invention also features novel compounds consisting of the modified carbohydrate antigens (SSEA3 and SSEA4), glycan conjugates comprising such, and immunogenic compositions and vaccines thereof.

The present disclosure also provides methods of using synthetic glycan conjugates described herein to treat or reduce hyperproliferative disease such as cancer.

or a salt thereof, wherein $X_1$, $R^1$, $R^2$, $R^3$, $R^8$, $R^9$, $R^{10}$, $R^{11}$ and $R_N$ are as described herein. In certain embodiments, a compound of Formula (II) is useful for making an immunogenic composition for treating cancers.

In another aspect, the present invention provides an immunogenic composition, comprising (a) a glycan conjugate including a carrier and one or more glycans, and optionally (b) an adjuvant, wherein: each of the one or more glycans is conjugated with the carrier through a linker, having the formula (III) or (IV):

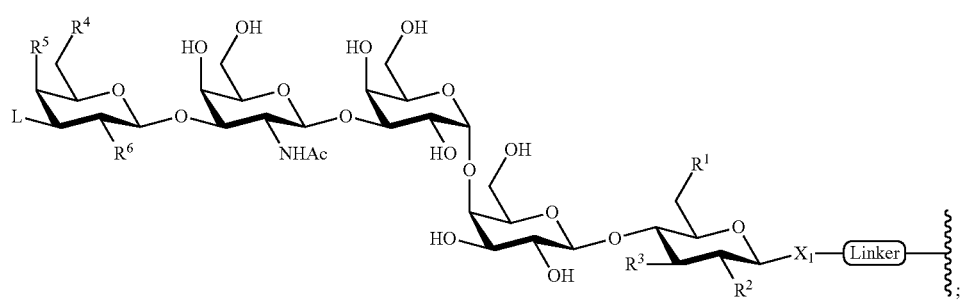

(III)

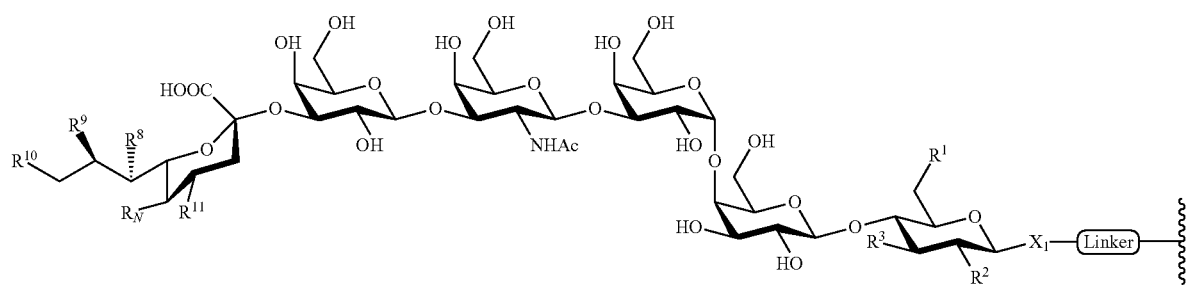

(IV)

wherein $X_1$, $R^1$, $R^2$, $R^3$, $R^4$, $R^5$, $R^6$, $R^8$, $R^9$, $R^{10}$, $R^{11}$, L and $R_N$ are as described herein.

In certain aspects, it is contemplated that any construct of vaccine containing a combination of any one or more of the three glycans (SSEA3, SSEA4 and GloboH) and analogs thereof in any ratio can be linked to a carrier.

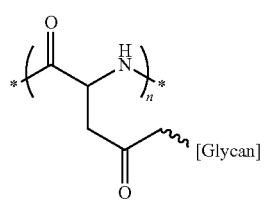

wherein n can be an integer from 1 to 10;

wherein Glycan can be selected from the group consisting of Formulas I, II, III, and IV;

wherein if n is 2 or more, each Glycan can be the same as another Glycan on the aspartyl peptide or a difference Glycan on the aspartyl peptide.

In some embodiments, Glycan can be selected from the group consisting of SSEA3, SSEA4, and GloboH.

In some embodiments, the exemplary multivalent construct can be:

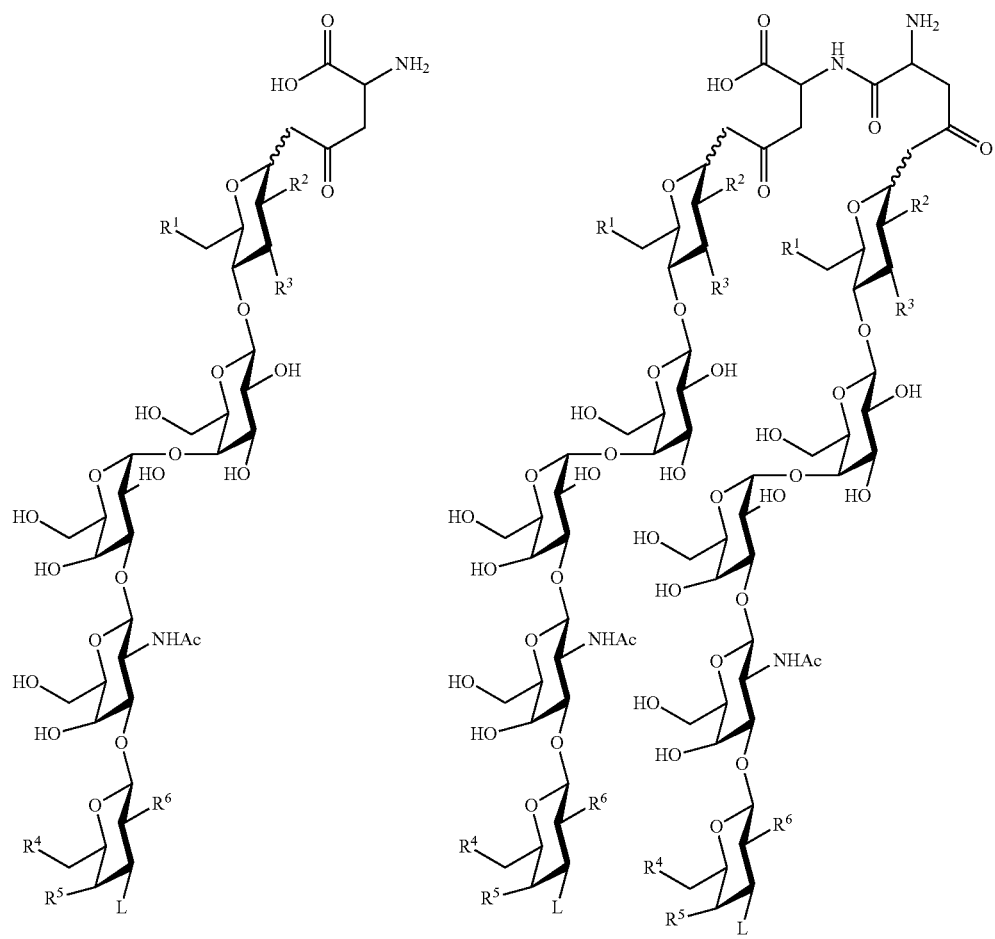

-continued

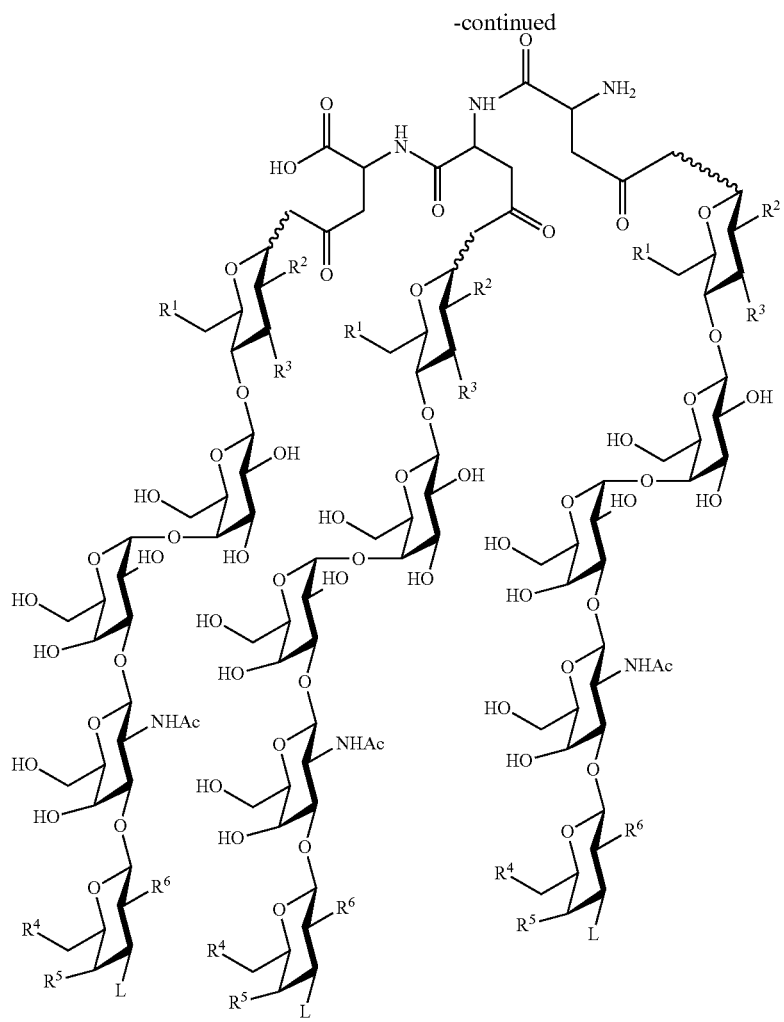

wherein R1, R2, R3, R4, R5, R6, and L on each glycan moiety can be the same or different.

In certain embodiments, the immunogenic composition of the invention comprises an adjuvant. Exemplary adjuvants suitable for the invention are as described herein.

In certain embodiments, the immunogenic composition is capable of eliciting an immune response against a cancer cell in a subject. In certain embodiments, the cancer cell is selected from the group consisting of a brain cancer cell, a lung cancer cell, a breast cancer cell, an oral cancer cell, an esophageal cancer cell, a stomach cancer cell, a liver cancer cell, a bile duct cancer cell, a pancreatic cancer cell, a colon cancer cell, a kidney cancer cell, a bone cancer cell, a skin cancer cell, a cervical cancer cell, an ovarian cancer cell, and a prostate cancer cell.

In certain embodiments, the immune response includes generation of antibodies that specifically bind to one or more of the antigens selected from the group consisting of GloboH, SSEA3 and SSEA4. In certain embodiments, the antibodies are developed to target one or more of GloboH, SSEA3 and SSEA4 expressed on the surface of cancer cells or cancer stem cells, and trigger CDC and/or ADCC to kill these cells. In certain embodiments, the antibodies predominantly include IgG antibodies. In certain embodiments, the immunogenic compositions provided herein mainly induce IgG1, IgG2b, IgG2c and IgG3.

Further, the present disclosure features monoclonal antibodies and binding fragments raised against the immunogenic composition described herein.

In one embodiment, the antibody is a human antibody.

In one embodiment, the antibody is a humanized antibody.

In one embodiment, the antibody is specifically targeted against one or more of SSEA4, SSEA3, or GloboH.

In one embodiment, the antibody is specifically targeted against SSEA3.

In one embodiment, the antibody is specifically targeted against SSEA4.

In one embodiment, the antibody is a homogeneous antibody having the biantennary glycan terminated by two sialic acid in alpha-2,6-linkage.

In one aspect, the present disclosure provides a pharmaceutical composition comprising an effective amount of the antibody or antigen-binding fragment specifically targeted against one or more of SSEA4, SSEA3, or GloboH and a pharmaceutically acceptable carrier In one embodiment, the pharmaceutical composition comprises a combination of antibodies and/or binding fragment thereof each independently targeting one or more of the SSEA4, SSEA3, and/or GloboH glycans.

In one embodiment, the pharmaceutical composition is useful for the treatment of cancer, infectious diseases, and/or anti-inflammatory diseases, In one embodiment, the pharmaceutical composition comprises antibodies or binding fragments thereof having universal biantennary N-glycan terminated with sialic acid in alpha-2,6-linkage.

In another aspect, the present invention provides a cancer vaccine comprising an immunogenic composition described herein and a pharmaceutically acceptable excipient.

In another aspect, the present invention provides methods for treating and/or reducing the risk for cancer in a subject comprising administering to a subject in need thereof a therapeutically effective amount of an immunogenic composition or a cancer vaccine as described herein.

The treatment results in reduction of tumor size, elimination of malignant cells, prevention of metastasis, prevention of relapse, reduction or killing of disseminated cancer, prolongation of survival and/or prolongation of time to tumor cancer progression.

In some embodiments, the treatment further comprises administering an additional therapy to the subject prior to, during or subsequent to the administering of the immunogenic composition or the cancer vaccine described herein. In some embodiments, the additional therapy is treatment with a chemotherapeutic agent. In some embodiments, the additional therapy is radiation therapy.

Another aspect of the present disclosure features a method of vaccinating a mammal against cancers, comprising administering to the mammal a pharmacologically effective amount of an immunogenic composition or a cancer vaccine as described herein.

In some embodiments, the mammal is a human. In some embodiments, the immunogenic composition or the cancer vaccine described herein is administered subcutaneously.

Examples of the cancer include, but are not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In some embodiments, the cancer is brain cancer, lung cancer, breast cancer, ovarian cancer, prostate cancer, colon cancer, or pancreas cancer.

In another aspect, the present invention provides methods of synthesizing the compounds of the invention as described herein.

In yet another aspect, the present disclosure features the process for making an immunogenic composition or a cancer vaccine as described herein.

The details of certain embodiments of the invention are set forth herein. Other features, objects, and advantages of the invention will be apparent from the Detailed Description, the Figures, the Examples, and the Claims.

DETAILED DESCRIPTIONS

Figure 1:
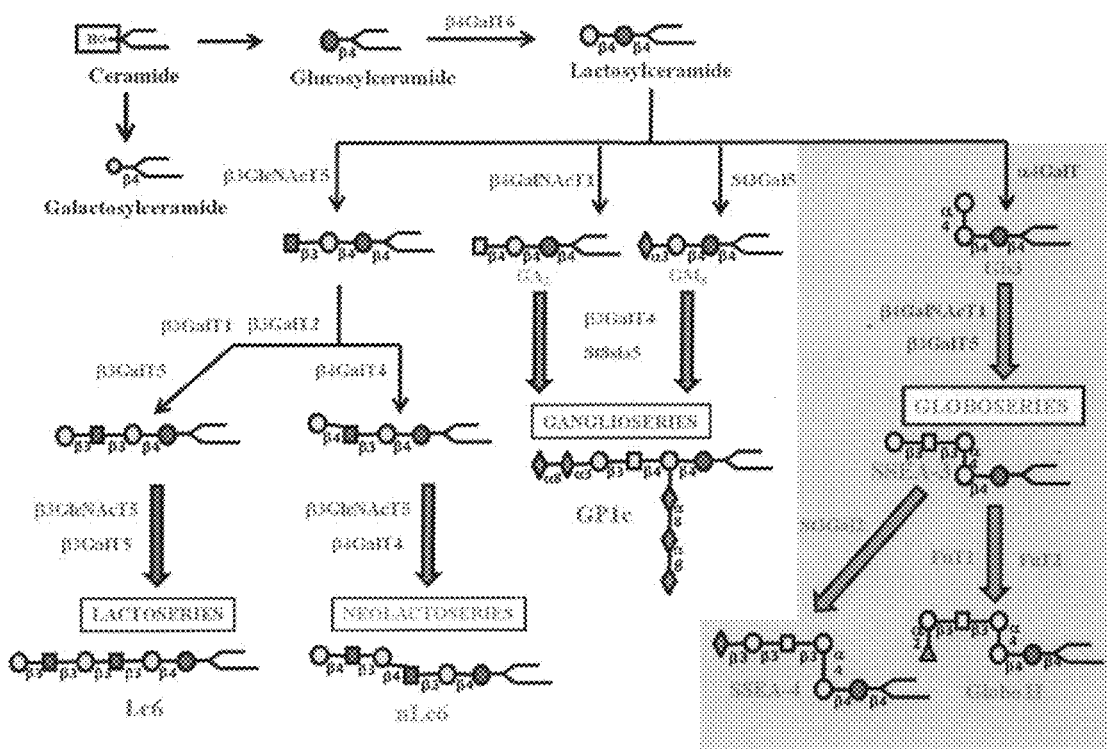
FIG. 1: Biosynthetic Pathway of Globo Series of Glycosphingolipids.
Figure 2:
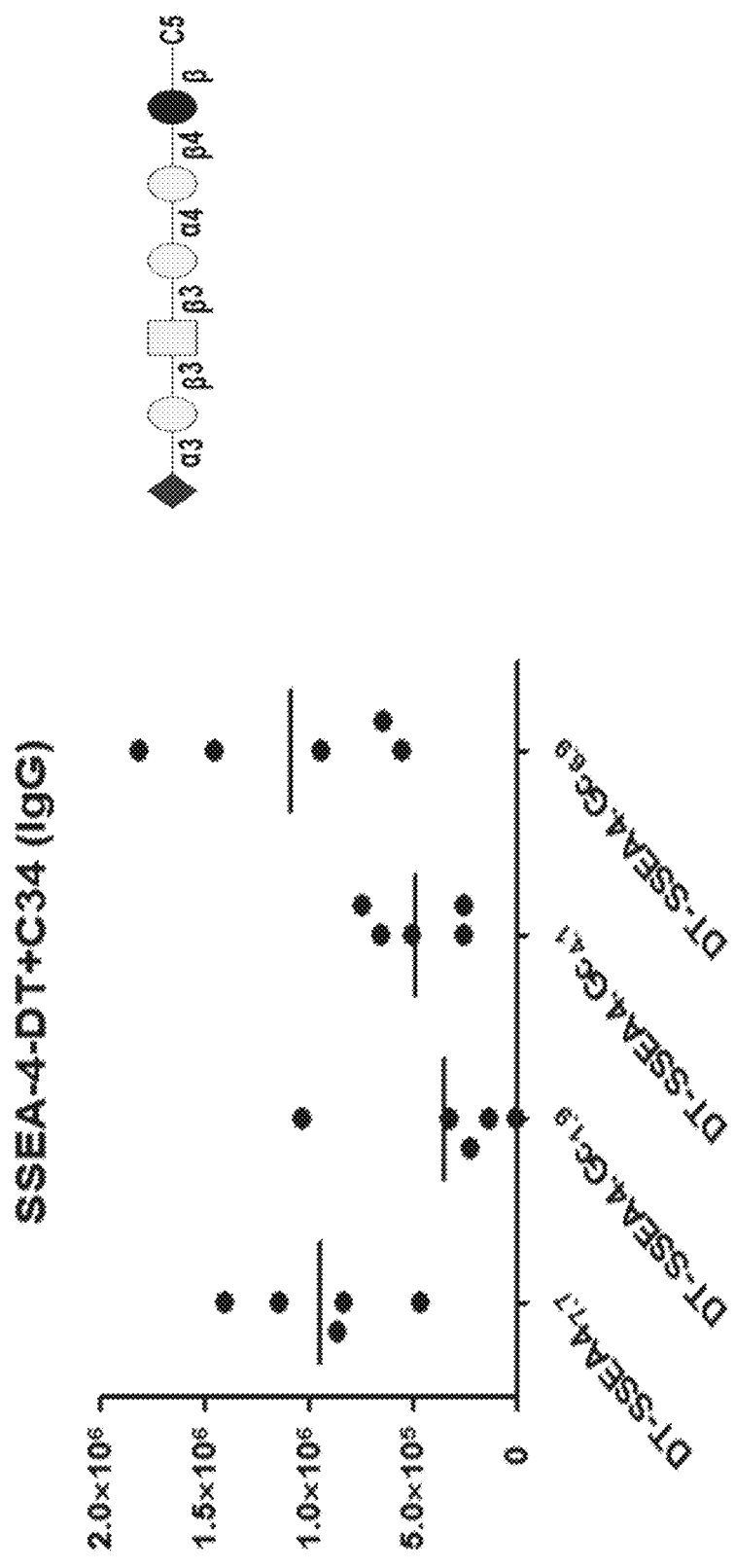
FIG. 2: The induced GloboH-IgG collected from different epitope ratios of SSE4-CRM197 or SSEA4-Gc-CRM197 immunization.

The present disclosure is based on the surprising discovery that the modification of the stage-specific embryonic antigens (SSEA3 and SSEA4) with certain groups elicited robust IgG antibody response to specifically recognize SSEA3 and SSEA4, respectively.

In some examples, the modification of SSEA3 comprises a fluoro, an azido or an O-phenyl group at the one or more positions of the glucose of SSEA3. In some examples, the modification of SSEA3 comprises a fluoro, an azido or an O-phenyl group at the one or more positions of the non-reducing end galactose. In some examples, the modification of SSEA4 comprises a fluoro, an azido or an O-phenyl group at one or more positions of the glucose of SSEA4. In some examples, the modification of SSEA4 comprises a fluoro, an azido or an O-phenyl group at one or more positions of the sialic acid residue.

Described herein are SSEA3 and SSEA4 analogs having the modification at the reducing and/or non-reducing end. Such SSEA3 and SSEA4 analogs can elicit a stronger immune response (e.g., induction of IgG antibodies against SSEA3 and/or SSEA4) as compared to the native SSEA3 and SSEA4. The antibodies induced by an immunogenic composition comprising such unnatural glycan moiety are able to mediate the complement-dependent cell cytotoxicity against tumor cells.

Chemical Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987. Moreover, exemplary glycan and antibody methodologies are described in Wong et al, US20100136042, US20090317837, and US20140051127, the disclosures of each of which are hereby incorporated by reference.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, N Y, 1962); and Wilen, Tables of Resolving Agents and Optical Resolutions p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "C1-6" is intended to encompass C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6.

"Alkyl" refers to a radical of a straight-chain or branched saturated hydrocarbon group having from 1 to 20 carbon atoms ("C1-20 alkyl"). In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 6 carbon atoms ("C2-6 alkyl"). Examples of C1-6 alkyl groups include methyl (C1), ethyl (C2), n-propyl (C3), iso-propyl (C3), n-butyl (C4), tert-butyl (C4), sec-butyl (C4), iso-butyl (C4), n-pentyl (C5), 3-pentanyl (C5), amyl (C5), neopentyl (C5), 3-methyl-2-butanyl (C5), tertiary amyl (C5), and n-hexyl (C6). Additional examples of alkyl groups include n-heptyl (C7), n-octyl (C8) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted C1-10 alkyl (e.g., —CH3). In certain embodiments, the alkyl group is substituted C1-10 alkyl.

"Alkenyl" refers to a radical of a straight-chain or branched hydrocarbon group having from 2 to 20 carbon atoms, one or more carbon-carbon double bonds, and no triple bonds ("C2-20 alkenyl"). In some embodiments, an alkenyl group has 2 to 10 carbon atoms ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl groups include ethenyl (C2), 1-propenyl (C3), 2-propenyl (C3), 1-butenyl (C4), 2-butenyl (C4), butadienyl (C4), and the like. Examples of C2-6 alkenyl groups include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C2-10 alkenyl. In certain embodiments, the alkenyl group is substituted C2-10 alkenyl.

"Alkynyl" refers to a radical of a straight-chain or branched hydrocarbon group having from 2 to 20 carbon atoms, one or more carbon-carbon triple bonds, and optionally one or more double bonds ("C2-20 alkynyl"). In some embodiments, an alkynyl group has 2 to 10 carbon atoms ("C2-10 alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("C2-4 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl (C3), 2-propynyl (C3), 1-butynyl (C4), 2-butynyl (C4), and the like. Examples of C2-6 alkenyl groups include the aforementioned C2-4 alkynyl groups as well as pentynyl (C5), hexynyl (C6), and the like. Additional examples of alkynyl include heptynyl (C7), octynyl (C8), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C2-10 alkynyl. In certain embodiments, the alkynyl group is substituted C2-10 alkynyl.

"Heterocyclyl" or "heterocyclic" refers to a radical of a 3-to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

"Aryl" refers to a radical of a monocyclic or polycyclic (e.g., bicyclic or tricyclic) 4n+2 aromatic ring system (e.g., having 6,10, or 14 π electrons shared in a cyclic array) having 6-14 ring carbon atoms and zero heteroatoms in the aromatic ring system ("C6-14 aryl"). In some embodiments, an aryl group has six ring carbon atoms ("C6 aryl"; e.g., phenyl). In some embodiments, an aryl group has ten ring carbon atoms ("C10 aryl"; e.g., naphthyl such as 1-naphthyl and 2-naphthyl). In some embodiments, an aryl group has fourteen ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C6-14 aryl. In certain embodiments, the aryl group is substituted C6-14 aryl.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

The term "alkoxy" or "alkyloxy" refers to an —O-alkyl radical, wherein alkyl is optionally substituted alkyl as defined herein. Examples of alkoxy include, but are not limited to, methoxy, ethoxy, n-propoxy, isopropoxy, n-butoxy, iso-butoxy, sec-butoxy, and tert-butoxy.

The term "aryloxy" refers to an —O-aryl, wherein aryl is optionally substituted aryl as defined herein.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)Raa, —CHO, —CO2Raa, —C(=O)N(Rbb)2, —C(=NRbb)Raa, —C(=NRbb)ORaa, —C(=NRbb)N(Rbb)2, —C(=O)NRbbSO2Raa, —C(=S)N(Rbb)2, —C(=O)SRaa, and —C(=S)SRaa, wherein Raa and Rbb are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —ORaa, —N(Rcc)2, —CN, —C(=O)Raa, —C(=O)N(Rcc)2, —CO2Raa, —SO2Raa, —C(=NRbb)Raa, —C(=NRcc)ORaa, —C(=NRcc)N(Rcc)2, —SO2N(Rcc)2, —SO2Rcc, —SO2ORcc, —SORaa, —C(=S)N(Rcc)2, —C(=O)SRcc, —C(=S)SRcc, —P(=O)2Raa, —P(=O)(Raa)2, —P(=O)2N(Rcc)2, —P(=O)(NRcc)2, C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Rcc groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups, and wherein Raa, Rbb, Rcc, and Rdd are as defined above.

In certain embodiments, the substituent present on an oxygen atom is an oxygen protecting group (also referred to as a hydroxyl protecting group). Oxygen protecting groups include, but are not limited to, —Raa, —N(Rbb)2, —C(=O)SRaa, —C(=O)Raa, —CO2Raa, —C(=O)N(Rbb)2, —C(=NRbb)Raa, —C(=NRbb)ORaa, —C(=NRbb)N(Rbb)2, —S(=O)Raa, —SO2Raa, —Si(Raa)3, —P(Rcc)2, —P(Rcc)3, —P(=O)2Raa, —P(=O)(Raa)2, —P(=O)(ORcc)2, —P(=O)2N(Rbb)2, and —P(=O)(NRbb)2, wherein Raa, Rbb, and Rcc are as defined herein. Oxygen protecting groups are well known in the art and include those described in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "CD1d" refers to a member of the CD1 (cluster of differentiation 1) family of glycoproteins expressed on the surface of various human antigen-presenting cells. CD presented lipid antigens activate natural killer T cells. CD1 d has a deep antigen-binding groove into which glycolipid antigens bind. CD1 d molecules expressed on dendritic cells can bind and present glycolipids, including alpha-GalCer analogs such as C34.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding," refers to the interaction between binding pairs (e.g., an antibody and an antigen). In various instances, specifically binding can be embodied by an affinity constant of about 10-6 moles/liter, about 10-7 moles/liter, or about 10-8 moles/liter, or less.

As used herein, the terms glycoenzymes refers to at least in part the enzymes in the globo-series biosynthetic pathway; exemplary glycoenzymes include alpha-4GalT; beta-4GalNAcT-I; or beta-3GalT-V enzymes.

As used herein, the term "globo-series pathway" includes to a biosynthetic and enzymatic pathways described in FIG. 1.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "globo-series-related disorder" refers to or describes a disorder that is typically characterized by or contributed to by aberrant functioning or presentation of the pathway. Examples of such disorders include, but are not limited to, hyperproliferative diseases, including cancer.

Examples of immunologic deficiency syndromes include, but are not limited to, ataxia telangiectasia, leukocyte-adhesion deficiency syndrome, lymphopenia, dysgammaglobulinemia, HIV or deltaretrovirus infections, common variable immunodeficiency, severe combined immunodeficiency, phagocyte bactericidal dysfunction, agammaglobulinemia, DiGeorge syndrome, and Wiskott-Aldrich syndrome. Examples of hypersensitivity include, but are not limited to, allergies, asthma, dermatitis, hives, anaphylaxis, Wissler's syndrome, and thrombocytopenic purpura.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32, Pb212 and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

In one aspect, the present disclosure is based on the surprising discovery that the modification of the stage-specific embryonic antigens (SSEA3 and SSEA4) with certain groups elicited robust IgG antibody response to specifically recognize SSEA3 and SSEA4, respectively.

In some examples, the modification of SSEA3 comprises a fluoro, an azido or an O-phenyl group at the one or more positions of the glucose of SSEA3. In some examples, the modification of SSEA3 comprises a fluoro, an azido or an O-phenyl group at the one or more positions of the non-reducing end galactose. In some examples, the modification of SSEA4 comprises a fluoro, an azido or an O-phenyl group at one or more positions of the glucose of SSEA4. In some examples, the modification of SSEA4 comprises a fluoro, an azido or an O-phenyl group at one or more positions of the sialic acid residue.

In certain aspects, the present disclosure provides SSEA3 and SSEA4 analogs having the modification at the reducing and/or non-reducing end. Such SSEA3 and SSEA4 analogs can elicit a stronger immune response (e.g., induction of IgG antibodies against SSEA3 and/or SSEA4) as compared to the native SSEA3 and SSEA4. The antibodies induced by an immunogenic composition comprising such unnatural glycan moiety are able to mediate the complement-dependent cell cytotoxicity against tumor cells.

Compounds

Accordingly, the present invention also features novel compounds consisting of the modified carbohydrate antigens (SSEA3 and SSEA4), glycan conjugates comprising such, and immunogenic compositions and vaccines thereof.

In one aspect, the present invention provides a compound of formula (I):

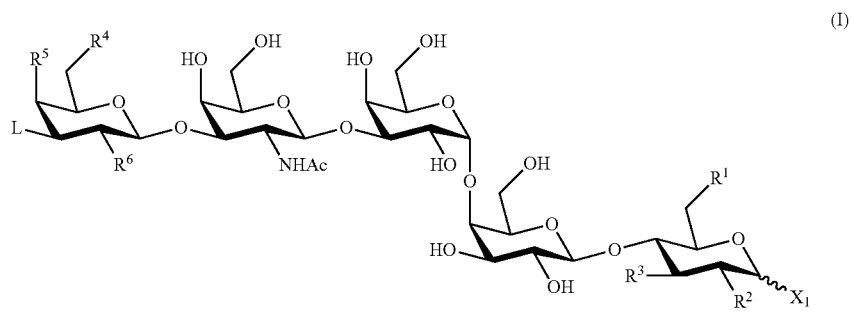

or a salt thereof,
wherein:
X1 is —OR or —SR, wherein R is hydrogen, a oxygen or sulfur protecting group, optionally substituted C1-10 alkyl, optionally substituted aryl, optionally substituted acyl, or optionally substituted imidoyl;
each instance of R1, R2, R3, R4, R5, R6 and L is independently selected from hydrogen, halogen, optionally substituted alkyl, optionally substituted alkenyl, optionally substituted alkynyl, optionally substituted heterocyclyl, optionally substituted aryl, —N3, —NO2, —N(RB)2, —N(RA)C(O)RA, —ORA, —OC(O)RA, —SRA, —C(O)N(RB)2, —CN, —C(O)RA, —C(O)ORA, —S(O)RA, —SO2RA, —SO2N(RB)2, and —NHSO2RB;
each instance of RA is independently selected from hydrogen, optionally substituted alkyl, optionally substituted alkenyl, optionally substituted alkynyl, optionally substituted heterocyclyl, and optionally substituted aryl;

each instance of RB is independently selected from hydrogen, optionally substituted alkyl, optionally substituted alkenyl, optionally substituted alkynyl, optionally substituted heterocyclyl, and optionally substituted aryl; and provided the compound is not of the formula:

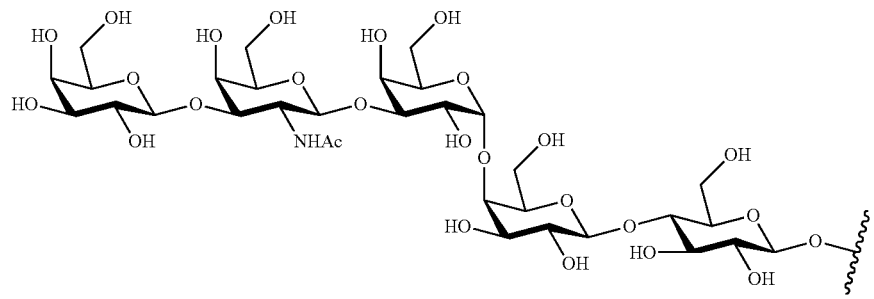

In certain embodiments, X1 is in the alpha configuration. In certain embodiments, X1 is in the beta configuration.

In some embodiments, X1 is —ORA. In some embodiments, X1 is —OH. In some embodiments, X1 is —O(protecting group). In some embodiments, X1 is —ORA, wherein RA is unsubstituted C1-10 alkyl. In some embodiments, X1 is —ORA, wherein RA is substituted C1-10 alkyl. In some embodiments, X1 is —ORA, wherein RA is unsubstituted aryl. In some embodiments, X1 is —ORA, wherein RA is substituted aryl. In some embodiments, X1 is —ORA, wherein RA is unsubstituted acyl. In some embodiments, X1 is —ORA, wherein RA is substituted acyl. In some embodiments, X1 is —ORA, wherein RA is unsubstituted imidoyl. In some embodiments, X1 is —ORA, wherein RA is substituted imidoyl.

In some embodiments, X1 is —SRA. In some embodiments, X1 is —SH. In some embodiments, X1 is —S(protecting group). In some embodiments, X1 is —SRA, wherein RA is unsubstituted C1-10 alkyl. In some embodiments, X1 is —SRA, wherein RA is substituted C1-10 alkyl. In certain embodiments, X1 is —SCH3. In some embodiments, X1 is —SRA, wherein RA is unsubstituted aryl. In some embodiments, X1 is —SRA, wherein RA is substituted aryl. In some embodiments, X1 is —SRA, wherein RA is unsubstituted acyl. In some embodiments, X1 is —SRA, wherein RA is substituted acyl. In some embodiments, X1 is —SRA, wherein RA is unsubstituted imidoyl. In some embodiments, X1 is —SRA, wherein RA is substituted imidoyl.

In some embodiments, X1 is C1-10 alkoxy. In some embodiments, X1 is C1-3 alkoxy.

In some embodiments, X1 is selected from the group consisting of alpha-thiomethyl, beta-thiomethyl, alpha-thiocresyl, beta-thiocresyl, alpha-t-butyldiphenylsilyloxy, beta-t-butyldiphenylsilyloxy, and alpha-methoxy.

In some embodiments, R1 is —N3 or —N(RW)2, wherein each RW is independently hydrogen or a nitrogen protecting group. In certain embodiments, R1 is —N3. In certain embodiments, R1 is —N(RW)2, wherein each RW is independently hydrogen or a nitrogen protecting group. In certain embodiments, R1 is —NH2. In certain embodiments, R1 is —NHRW, wherein RW is a nitrogen protecting group. In certain embodiments, R1 is —N(RW)2, wherein each RW is a nitrogen protecting group. In certain embodiments, R1 is selected from the group consisting of —N3, —NH(Cbz), —NH(Boc), —NH(Fmoc), —NHC(O)CCl3, —NHC(O)CH3, and —N(C(O)CH3)2. In certain embodiments, R1 is —NH(Cbz). In certain embodiments, R1 is —NH(Fmoc). In certain embodiments, R1 is —NHC(O)CCl3. In certain embodiments, R1 is —NHC(O)CH3. In certain embodiments, R1 is —N(C(O)CH3)2.

In some embodiments, R2 is —N3 or —N(RW)2, wherein each RW is independently hydrogen or a nitrogen protecting group. In certain embodiments, R2 is —N3. In certain embodiments, R2 is —N(RW)2, wherein each RW is independently hydrogen or a nitrogen protecting group. In certain embodiments, R2 is —NH2. In certain embodiments, R2 is —NHRW, wherein RW is a nitrogen protecting group. In certain embodiments, R2 is —N(RW)2, wherein each RW is a nitrogen protecting group. In certain embodiments, R2 is selected from the group consisting of —N3, —NH(Cbz), —NH(Boc), —NH(Fmoc), —NHC(O)CCl3, —NHC(O)CH3, and —N(C(O)CH3)2. In certain embodiments, R2 is —NH(Cbz). In certain embodiments, R2 is —NH(Fmoc). In certain embodiments, R2 is —NHC(O)CCl3. In certain embodiments, R2 is —NHC(O)CH3. In certain embodiments, R2 is —N(C(O)CH3)2.

In some embodiments, R3 is —N3 or —N(RW)2, wherein each RW is independently hydrogen or a nitrogen protecting group. In certain embodiments, R3 is —N3. In certain embodiments, R3 is —N(RW)2, wherein each RW is independently hydrogen or a nitrogen protecting group. In certain embodiments, R3 is —NH2. In certain embodiments, R3 is —NHRW, wherein RW is a nitrogen protecting group. In certain embodiments, R3 is —N(RW)2, wherein each RW is a nitrogen protecting group. In certain embodiments, R3 is selected from the group consisting of —N3, —NH(Cbz), —NH(Boc), —NH(Fmoc), —NHC(O)CCl3, —NHC(O)CH3, and —N(C(O)CH3)2. In certain embodiments, R3 is —NH(Cbz). In certain embodiments, R3 is —NH(Fmoc). In certain embodiments, R3 is —NHC(O)CCl3. In certain embodiments, R3 is —NHC(O)CH3. In certain embodiments, R3 is —N(C(O)CH3)2.

In some embodiments, R4 is —N3 or —N(RW)2, wherein each RW is independently hydrogen or a nitrogen protecting group. In certain embodiments, R4 is —N3. In certain embodiments, R4 is —N(RW)2, wherein each RW is independently hydrogen or a nitrogen protecting group. In certain embodiments, R4 is —NH2. In certain embodiments, R4 is —NHRW, wherein RW is a nitrogen protecting group. In certain embodiments, R4 is —N(RW)2, wherein each RW is a nitrogen protecting group. In certain embodiments, R4 is selected from the group consisting of —N3, —NH(Cbz), —NH(Boc), —NH(Fmoc), —NHC(O)CCl3, —NHC(O)

CH3, and —N(C(O)CH3)2. In certain embodiments, R4 is —NH(Cbz). In certain embodiments, R4 is —NH(Fmoc). In certain embodiments, R4 is —NHC(O)CCl3. In certain embodiments, R4 is —NHC(O)CH3. In certain embodiments, R4 is —N(C(O)CH3)2.

In some embodiments, R5 is —N3 or —N(RW)2, wherein each RW is independently hydrogen or a nitrogen protecting group. In certain embodiments, R5 is —N3. In certain embodiments, R5 is —N(RW)2, wherein each RW is independently hydrogen or a nitrogen protecting group. In certain embodiments, R5 is —NH2. In certain embodiments, R5 is —NHRW, wherein RW is a nitrogen protecting group. In certain embodiments, R5 is —N(RW)2, wherein each RW is a nitrogen protecting group. In certain embodiments, R5 is selected from the group consisting of —N3, —NH(Cbz), —NH(Boc), —NH(Fmoc), —NHC(O)CCl3, —NHC(O)CH3, and —N(C(O)CH3)2. In certain embodiments, R5 is —NH(Cbz). In certain embodiments, R5 is —NH(Fmoc). In certain embodiments, R5 is —NHC(O)CCl3. In certain embodiments, R5 is —NHC(O)CH3. In certain embodiments, R5 is —N(C(O)CH3)2.

In some embodiments, R6 is —N3 or —N(RW)2, wherein each RW is independently hydrogen or a nitrogen protecting group. In certain embodiments, R6 is —N3. In certain embodiments, R6 is —N(RW)2, wherein each RW is independently hydrogen or a nitrogen protecting group. In certain embodiments, R6 is —NH2. In certain embodiments, R6 is —NHRW, wherein RW is a nitrogen protecting group. In certain embodiments, R6 is —N(RW)2, wherein each RW is a nitrogen protecting group. In certain embodiments, R6 is selected from the group consisting of —N3, —NH(Cbz), —NH(Boc), —NH(Fmoc), —NHC(O)CCl3, —NHC(O)CH3, and —N(C(O)CH3)2. In certain embodiments, R6 is —NH(Cbz). In certain embodiments, R6 is —NH(Fmoc). In certain embodiments, R6 is —NHC(O)CCl3. In certain embodiments, R6 is —NHC(O)CH3. In certain embodiments, R6 is —N(C(O)CH3)2.

In some embodiments, R1, R2 and R3 are the same. In some embodiments, R1, R2 and R3 are —OH. In some embodiments, R4, R5 and R6 are the same. In some embodiments, R4, R5 and R6 are —OH.

In certain embodiments, L is —OH.
In certain embodiments, L is —OH and R1 is —N3. In certain embodiments, L is —OH, R1 is —N3, and each instance of R2, R3, R4, R5 and R6 is —OH.
In certain embodiments, L is —OH and R2 is —N3. In certain embodiments, L is —OH, R2 is —N3, and each instance of R1, R3, R4, R5 and R6 is —OH.
In certain embodiments, L is —OH and R3 is —N3. In certain embodiments, L is —OH, R3 is —N3, and each instance of R1, R2, R4, R5 and R6 is —OH.
In certain embodiments, L is —OH and R4 is —N3. In certain embodiments, L is —OH, R4 is —N3, and each instance of R1, R2, R3, R5 and R6 is —OH.
In certain embodiments, L is —OH and R5 is —N3. In certain embodiments, L is —OH, R5 is —N3, and each instance of R1, R2, R3, R4 and R6 is —OH.
In certain embodiments, L is —OH and R6 is —N3. In certain embodiments, L is —OH, R6 is —N3, and each instance of R1, R2, R3, R4 and R5 is —OH.
In certain embodiments, each instance of R1, R2, R3, R4, R5, R6 and L is —F. In certain embodiments, R1 is —F. In certain embodiments, R2 is —F. In certain embodiments, R3 is —F. In certain embodiments, R4 is —F. In certain embodiments, R5 is —F. In certain embodiments, R6 is —F. In certain embodiments, L is —F.

In certain embodiments, L is of the following structure:

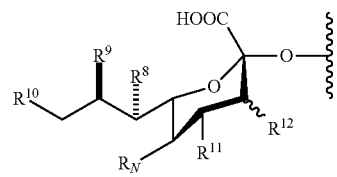

wherein:
each instance of R8, R9, R10 and R11 is independently selected from hydrogen, halogen, optionally substituted alkyl, optionally substituted alkenyl, optionally substituted alkynyl, optionally substituted heterocyclyl, optionally substituted aryl, —N3, —NO2, —N(RB)2, —N(RA)C(O)RA, —ORA, —OC(O)RA, —SRA, —C(O)N(RB)2, —CN, —C(O)RA, —C(O)ORA, —S(O)RA, —SO2RA, —SO2N(RB)2, and —NHSO2RB;
RN is selected from —N3, —NO2, —N(RB)2, —N(RA)C(O)RA, —ORA, —OC(O)RA, —SRA, —C(O)N(RB)2, —CN, —C(O)RA, —C(O)ORA, —S(O)RA, —SO2RA, —SO2N(RB)2, and —NHSO2RB;
each instance of RA is independently selected from hydrogen, optionally substituted alkyl, optionally substituted alkenyl, optionally substituted alkynyl, optionally substituted heterocyclyl, and optionally substituted aryl; and
each instance of RB is independently selected from hydrogen, optionally substituted alkyl, optionally substituted alkenyl, optionally substituted alkynyl, optionally substituted heterocyclyl, and optionally substituted aryl.

In some embodiments, the compound is of Formula (II)

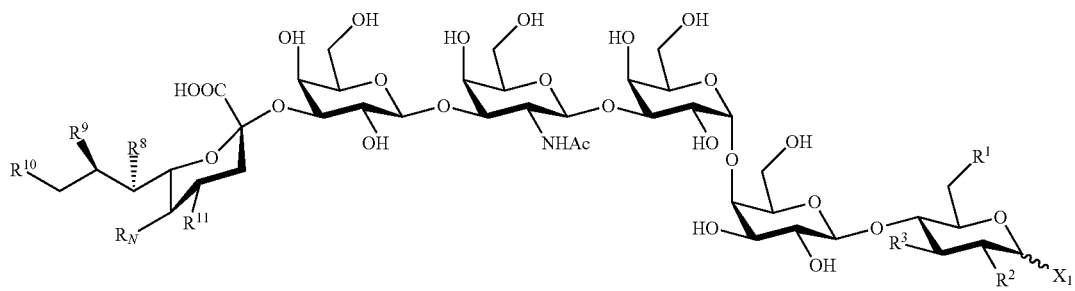

(II)
wherein: R1, R2, R3, R8, R9, R10, R11 and RN and X1 are as described herein, and
provided the compound is not of the formula:

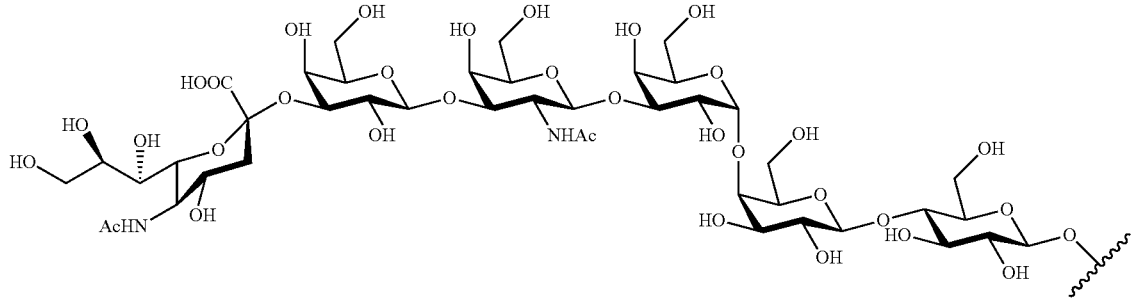

In some embodiments, R8 is —N3 or —N(RW)2, wherein each RW is independently hydrogen or a nitrogen protecting group. In certain embodiments, R8 is —N3. In certain embodiments, R8 is —N(RW)2, wherein each RW is independently hydrogen or a nitrogen protecting group. In certain embodiments, R8 is —NH2. In certain embodiments, R8 is —NHRW, wherein RW is a nitrogen protecting group. In certain embodiments, R8 is —N(RW)2, wherein each RW is a nitrogen protecting group. In certain embodiments, R8 is selected from the group consisting of —N3, —NH(Cbz), —NH(Boc), —NH(Fmoc), —NHC(O)CCl3, —NHC(O)CH3, and —N(C(O)CH3)2. In certain embodiments, R8 is —NH(Cbz). In certain embodiments, R8 is —NH(Fmoc). In certain embodiments, R8 is —NHC(O)CCl3. In certain embodiments, R8 is —NHC(O)CH3. In certain embodiments, R8 is —N(C(O)CH3)2.

In some embodiments, R9 is —N3 or —N(RW)2, wherein each RW is independently hydrogen or a nitrogen protecting group. In certain embodiments, R9 is —N3. In certain embodiments, R9 is —N(RW)2, wherein each RW is independently hydrogen or a nitrogen protecting group. In certain embodiments, R9 is —NH2. In certain embodiments, R9 is —NHRW, wherein RW is a nitrogen protecting group. In certain embodiments, R9 is —N(RW)2, wherein each RW is a nitrogen protecting group. In certain embodiments, R9 is selected from the group consisting of —N3, —NH(Cbz), —NH(Boc), —NH(Fmoc), —NHC(O)CCl3, —NHC(O)CH3, and —N(C(O)CH3)2. In certain embodiments, R9 is —NH(Cbz). In certain embodiments, R9 is —NH(Fmoc). In certain embodiments, R9 is —NHC(O)CCl3. In certain embodiments, R9 is —NHC(O)CH3. In certain embodiments, R9 is —N(C(O)CH3)2.

In some embodiments, R10 is —N3 or —N(RW)2, wherein each RW is independently hydrogen or a nitrogen protecting group. In certain embodiments, R10 is —N3. In certain embodiments, R10 is —N(RW)2, wherein each RW is independently hydrogen or a nitrogen protecting group. In certain embodiments, R10 is —NH2. In certain embodiments, R10 is —NHRW, wherein RW is a nitrogen protecting group. In certain embodiments, R10 is —N(RW)2, wherein each RW is a nitrogen protecting group. In certain embodiments, R10 is selected from the group consisting of —N3, —NH(Cbz), —NH(Boc), —NH(Fmoc), —NHC(O)CCl3, —NHC(O)CH3, and —N(C(O)CH3)2. In certain embodiments, R10 is —NH(Cbz). In certain embodiments, R10 is —NH(Fmoc). In certain embodiments, R10 is —NHC(O)CCl3. In certain embodiments, R10 is —NHC(O)CH3. In certain embodiments, R10 is —N(C(O)CH3)2.

In some embodiments, R11 is —N3 or —N(RW)2, wherein each RW is independently hydrogen or a nitrogen protecting group. In certain embodiments, R11 is —N3. In certain embodiments, R11 is —N(RW)2, wherein each RW is independently hydrogen or a nitrogen protecting group. In certain embodiments, R11 is —NH2. In certain embodiments, R11 is —NHRW, wherein RW is a nitrogen protecting group. In certain embodiments, R11 is —N(RW)2, wherein each RW is a nitrogen protecting group. In certain embodiments, R11 is selected from the group consisting of —N3, —NH(Cbz), —NH(Boc), —NH(Fmoc), —NHC(O)CCl3, —NHC(O)CH3, and —N(C(O)CH3)2. In certain embodiments, R11 is —NH(Cbz). In certain embodiments, R11 is —NH(Fmoc). In certain embodiments, R11 is —NHC(O)CCl3. In certain embodiments, R11 is —NHC(O)CH3. In certain embodiments, R11 is —N(C(O)CH3)2.

In some embodiments, R12 is —N3 or —N(RW)2, wherein each RW is independently hydrogen or a nitrogen protecting group. In certain embodiments, R12 is —N3. In certain embodiments, R12 is —N(RW)2, wherein each RW is independently hydrogen or a nitrogen protecting group. In certain embodiments, R12 is —NH2. In certain embodiments, R12 is —NHRW, wherein RW is a nitrogen protecting group. In certain embodiments, R12 is —N(RW)2, wherein each RW is a nitrogen protecting group. In certain embodiments, R12 is selected from the group consisting of —N3, —NH(Cbz), —NH(Boc), —NH(Fmoc), —NHC(O)CCl3, —NHC(O)CH3, and —N(C(O)CH3)2. In certain embodiments, R12 is —NH(Cbz). In certain embodiments, R12 is —NH(Fmoc). In certain embodiments, R12 is —NHC(O)CCl3. In certain embodiments, R12 is —NHC(O)CH3. In certain embodiments, R12 is —N(C(O)CH3)2.

In some embodiments, RN is —N3 or —N(RW)2, wherein each RW is independently hydrogen or a nitrogen protecting group. In certain embodiments, RN is —N3. In certain embodiments, RN is —N(RW)2, wherein each RW is independently hydrogen or a nitrogen protecting group. In certain embodiments, RN is —NH2. In certain embodiments, RN is —NHRW, wherein RW is a nitrogen protecting group. In certain embodiments, RN is —N(RW)2, wherein each RW is a nitrogen protecting group. In certain embodiments, RN is selected from the group consisting of —N3, —NH(Cbz), —NH(Boc), —NH(Fmoc), —NHC(O)CCl3, —NHC(O)CH3, and —N(C(O)CH3)2. In certain embodiments, RN is —NH(Cbz). In certain embodiments, RN is —NH(Fmoc). In certain embodiments, RN is —NHC(O)CCl3. In certain embodiments, RN is —NHC(O)CH3. In certain embodiments, RN is —N(C(O)CH3)2.

Immunogenic Compositions

In another aspect, the present invention provides an immunogenic composition, comprising (a) a glycan conjugate including a carrier and one or more glycans, and optionally (b) an adjuvant, wherein: each of the one or more glycans is conjugated with the carrier through a linker, having the formula (III) or (IV):

(III)
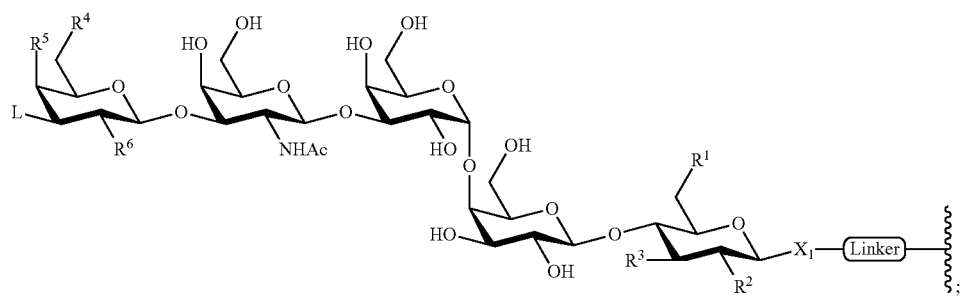

(IV)
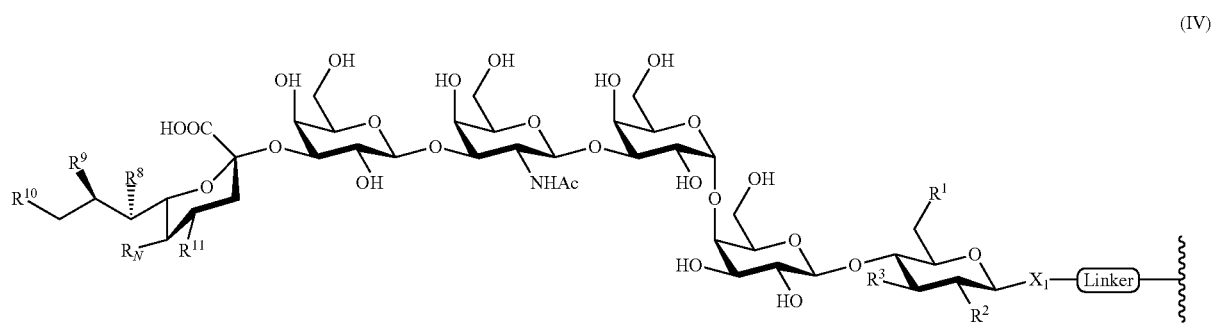

wherein X1, R1, R2, R3, R4, R5, R6, R8, R9, R10, R11, L and RN are as described herein.

In certain embodiments, the linker is a hetero- or homo-bifunctional linker.

In certain embodiments, the linker is a homo-bifunctional p-nitrophenyl linker.

In certain embodiments, the linker includes at least one sulfur atom, carboxylate group, amide group, carbamate group, carbonate group, thiocarbamate group, thiocarbonate group, thioether group, succinamide group, n-hydroxy succinamide group, or any combination thereof.

In certain embodiments, the linker is -$L^1$-$L^2$-, wherein L1 is a bond, —O—, —S—, —NRL1a-, —C(=O)—, —NRL1aC(=O)—, —NRL1aC(=O)O—, —C(=O) NRL1a-, —OC(=O)NRL1a-, —SC(=O)—, —C(=O)S—, —OC(=O)—, —C(=O)O—, —NRL1aC(=S)—, —C(=S)NRL1a-, trans-CRL1b=CRL1b-, cis-CRL1b=CRL1b-, —C≡C—, —OC(RL1b)2-, —C(RL1b)2O—, —NRL1aC(RL1b)2-, —C(RL1b)2NRL1a-, —SC(RL1b)2-, —C(RL1b)2S—, —S(=O)2O—, —OS(=O)2-, —S(=O)2NRL1a-, —NRL1aS(=O)2-, or an optionally substituted C1-20 hydrocarbon chain, optionally wherein one or more carbon units of the hydrocarbon chain is replaced with —O—, —S—, —NRL1a-, —C(=O)—, NRL1aC(=O)—, —NRL1aC(=O)O—, —C(=O) NRL1a-, —OC(=O)NRL1a-, —SC(=O)—, —C(=O) S—, —OC(=O)—, —C(=O)O—, —NRL1aC(=S)—, —C(=S)NRL1a-, trans-CRL1b=CRL1b-, cis-CRL1b=CRL1b , —C≡C—, —S(=O)2O—, —OS(=O)2-, —S(=O)2NRL1a-, or —NRL1aS(=O)2-, wherein RL1a is hydrogen, optionally substituted C1-6 alkyl, or a nitrogen protecting group, or RL1a is joined with the adjacent carbon atom to form an optionally substituted heterocyclic ring, and wherein each occurrence of RL1b is independently selected from the group consisting of hydrogen, halogen, optionally substituted C1-10 alkyl, optionally substituted alkenyl, optionally substituted alkynyl, optionally substituted carbocyclyl, optionally substituted heterocyclyl, optionally substituted aryl, and optionally substituted heteroaryl, or RL1b is joined with the adjacent carbon or nitrogen or oxygen atom to form an optionally substituted carbocyclic or heterocyclic ring, or two RL1b groups are joined to form an optionally substituted carbocyclic or optionally substituted heterocyclic ring; and L2 is a moiety derived from a cross-linking reagent capable of crosslinking the carrier and L1.

The carrier can be a protein, a lipid, a lipolized protein, a virus, a peptide, or a dendrimer of glycopeptides. In certain embodiments, the carrier is a peptide comprising a T cell epitope.

Examples of carrier proteins which may be used in the present invention are tetanus toxoid (TT), diphtheria toxoid (DT), diphtheria toxin cross-reacting material 197 (CRM197), fragment C of TT, Keyhole limpet hemocyanin (KLH), bovine serum albumin (BSA), protein D, outer-membrane protein (OMP) and pneumolysin, diphtheria toxin cross-reacting material 197 (CRM197) or other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described in the art.

In certain embodiments, the glycan conjugate is of the formula (IV-a) or (IV-b):

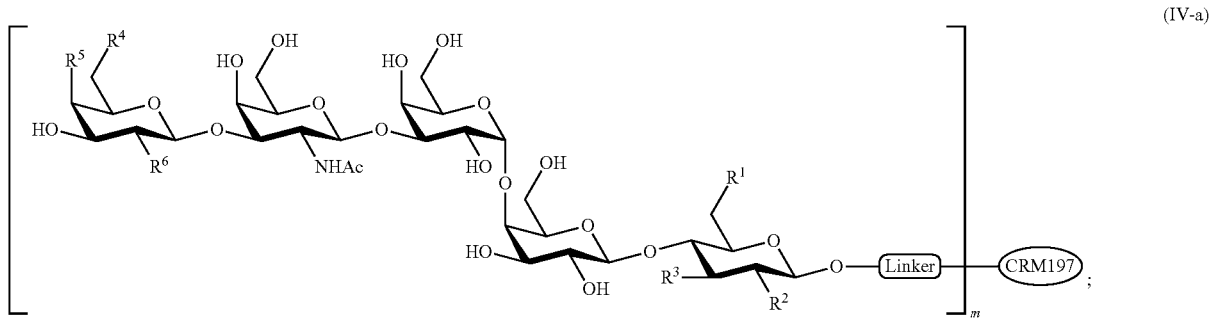

(IV-a)

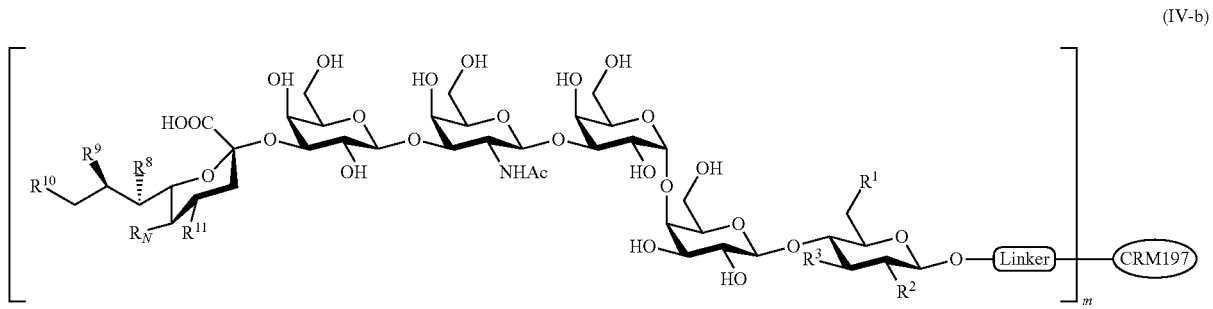

(IV-b)

wherein m is an integer of 1 to 40, inclusive.

In certain embodiments, m is an integer of 1 to 30, inclusive. As generally defined herein, m is an integer of 1 to 20 inclusive. In certain embodiments, m is 1. In certain embodiments, m is 2. In certain embodiments, m is 4. In certain embodiments, m is 6. In certain embodiments, m is 8. In certain embodiments, m is 10. In certain embodiments, m is 15. In certain embodiments, m is 20. In certain embodiments, m is 30. In certain embodiments, m is 40.

In another aspect, the present invention provides a glycan conjugate mixture comprising at least two of the glycan conjugates as described herein. In certain embodiments, the average value of w in the glycan mixture is from about 1.0 to about 40.0. In certain embodiments, the average value of w in the glycan mixture is from about 1.0 to 10.0. In certain embodiments, the average value of w in the glycan mixture is about 5.7, 4.9, 2.9, 2.8, or 3.1. In certain embodiments, the average value of w in the glycan mixture is about 4.9, 2.9, 2.8, or 3.1.

In certain embodiments, the immunogenic compositions described herein include an immunogenically effective amount of a glycan conjugate of the invention. In certain embodiments, the immunogenic composition includes a pharmaceutically effective amount of the inventive glycan conjugate.

The compounds of the invention can be synthesized using procedures described herein and also see US20140051127.

The immunogenic conjugate of the invention may include one or more molecules (e.g., 1-40, 1-20, 1-25, 1-30,) of the same or different SSEA3 and/or SSEA4 analogs and/or related derivatives. Additional descriptions and related procedures for generating glycan conjugates are described below. Also see U.S. Pat. No. 8,268,969. The contents of which is hereby incorporated by reference.

In certain embodiments, the immunogenic composition of the invention may include one or more adjuvants. Suitable adjuvants can include, for example, C34, 7DW8-5, C17, C23, C-30, alpha-galactoceramide, Gluco-C34, Aluminum salt, Squalene, MF59, and QS-21).

As used herein, the term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

As used herein, the term "immunologic adjuvant" refers to a substance used in conjunction with an immunogen which enhances or modifies the immune response to the immunogen. The α-GalCer analogs of the present disclosure are used as immunologic adjuvants to modify or augment the effects of a vaccine by stimulating the immune system of a patient who is administered the vaccine to respond to the vaccine more vigorously. In an exemplary implementation, the analog C34 is used as an adjuvant. The structures of C34 and other alpha-galactosyl ceramide analogs and their use as adjuvants are disclosed in detail in U.S. Pat. No. 7,928,077.

As used herein, the term "glycolipid" refers to a carbohydrate-attached lipid that serves as a marker for cellular recognition.

The glycolipids C34, Gluco-C34, C23 and 7DW8-5 have the following structures:

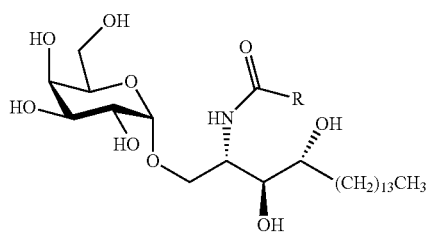
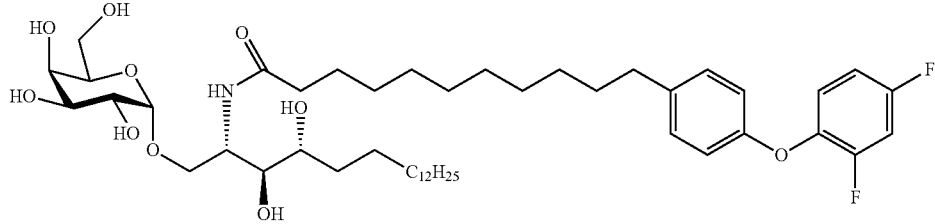
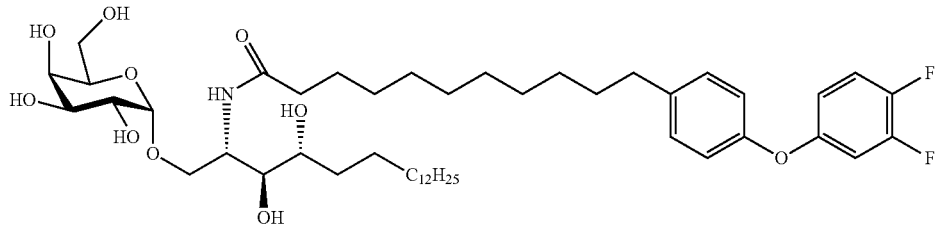

C34

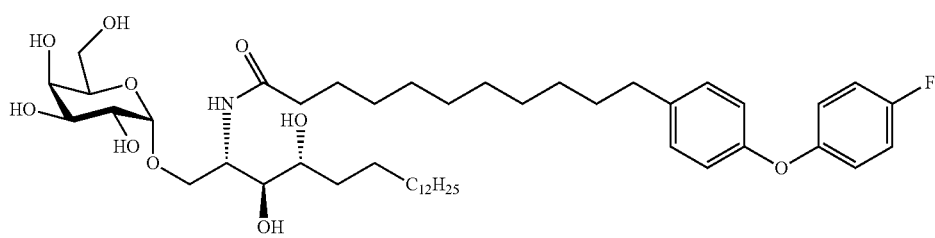

Gluco-C34

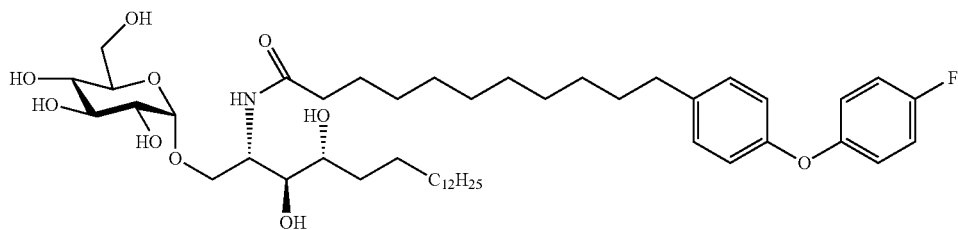

C1, R = (CH2)24CH3 C23, R = (CH2)7PhF C34, R = (CH2)10PhOPhF 7DW8-5, R = (CH2)10PhF

The immunogenic composition can further include a pharmaceutically acceptable excipient. In certain embodiments, the immunogenic compositions described herein include a pharmaceutically effective amount of a glycan conjugate of the invention.

In another aspect, the present invention provides a cancer vaccine comprising an immunogenic composition described herein and a pharmaceutically acceptable excipient.

The cancer vaccines of the invention may include a single dose or multiple doses of the inventive glycan conjugates, a glycan conjugate mixture thereof, or immunogenic compositions thereof. The provided cancer vaccines may be useful for treating or reducing the risk of cancers. The cancer vaccines may also include packaging information describing the use or prescribing information for the subject or a health care professional. Such information may be required by a regulatory agency such as the U.S. Food and Drug Administration (FDA). The cancer vaccine may also optionally include a device for administration of the compound or composition, for example, a syringe for parenteral administration.

Pharmaceutical Formulations

The immune composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage of the vaccine may also depend on the route of administration and varies according to the size of the host.

The immune composition of this invention can also be used to generate antibodies in animals for production of antibodies, which can be used in both cancer treatment and diagnosis. Methods of making monoclonal and polyclonal antibodies and fragments thereof in animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab')2, Fv, scFv (single chain antibody), and dAb (domain antibody; Ward, et. al. (1989) Nature, 341, 544).

The compositions disclosed herein can be included in a pharmaceutical composition together with additional active agents, carriers, vehicles, excipients, or auxiliary agents identifiable by a person skilled in the art upon reading of the present disclosure.

The pharmaceutical compositions preferably comprise at least one pharmaceutically acceptable carrier. In such pharmaceutical compositions, the compositions disclosed herein form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Clinical Applications

The present invention provides glycan conjugates, immunogenic compositions or vaccines useful for the treatment of a proliferative disease such as cancer (e.g. lung cancer, large bowel cancer, pancreas cancer, biliary tract cancer, or endometrial cancer), benign neoplasm, or angiogenesis in a subject.

The immunogenic compositions or vaccines described herein can also be used to generate antibodies in human or animals for production of antibodies, which can be used in both cancer treatment and diagnosis. In some embodiments, the immunogenic compositions or vaccines described herein can also be used to generate the production of GloboH, SSEA3 and/or SSEA4 antibodies. Methods of making monoclonal and polyclonal antibodies and fragments thereof in human and/or animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab').sub.2, Fv, scFv (single chain antibody), and dAb (domain antibody; Ward, et. al. (1989) Nature, 341, 544).

Compositions comprising at least one anti-SSEA3/SSEA4/GloboH antibody or at least one polynucleotide comprising sequences encoding an anti-SSEA3/SSEA4/GloboH antibody are provided. In certain embodiments, a composition may be a pharmaceutical composition. As used herein, compositions comprise one or more antibodies that bind to one or more SSEA3/SSEA4/GloboH and/or one or more polynucleotides comprising sequences encoding one or more antibodies that bind to one or more SSEA3/SSEA4/GloboH. These compositions may further comprise suitable carriers, such as pharmaceutically acceptable excipients including buffers, which are well known in the art.

Isolated antibodies and polynucleotides are also provided. In certain embodiments, the isolated antibodies and polynucleotides are substantially pure.

In one embodiment, anti-SSEA3/SSEA4/GloboH antibodies are monoclonal. In another embodiment, fragments of the anti-SSEA3/SSEA4/GloboH antibodies (e.g., Fab, Fab' —SH and F(ab')2 fragments) are provided. These antibody fragments can be created by traditional means, such as enzymatic digestion, or may be generated by recombinant techniques. Such antibody fragments may be chimeric, humanized, or human. These fragments are useful for the diagnostic and therapeutic purposes set forth below.

Pharmaceutical Formulations

Therapeutic formulations comprising an pharmaceutical agents of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thiol-disulfide interchange, stabilization may be achieved by modifying sulfhydryl residues, lyophilizing from acidic solutions, controlling moisture content, using appropriate additives, and developing specific polymer matrix compositions.

Pharmaceutical compositions of the invention can be used to treat, inhibit, delay progression of, prevent/delay recurrence of, ameliorate, or prevent diseases, disorders or conditions associated with abnormal expression and/or activity of SSEA3/SSEA4/GloboHs and SSEA3/SSEA4/GloboH related proteins, including but not limited to cancer, muscular disorders, ubiquitin-pathway-related genetic disorders, immune/inflammatory disorders, neurological disorders, and other ubiquitin pathway-related disorders.

In one aspect, a blocking antibody of the invention is specific for a SSEA3/SSEA4/GloboH.

Pharmaceutical compositions of the invention can be used either alone or in combination with other compositions in a therapy. For instance, an antibody of the invention may be co-administered with another antibody, and/or adjuvant/therapeutic agents (e.g., steroids). For instance, an antibody of the invention may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the antibody of the invention can occur prior to, and/or following, administration of the adjunct therapy or therapies.

Pharmaceutical compositions of the invention (and adjunct therapeutic agent) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the Pharmaceutical composition can be suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. Intracellular expression of an intrabody is effected by introducing a nucleic acid encoding the desired antibody or antigen-binding portion thereof (lacking the wild-type leader sequence and secretory signals normally associated with the gene encoding that antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

Pharmaceutical compositions of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an Pharmaceutical compositions of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

In some embodiments, the provided glycan conjugates, immunogenic compositions or vaccines are useful in treating, or diagnosing a cancer, including, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva). In certain embodiments, the provided glycan conjugates, immunogenic compositions or vaccines are useful for treating brain cancer, lung cancer, breast cancer, oral cancer, esophagus cancer, stomach cancer, liver cancer, bile duct cancer, pancreas cancer, colon cancer, kidney cancer, bone cancer, skin cancer, cervix cancer, ovary cancer, and prostate cancer.

To perform the treatment methods described herein, an effective amount of any of the glycan conjugates or immunogenic compositions or vaccines described herein may be administered to a subject in need of the treatment via a suitable route, as described above. The subject, such as a human subject, can be a patient having cancer, suspected of having cancer, or susceptible to cancer. The amount of the glycan conjugate or immunogenic composition administered to the subject may be effective in eliciting immune responses specific to the glycan moiety in the conjugate or composition. In some embodiments, the amount of the glycan conjugate or immunogenic composition is sufficient to elicit immune responses leading to the inhibition of cancer growth and/or reduction of tumor mass. In other embodiments, the amount of the glycan conjugate or immunogenic composition may be effective in delaying the onset of the target cancer or reducing the risk for developing the cancer. The exact amount of the provided glycan conjugates, immunogenic compositions or vaccines required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of the provided glycan conjugates, immunogenic compositions or vaccines for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the provided glycan conjugates, immunogenic compositions or vaccines may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of the provided glycan conjugates, immunogenic compositions or vaccines to an adult. The amount to be administered to, for example, a child or an adolescent can be determined by a medical practitioner or person skilled in the art and can be lower or the same as that administered to an adult.

It will be also appreciated that the provided glycan conjugates, immunogenic compositions or vaccines can be administered in combination with one or more additional therapeutically active agents. The provided glycan conjugates, immunogenic compositions or vaccines can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The provided glycan conjugates, immunogenic compositions or vaccines can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In certain embodiments, the provided glycan conjugate, immunogenic composition or vaccine is administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Syntheses of SSEA3 Analogues

A: Chemo-enzymatic Synthesis of SSEA3 Analog-NH2

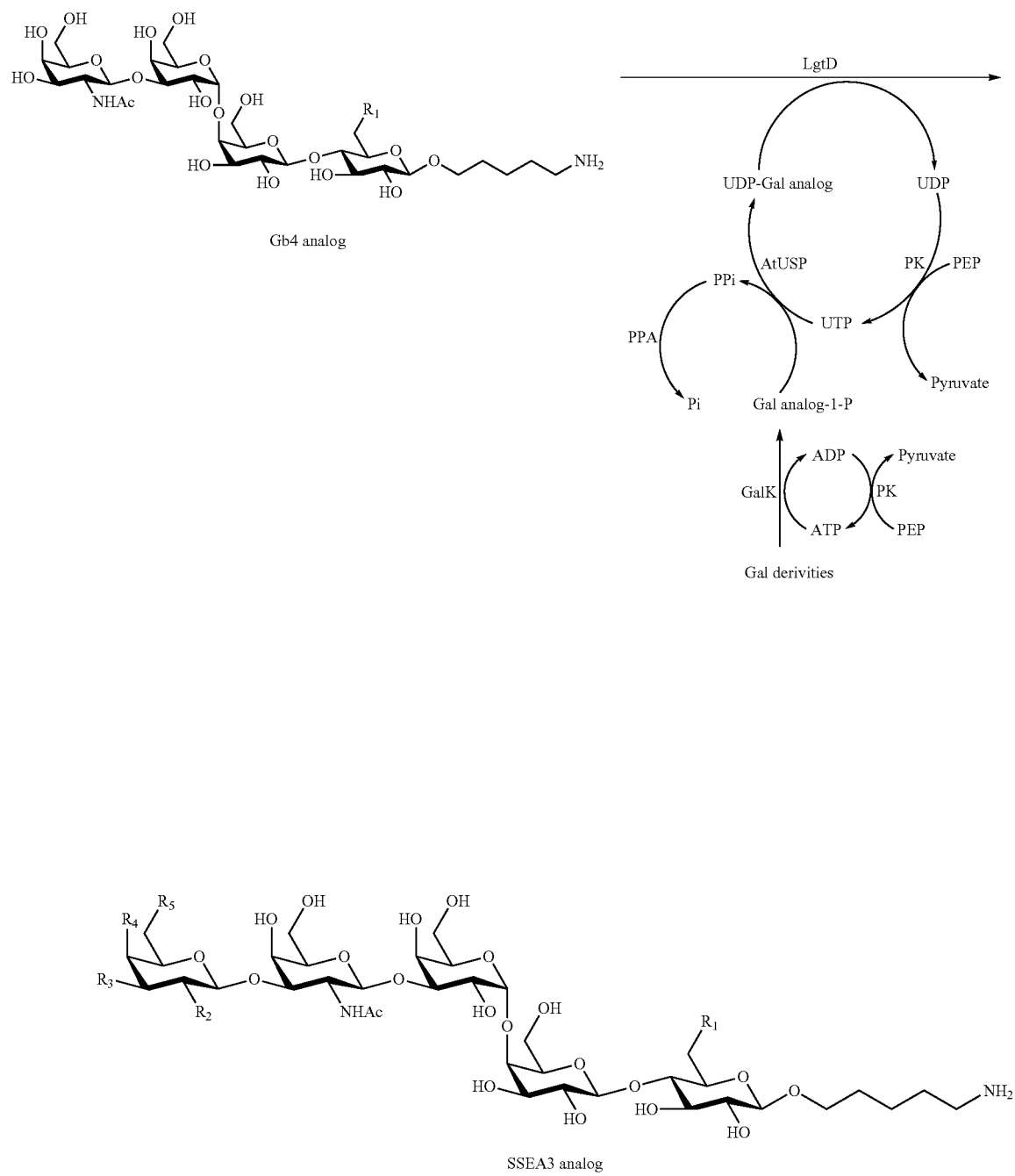

The combined compounds Gb4 analog, ATP, UTP, galactose analog, phosphoenolpyruvate, $MgCl_2$ with enzymes galactokinase (GalK), UDP-sugar pyrophosphorylase (AtUSP), beta-1,3-galactosyltransferase (LgtD,), pyruvate kinase (PK), and inorganic pyrophosphatase (PPA) in the solution, and the reaction was initiated at room temperature with the pH controlled at 7.0, and the reaction was monitored by TLC until no more product could be observed. After completion of the reaction, the proteins in the reaction mixture were removed by heating for 30 min followed by centrifugation and filtration with 0.22 µM filter. The filtrate was then purified by C-18 gel chromatography. Fractions were collected and monitored by TLC.

Example 2
Exemplary Syntheses of SSEA4 Analogues
A: Chemical Synthesis of SSEA4-Gc-NH2
Scheme 2: Synthesis SSEA4-Gc-NH2 by chemical synthesis
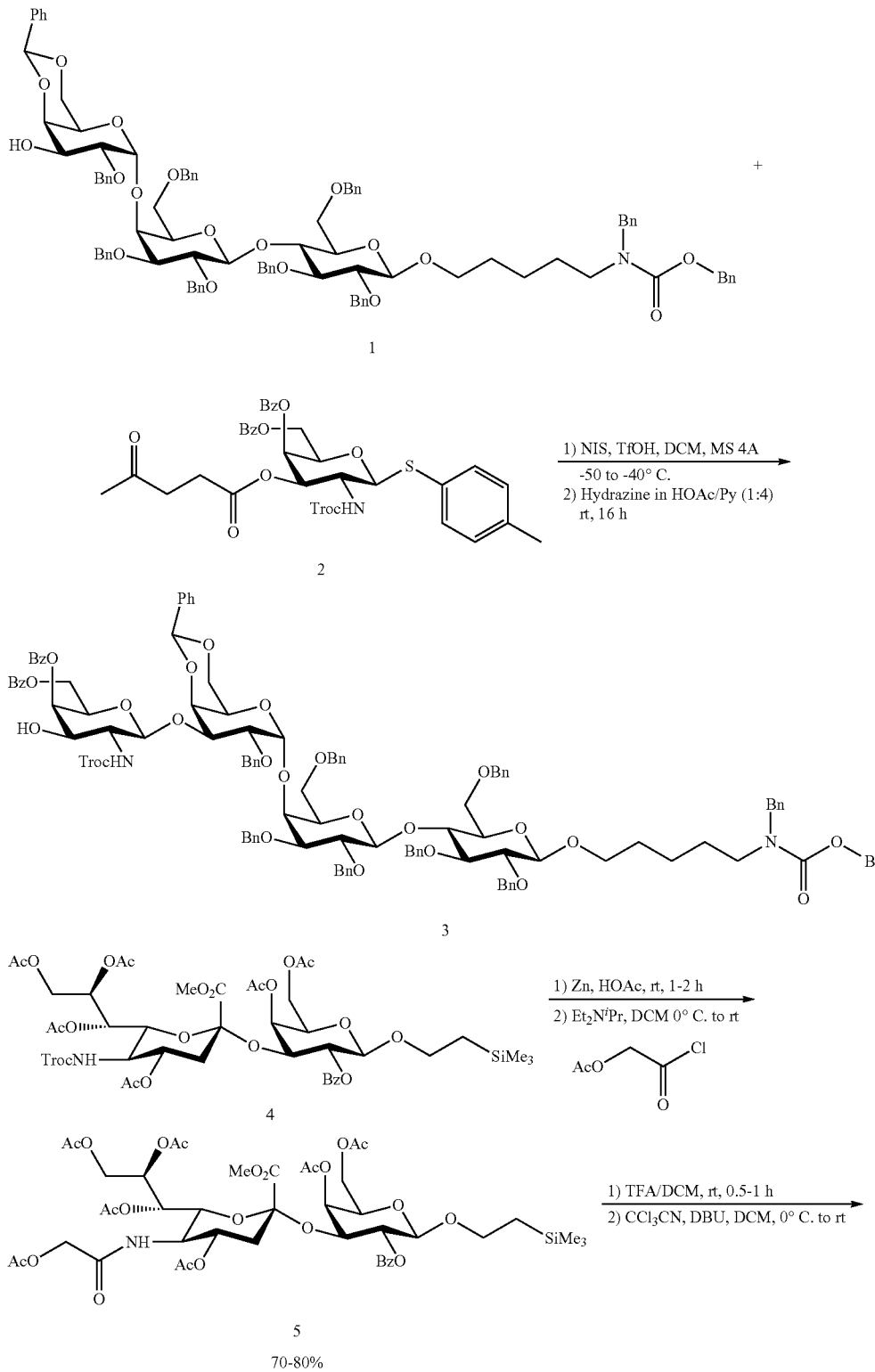

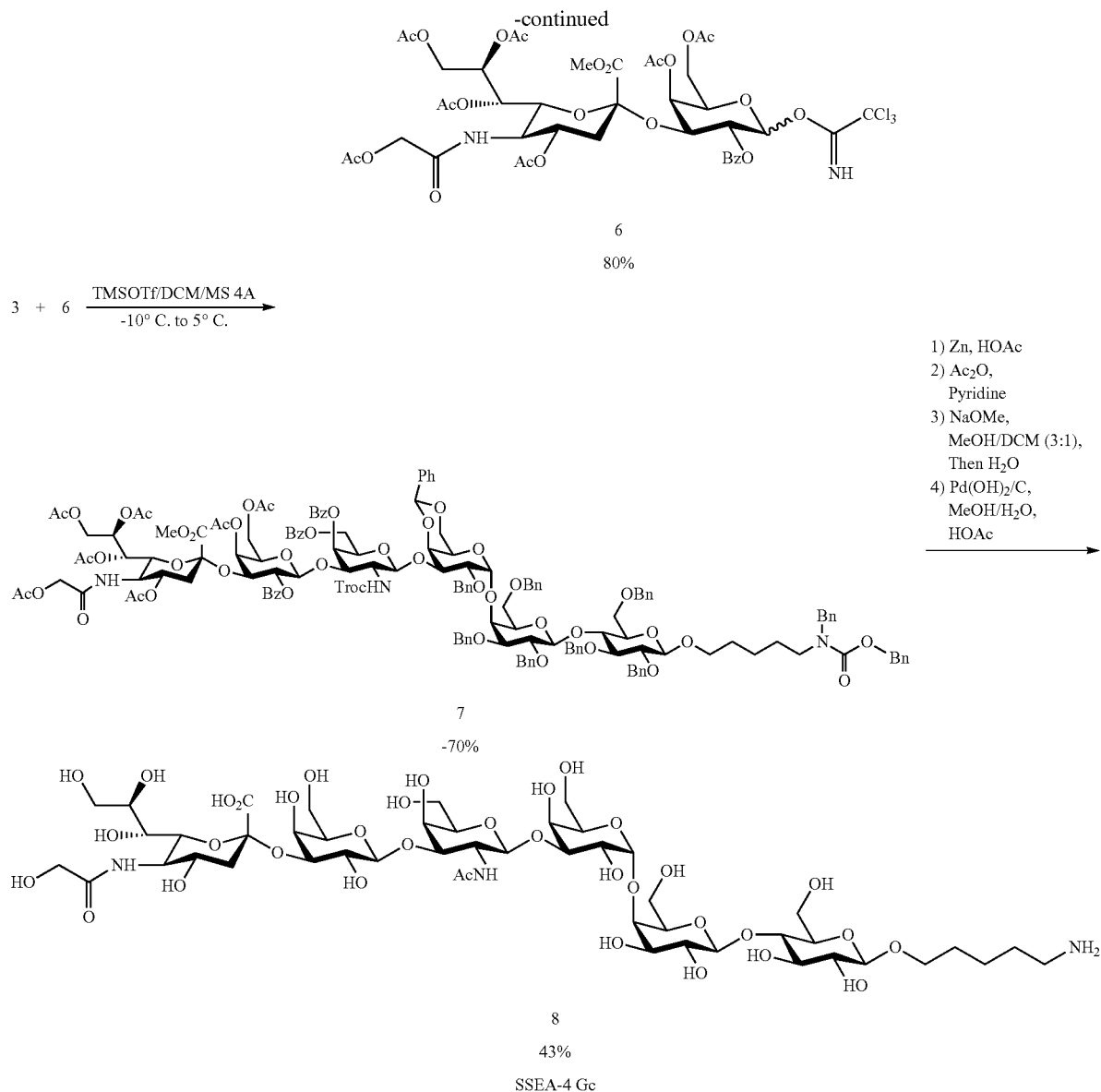

Powdered molecular sieves (4 A, 0.5 g) was added to a solution of acceptor 3 (93 mg, 0.045 mmol) and imidates 6 (76 mg, 0.068 mmol) in 6 mL of dichloromethane ($CH_2Cl_2$). The mixture was stirred at room temperature for 2 hrs. After cooled to −10° C., TMSOTf (5 µL, 0.03 mmol) was added, and the mixture was stirred at 5° C. (cold room) overnight. The reaction mixture was quenched by the addition of triethylamine (0.5 mL), diluted with $CH_2Cl_2$ and filtered through a pad of celite. The filtrate was washed with saturated sodium bicarbonate ($NaHCO_3$) aqueous solution, dried over sodium sulfate ($Na_2SO_4$), filtered, and concentrated. The residue was purified by flash silica gelchromatography (50-100% EtOAc in Hexane) to afford hexasaccharide 7 contaminated with impurities from disaccharide imidates 6. The yield was determined by NMR (90 mg, 68%).

Zinc dust (1 g) was added to a solution of hexasaccharide 7 (90 mg, 0.03 mmol) in glacial acetic acid (5.0 mL) and the mixture was stirred for 1-2 hrs, until compound 7 was consumed by TLC analysis. The reaction mixture was diluted with $CH_2Cl_2$, filtered through a pad of celite, and concentrated under reduced pressure. The residue was dissolved in pyridine/$Ac_2O$ (1:1, 2.0 mL), stirred for 1 h, and concentrated. The residue was purified by flash silica gel chromatography. The acylated material was dissolved in anhydrous $CH_2Cl_2$ and MeOH (2:8, 10 mL) and treated with NaOMe (45 mg). After stirring at room temperature for 4 hrs, water (0.2 mL) was added, and the resulting mixture was stirred for 16 hrs. The reaction mixture was neutralized with amberlyst IR-120, filtered, and concentrated. The residue was purified by reverse phase chromatography (RP-18).

Palladium hydroxide (20% in Charcoal, 50 mg) was added to the adduct in a mixture of methanol/water/Acetic acid (10:10:0.5, 6 mL) and the reaction mixture was stirred at room temperature under a positive pressure of hydrogen for 16 hrs. The reaction mixture was filtered through a pad of celite and concentrated. The residue was purified by reverse phase chromatography to afford 8 (17 mg, 43%).

B: Chemoenzymatic Synthesis of SSEA4 Analog-NH2

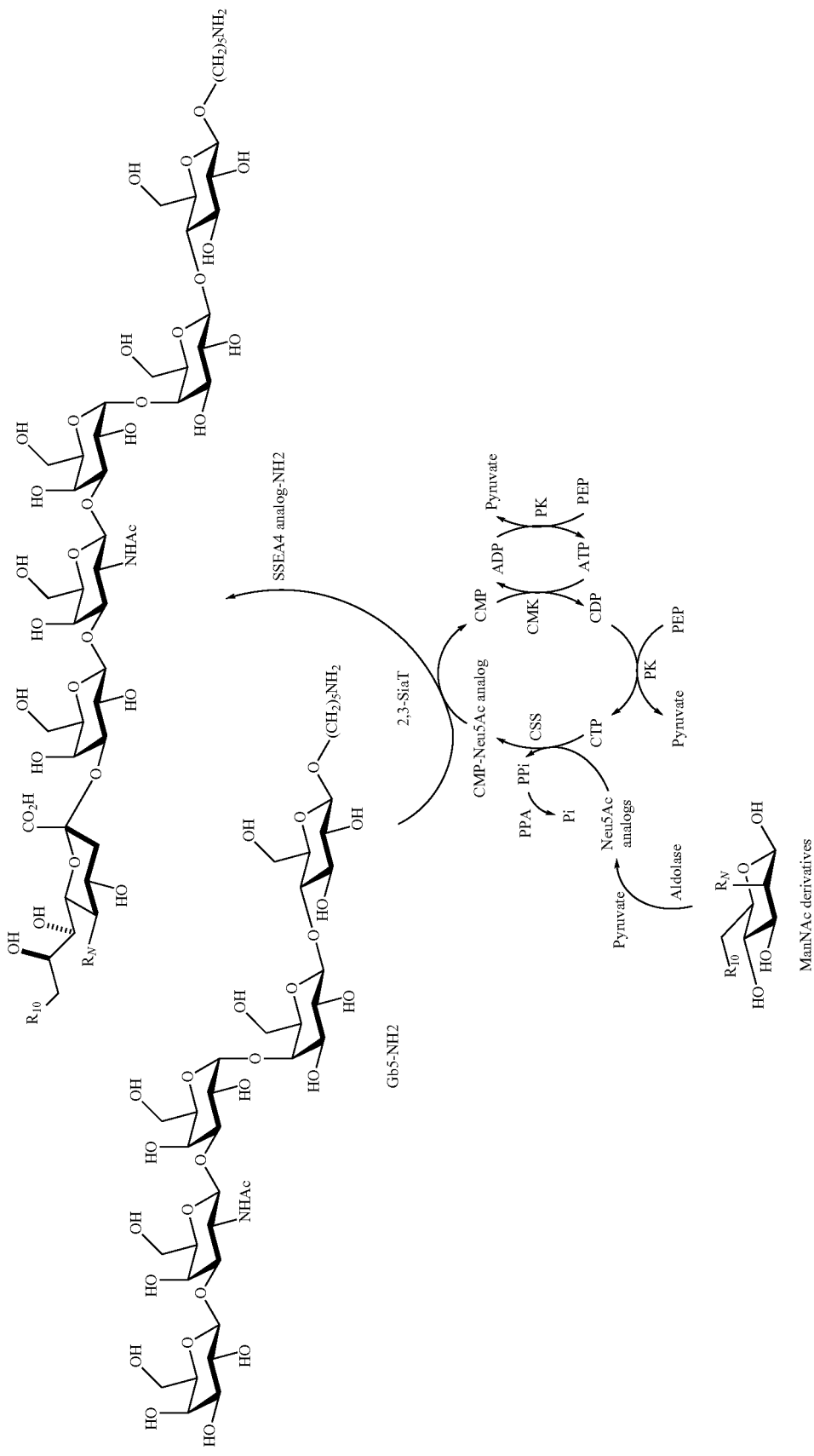

SSEA4 analogs-NH2 were synthesized via enzymatic regeneration strategy as described in Scheme 3. In this system, ManNAc derivatives were reacted with pyruvate and transformed into Neu5Ac analogs by aldolase catalysis, followed by incorporation with Gb5-NH2 in the regeneration system (J. Am. Chem. Soc. 2013, 135, 14831-14839) to obtain the exemplary SSEA4 analogs-NH2.

Detail of the reaction condition is described as follows: Gb5-NH2 (18 µmol), CTP (5 µmol), ManNAc derivative (27 µmol), sodium pyruvate (81 µmol), PEP (55 µmol), and ATP (5 µmol), were dissolved in 50 mM Tris-HCl buffer (pH 8.0). Enzymes alpha-(2,3)-sialyltransferase (20 units), sialic acid aldolase (20 units) CMK (10 units), Pykf (10 units), PPA (10 units), and Pmcss (10 units) were added to the solution, and the reaction was incubated at 37° C. for 8 hours and monitored by TLC plate. At the end of reaction, enzyme was denatured by heating at 100° C. for 5 minutes. The desired SSEA4 analog-NH2 was purified by G25, DEAE, and SP column (80%).

$^1$H NMR of SSEA4 analogs-NH2

B-1. SSEA4-pentylamine (RN=NHAc, R10=OH)

$^1$H NMR (400 MHz, D$_2$O) δ 4.94 (d, J=3.8 Hz, 1H), 4.72 (d, J=8.5 Hz, 1H), 4.54-4.50 (m, 3H), 4.40 (t, J=6.4 Hz, 1H), 4.27 (d, J=2.0 Hz, 1H), 4.20 (d, J=2.8 Hz, 1H), 4.10-3.54 (m, 37 H), 3.34-3.31 (m, 1H), 3.02 (t, J=7.6 Hz, 2H), 2.78 (dd, J=12.4, 4.6 Hz, 1H), 2.05 (m, 6H), 1.80 (t, 12.2 Hz, 1H), 1.74-1.67 (m, 4H), 1.51-1.45 (m, 2H)

B-2. Neu5Gc_SSEA4-pentylamine (RN=NHGc, R10=OH)

$^1$H NMR (400 MHz, D$_2$O) δ 4.89 (d, J=3.6 Hz, 1H), 4.66 (d, J=8.2 Hz, 1H), 4.52-4.45 (m, 3H), 4.37 (t, J=6.8 Hz, 1H), 4.23 (d, J=3.2 Hz, 1H), 4.15 (d, J=2.8 Hz, 1H), 4.10-3.48 (m, 35 H), 3.27 (m, 1H), 2.98 (t, J=7.6 Hz, 2H), 2.73 (dd, J=4.8, 12.4 Hz, 1H), 2.00 (s, 3H), 1.77 (t, J=12.0 Hz, 1H), 1.72-1.61 (m, 4H), 1.48-1.39 (m, 2 H).

B-3. Ac-Alkynyl_SSEA4-pentylamine (RN=NHCOC$_2$H$_4$C≡CH, R10=OH)

$^1$H NMR (400 MHz, D$_2$O) δ 4.89 (d, J=4.0 Hz, 1H), 4.67 (d, J=8.4 Hz, 1H), 4.52-4.45 (m, 3H), 4.37 (t, J=6.4 Hz, 1H), 4.23 (d, J=2.4 Hz, 1H), 4.08-3.54 (m, 38H), 3.28 (m, 1H), 2.99 (t, J=7.6 Hz, 2H), 2.53-2.4 (m, 4H), 2.37 (s, 1H), 2.01 (s, 3H), 1.77 (t, J=12.0 Hz, 1H), 1.72-1.62 (m, 4H), 1.49-1.41 (m, 2 H).

B-4. Ac-Fluoride_SSEA4-pentylamine (RN=NHCOCH$_2$F, R10=OH)

$^1$H NMR (400 MHz, D$_2$O) δ 4.90 (d, J=46.4 Hz, 2H), 4.90 (d, J=4.0 Hz, 1 H), 4.67 (d, J=8.8 Hz, 1H), 4.53-4.46 (m, 3H), 4.37 (t, J=6.8 Hz, 1 H), 4.24 (d, J=2.8 Hz, 2H), 4.16 (d, J=3.2 Hz, 1 H), 4.09-3.51 (m, 34H), 3.28 (m, 1H), 2.99 (t, J=7.2 Hz, 1H), 2.75 (dd, J=4.8, 12.4 Hz, 1H), 2.01 (s, 3H), 1.79 (t, J=12.0 Hz, 1H), 1.72-1.62 (m, 4H), 1.48-1.40 (m, 2 H).

B-5. Ac-Phenyl_SSEA4-pentylamine (RN=NHCOCH$_2$Ph, R10=OH)

$^1$H NMR (400 MHz, D$_2$O) δ 7.39-7.30 (m, 5H), 4.90 (d, J=4.0 Hz, 1H), 4.66 (d, J=8.4 Hz, 1H), 4.52-4.46 (m, 3H), 4.37 (t, J=6.8 Hz, 1H), 4.23 (d, J=2.8 Hz, 1H), 4.15 (d, J=3.2 Hz, 1H), 4.08-3.47 (m, 38H), 3.36 (dd, J=1.6, 9.2 Hz, 1H), 3.28 (m, 1H), 2.99 (t, J=7.6 Hz, 2H), 2.73 (dd, J=4.8, 12.4 Hz, 1H), 2.00 (s, 3H), 1.76 (t, J=12.0 Hz, 1H), 1.72-1.61 (m, 4H), 1.51-1.40 (m, 2 H).

B-6. Ac-Azido_SSEA4-pentylamine (RN=NHCOCH$_2$N$_3$, R10=OH)

$^1$H NMR (400 MHz, D$_2$O) δ 4.88 (d, J=3.6 Hz, 1H), 4.66 (d, J=8.4 Hz, 1H), 4.52-4.44 (m, 3H), 4.36 (t, J=6.4 Hz, 1H), 4.23 (d, J=2.4 Hz, 1H), 4.08-3.54 (m, 35H), 3.27 (m, 1H), 2.98 (t, J=7.2 Hz, 2H), 2.73 (dd, J=4.8, 12.4 Hz, 1H), 2.00 (s, 3H), 1.77 (t, J=12.4 Hz, 1H), 1.72-1.60 (m, 4H), 1.48-1.39 (m, 2 H).

B-7. 5'-Azido_SSEA4-pentylamine (RN=N$_3$, R10=OH)

$^1$H NMR (400 MHz, D$_2$O): δ 4.90 (d, J=3.6 Hz, 1H), 4.67 (d, J=8.4 Hz, 1H), 4.51-4.47 (m, 3H), 4.37 (t, J=6.4 Hz, 1H), 4.23 (d, J=2.8 Hz, 1H), 4.15 (d, J=3.2 Hz, 1H), 4.08-3.44 (m, 35H), 3.31-3.27 (m, 1H), 2.99 (t, J=7.2 Hz, 1H), 2.73 (dd, J=4.8, 12.4 Hz, 1H), 2.01 (s, 3H), 1.76 (t, J=12.0 Hz, 1H), 1.72-1.63 (3, 4H), 1.48-1.41 (m, 2H); HRMS (ESI-TOF, M−H−) C$_{46}$H$_{78}$N$_5$O$_{33}$— calcd for 1228.4579, found 1228.4621.

B-8. 9'-Azido_SSEA4-pentylamine (RN=NHAc, R10=N$_3$)

$^1$H NMR (400 MHz, D$_2$O) δ 4.85 (d, J=3.8 Hz, 1H), 4.67 (d, J=8.4 Hz, 1H), 4.51-4.44 (m, 3H), 4.37 (t, J=6.4 Hz, 1H), 4.23 (d, J=2.8 Hz, 1H), 4.10-3.40 (m, 33H), 3.27 (m, 1H), 2.98 (t, J=7.6 Hz, 2H), 2.72 (dd, J=4.8, 12.8 Hz, 1H), 2.00 (s, 3H), 2.00 (s, 3H), 1.75 (t, J=12.4 Hz, 1H), 1.72-1.60 (m, 4H), 1.58-1.38 (m, 2 H).

B-9. NHBz_SSEA4-pentylamine (RN=NHBz, R10=OH)

$^1$H NMR (400 MHz, D$_2$O) δ 7.80-7.73 (m, 2H), 7.63 (m, 1H), 7.56-7.51 (m, 2H), 4.92 (d, J=4.0 Hz, 1H), 4.70 (d, J=8.4 Hz, 1H), 4.58-4.47 (m, 3H), 4.40 (t, J=6.4 Hz, 1H), 4.26 (d, J=2.8 Hz, 1H), 4.19 (d, J=3.2 Hz, 1H), 4.15-3.53 (m, 36H), 3.31 (m, 1H), 3.01 (t, J=7.6 Hz, 2H), 2.82 (dd, J=4.4, 12.4 Hz, 1H), 2.00 (s, 3H), 1.87 (t, J=12.0 Hz, 1H), 1.72-1.60 (m, 4H), 1.48-1.39 (m, 2 H).

C: Cross-linking Reaction for SSEA4 Analog-SH Reaction

Scheme 4: Synthesis of SSEA4 analog-SH via DTSSP cross-liking

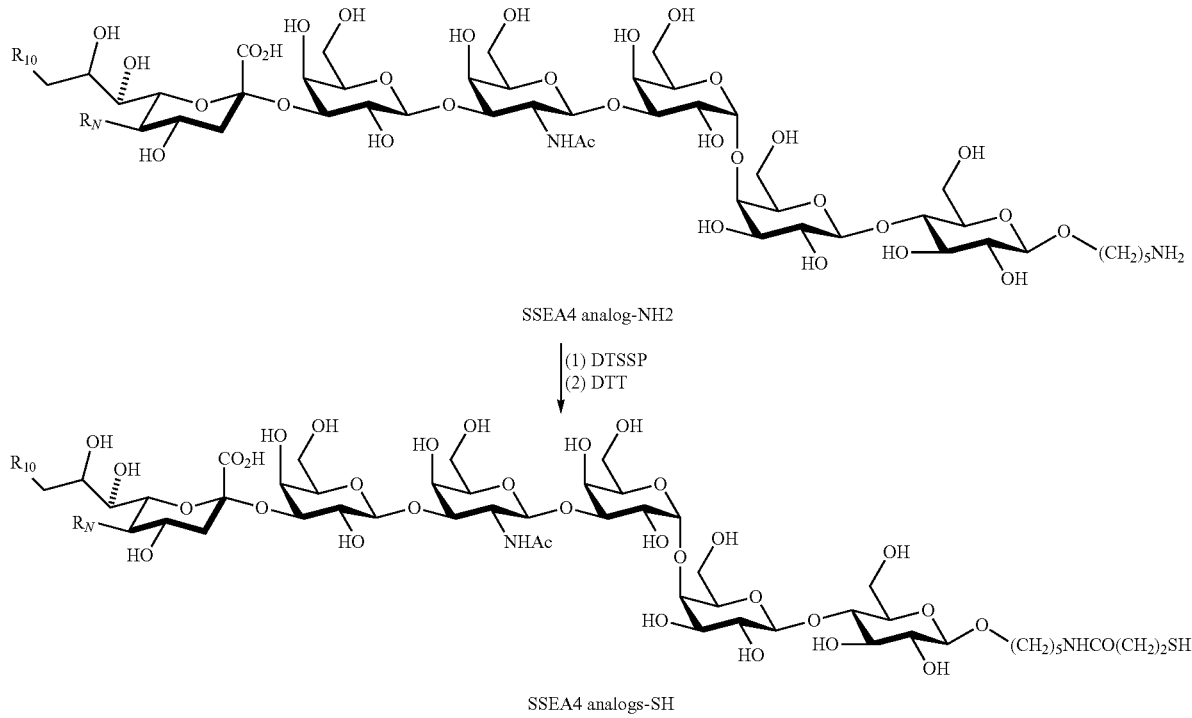

In certain embodiments, DTSSP (2.0 eq) and SSEA4 analog-NH2 (1.0 eq) was mixed in 0.1 M phosphate buffer, pH 7.4 (~3 mg/ml). The solution was stirred at room temperature for overnight. Then the reaction mixture was warmed to 40° C. and added with DTT (9.0 eq). After stirring for 1.5 hrs at 40° C., the reaction mixture was concentrated in vacuo, and the residue was purified by LH-20 column to afford a white solid SSEA4 analogs-SH. (Scheme 4)

$^1$H NMR of SSEA4 analogs-SH

C-1: SSEA4-SH (RN═NHAc, R10═OH)

$^1$H NMR (400 Hz, D$_2$O) δ 4.88 (d, J=4.0 Hz, 1H), 4.65 (d, J=8.5 Hz, 1H), 4.50-4.44 (m, 3H), 4.36 (t, J=6.5 Hz, 1H), 4.22 (d, J=2.9 Hz, 1H), 4.14 (d, J=3.1 Hz, 1H), 4.04-3.55 (m, 35H), 3.26 (t, J=8.5 Hz, 1H), 3.18 (t, J=6.8 Hz, 2H), 2.74-2.70 (m, 3H), 2.49 (t, J=6.8 Hz, 2H), 1.994 (s, 3H), 1.992 (s, 3H), 1.75 (t, J=12.2 Hz, 1H), 1.61 (tt, J=6.7, 6.7 HZ, 2H), 1.52 (tt, J=7.1, 7.1 Hz, 2H), 1.40-1.36 (m, 2H);

C-2: Neu5Gc_SSEA4-SH (RN═NHGc, R10═OH)

$^1$H NMR (400 MHz, D$_2$O) δ 4.89 (d, J=3.9 Hz, 1H), 4.66 (d, J=8.5 Hz, 1H), 4.53-4.43 (m, 3H), 4.36 (t, J=6.5 Hz, 1H), 4.22 (d, J=3.0 Hz, 1H), 4.15 (d, J=3.1 Hz, 1H), 4.11-3.48 (m, 38H), 3.27 (t, J=8.4 Hz, 1H), 3.19 (t, J=6.7 Hz, 2H), 2.78-2.71 (m, 3H), 2.51 (t, J=6.7 Hz, 2H), 2.00 (s, 3H), 1.78 (t, J=12.1 Hz, 1H), 1.61 (q, J=7.1 Hz, 2H), 1.52 (q, J=7.1 Hz, 2H), 1.39 (q, J=8.0 Hz, 2H).

C-3: Ac-Alkynyl_SSEA4-SH (RN═NHCOC$_2$H$_4$C≡CH, R10═OH)

$^1$H NMR (400 MHz, D$_2$O) δ 4.94 (d, J=3.9 Hz, 1H), 4.72 (d, J=8.4 Hz, 1H), 4.58-4.48 (m, 3H), 4.41 (t, J=6.5 Hz, 1H), 4.30-4.26 (m, 1H), 4.21 (d, J=3.1 Hz, 1H), 4.14-3.54 (m, 37H), 3.32 (t, J=8.6 Hz, 1H), 3.24 (t, J=6.8 Hz, 2H), 2.83-2.74 (m, 3H), 2.59-2.49 (m, 5H), 2.43 (s, 1H), 2.06 (s, 3H), 1.82 (t, J=12.1 Hz, 1H), 1.67 (p, J=6.9 Hz, 2H), 1.58 (p, J=6.9 Hz, 2H), 1.48-1.38 (m, 2H).

C-4: Ac-Fluoride_SSEA4-SH (RN═NHCOCH$_2$F, R10═OH)

$^1$H NMR (400 MHz, D$_2$O) δ 4.90 (d, J=46.4 Hz, 2H), 4.95 (d, J=4.0 Hz, 1H), 4.72 (d, J=8.5 Hz, 1H), 4.59-4.48 (m, 3H), 4.41 (t, J=6.6 Hz, 1H), 4.31-4.26 (m, 1H), 4.23-4.18 (m, 1H), 4.14-3.54 (m, 36H), 3.36-3.29 (m, 1H), 3.25 (t, J=6.8 Hz, 2H), 2.80 (m, 3H), 2.57 (t, J=6.7 Hz, 2H), 2.06 (s, 3H), 1.84 (t, J=12.2 Hz, 1H), 1.67 (p, J=6.9 Hz, 2H), 1.58 (p, J=7.0 Hz, 2H), 1.43 (q, J=8.3 Hz, 2H).

C-5: Ac-Phenyl_SSEA4-SH (RN═NHCOCH$_2$Ph, R10═OH)

$^1$H NMR (400 MHz, D$_2$O) δ 7.48-7.32 (m, 5H), 4.94 (d, J=3.6 Hz, 1H), 4.73-4.68 (d, J=8.4 Hz, 1H), 4.52 (m, 3H), 4.41 (t, J=6.4 Hz, 1H), 4.29-4.26 (m, 1H), 4.20 (d, J=3.0 Hz, 1H), 4.13-3.51 (m, 37H), 3.39 (dd, J=9.0, 1.8 Hz, 1H), 3.32 (t, J=8.6 Hz, 1H), 3.25 (t, J=6.7 Hz, 2H), 2.83-2.74 (m, 3H), 2.56 (t, J=6.7 Hz, 2H), 2.04 (s, 3H), 1.80 (t, J=12.1 Hz, 1H), 1.67 (q, J=7.2 Hz, 2H), 1.57 (q, J=7.1 Hz, 2H), 1.48-1.38 (m, 2H).

C-6: Ac-Azido_SSEA4-SH (RN═NHCOCH$_2$N$_3$, R10═OH)

$^1$H NMR (400 MHz, D$_2$O) δ 4.88 (d, J=3.9 Hz, 1H), 4.66 (d, J=8.5 Hz, 1H), 4.52-4.43 (m, 3H), 4.36 (t, J=6.5 Hz, 1H), 4.22 (d, J=3.1 Hz, 1H), 4.14 (d, J=3.1 Hz, 1H), 4.08-3.47 (m, 38H), 3.26 (t, J=8.4 Hz, 1H), 3.19 (t, J=6.8 Hz, 2H), 2.74 (m, 3H), 2.51 (t, J=6.7 Hz, 2H), 2.00 (s, 3H), 1.76 (t, J=12.1 Hz, 1H), 1.61 (q, J=7.1 Hz, 2H), 1.53 (p, J=7.0 Hz, 2H), 1.38 (q, J=8.3 Hz, 2H).

C-7: 5'-Azido_SSEA4-SH (RN═N$_3$, R10═OH)

$^1$H NMR (400 Hz, D$_2$O) δ 4.90 (d, J=4.0 Hz, 1H), 4.67 (d, J=8.4 Hz, 1H), 4.51-4.46 (m, 3H), 4.37 (t, J=6.4 Hz, 1H), 4.24 (d, J=2.8 Hz, 1H), 4.15 (d, J=2.8 Hz, 1H), 4.01-3.44 (m, 35H), 3.28 (t, J=8.4 Hz, 1H), 3.21 (t, J=6.8 Hz, 2H), 2.78-2.72 (m, 3H), 2.52 (t, J=7.2 Hz, 2H), 2.02 (s, 3H), 1.77 (t, J=12.0 Hz, 1H), 1.67-1.60 (m, 2H), 1.58-1.50 (m, 2H), 1.43-1.37 (m, 2H)

C-8: 9'-Azido_SSEA4-SH (RN=NHAc, R10=$N_3$)

$^1$H NMR (400 MHz, $D_2O$) δ 4.90 (d, J=3.9 Hz, 1H), 4.68 (d, J=8.5 Hz, 1H), 4.48 (dd, J=13.2, 7.9 Hz, 3H), 4.37 (t, J=6.5 Hz, 1H), 4.26-4.22 (m, 1H), 4.16 (d, J=3.3 Hz, 1H), 4.09-3.44 (m, 36H), 3.31-3.24 (m, 1H), 3.20 (t, J=6.8 Hz, 2H), 2.79-2.70 (m, 3H), 2.52 (t, J=6.7 Hz, 2H), 2.02 (d, J=2.0 Hz, 6H), 1.76 (t, J=12.1 Hz, 1H), 1.63 (p, J=6.9 Hz, 2H), 1.54 (p, J=6.9 Hz, 2H), 1.39 (q, J=8.3 Hz, 2H).

C-9: NHBz_SSEA4-SH (RN=NHBz, R10=OH)

$^1$H NMR (400 MHz, $D_2O$) δ 7.80-7.73 (m, 2H), 7.66-7.58 (m, 1H), 7.52 (dd, J=8.4, 7.0 Hz, 2H), 4.91 (d, J=3.9 Hz, 1H), 4.69 (d, J=8.5 Hz, 1H), 4.57-4.44 (m, 3H), 4.38 (t, J=6.5 Hz, 1H), 4.27-4.22 (m, 1H), 4.18 (d, J=3.1 Hz, 1H), 4.16-3.52 (m, 36H), 3.29 (t, J=8.5 Hz, 1H), 3.20 (t, J=6.8 Hz, 2H), 2.84-2.72 (m, 3H), 2.52 (t, J=6.7 Hz, 2H), 2.03 (s, 3H), 1.89 (t, J=12.2 Hz, 1H), 1.63 (p, J=6.8 Hz, 2H), 1.53 (q, J=7.1 Hz, 2H), 1.40 (q, J=8.2 Hz, 2H).

D: Chemoenzymatic Synthesis of SSEA4 Analog-allyl System

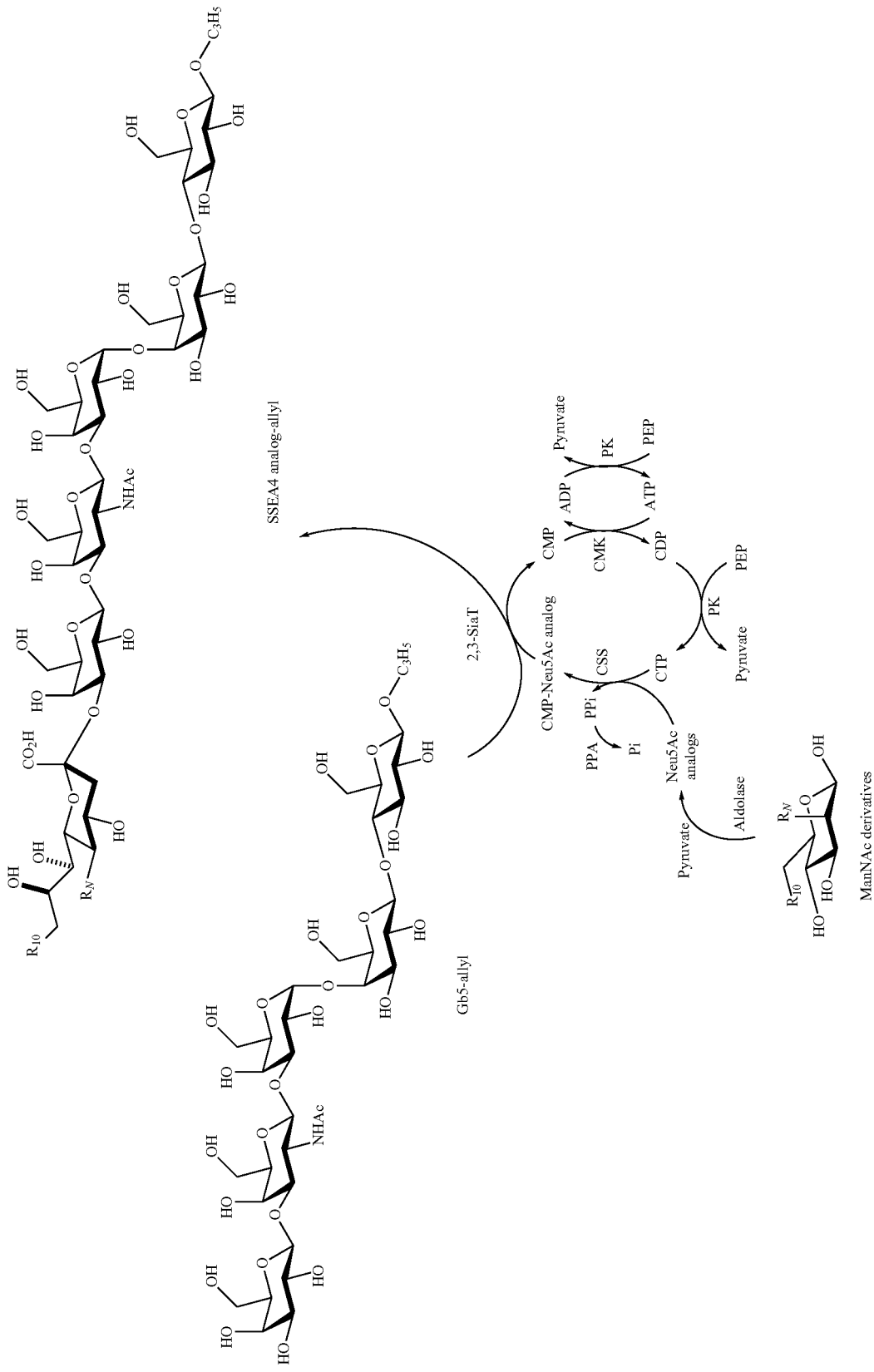

SSEA4 analogs-allyl were synthesized via enzymatic regeneration strategy as described in Scheme 5. In this system, ManNAc derivatives were reacted with pyruvate and transformed into Neu5Ac analogs by aldolase catalysis, followed by incorporation with Gb5-ally in the regeneration system (J. Am. Chem. Soc. 2013, 135, 14831-14839) to obtain the exemplary SSEA4 analogs-allyl. (Scheme 5)

Detail of the reaction condition is described as follows: Gb5-allyl (18 μmol), CTP (5 μmol), ManNAc derivative (27 μmol), sodium pyruvate (81 μmol), PEP (55 μmol), and ATP (5 μmol), were dissolved in 50 mM Tris-HCl buffer (pH 8.0). Enzymesalpha-(2,3)-sialyltransferase (20 units), sialic acid aldolase (20 units) CMK (10 units), Pykf (10 units), PPA (10 units), and Pmcss (10 units) were added to the solution, and the reaction was incubated at 37° C. for 8 hours and monitored by TLC plate. At the end of reaction, enzyme was denatured by heating at 100° C. for 5 minutes. The desired SSEA4-analog-allyl was purified by G25, DEAE, and SP column (80%).

$^1$H NMR of SSEA4 analogs-allyl

D-1. SSEA4-allyl (R1=OH, RN=NHAc, R10=OH)

$^1$H NMR (400 MHz, D$_2$O) δ 6.00 (m, 1H), 5.40-5.37 (d, J=17.3 Hz, 1H), 5.30-5.28 (d, J=10.4 Hz, 1H), 4.92 (d, J=3.9 Hz, 1H), 4.70 (d, J=8.5 Hz, 1H), 4.54-4.51 (m, 3H), 4.40-4.38 (m, 2H), 4.25-4.18 (m, 3H), 4.10-3.52 (m, 34 H), 3.35-3.32 (t, J=8.6 Hz, 1H), 2.77 (dd, J=12.5, 4.6 Hz, 1H), 2.03 (s, 6H), 1.80 (t, J=12.1 Hz, 1H)

D-2. Neu5Gc_SSEA4-allyl (R1=OH, RN=NHGc, R10=OH)

$^1$H NMR (400 MHz, D$_2$O) δ 5.99 (m, 1H), 5.38 (dd, J=1.2, 17.2 Hz, 1H), 5.29 (dd, J=1.2, 10.0 Hz, 1H), 4.93 (d, J=4.0 Hz, 1H), 4.69 (d, J=8.4 Hz, 1H), 4.58-4.51 (m, 3H), 4.43-4.37 (m, 2H), 4.28-4.17 (m, 3H), 4.14-3.52 (m, 34 H), 3.33 (t, J=8.8 Hz, 1H), 2.77 (dd, J=4.8, 12.4 Hz, 1H), 2.03 (s, 3H), 1.81 (t, J=12.0 Hz, 1H).

D-3. Ac-Fluoride_SSEA4-allyl (R1=OH, RN=NHCOCH$_2$F, R10=OH)

$^1$H NMR (400 MHz, D$_2$O) δ 5.96 (m, 1H), 5.36 (dd, J=1.6, 17.2 Hz, 1H), 5.25 (dd, J=1.6, 10.4 Hz, 1H), 4.89 (d, J=46.4 Hz, 2H), 4.88 (d, J=3.6 Hz, 1H), 4.65 (d, J=8.4 Hz, 1H), 4.53-4.45 (m, 3H), 4.39-4.32 (m, 2H), 4.22-3.51 (m, 37H), 3.30 (t, J=8.4 Hz, 1H), 2.73 (dd, J=4.4, 12.4 Hz, 1H), 2.00 (s, 3H), 1.85 (t, J=12.4 Hz, 1H).

D-4. Ac-Phenyl_SSEA4-allyl (R1=OH, RN=NHCOCH$_2$Ph, R10=OH)

$^1$H NMR (400 MHz, D$_2$O) δ 7.45-7.34 (m, 5H), 6.02 (m, 1H), 5.42 (dd, J=1.2, 17.2 Hz, 1H), 5.32 (dd, J=1.2, 10.4 Hz, 1H), 4.94 (d, J=4.0 Hz, 1H), 4.72 (d, J=8.4 Hz, 1H), 4.59-4.52 (m, 3H), 4.46-4.38 (m, 2H), 4.30-3.50 (m, 38 H), 3.42-3.32 (m, 4H), 2.77 (dd, J=4.4, 12.8 Hz, 1H), 2.05 (s, 3H), 1.90 (t, J=12.0 Hz, 1H).

D-5. Ac-Azido_SSEA4-allyl (R1=OH, RN=NHCOCH$_2$N$_3$, R10=OH)

$^1$H NMR (400 MHz, D$_2$O) δ 5.95 (m, 1H), 5.35 (dd, J=1.6, 17.2 Hz, 1H), 5.25 (dd, J=1.2, 10.4 Hz, 1H), 4.88 (d, J=3.6 Hz, 1H), 4.65 (d, J=8.4 Hz, 1H), 4.52-4.46 (m, 3H), 4.40-4.32 (m, 2H), 4.23-4.18 (m, 3H), 4.12-3.50 (m, 36 H), 3.30 (t, J=5.6 Hz, 1H), 2.72 (dd, J=4.8, 12.8 Hz, 1H), 2.00 (s, 3H), 1.84 (t, J=12.4 Hz, 1H).

D-6. 5'-Azido_SSEA4-allyl (R1=OH, RN=N$_3$, R10=OH)

$^1$HNMR (400 MHz, D$_2$O): δ 5.99 (m, 1H), 4.40 (dd, J=1.6, 17.2 Hz, 1H), 5.29 (d, J=10.4 Hz, 1H), 4.92 (d, J=3.6 Hz, 1H), 4.70 (d, J=8.4 Hz, 1H), 4.56-4.51 (m, 3H), 4.43-4.38 (m, 2H), 4.26 (d, J=3.6 Hz, 2H), 4.22 (d, J=6.4 Hz, 1H), 4.10-3.46 (m, 35H), 3.36-3.32 (m, 1H), 2.74 (dd, J=4.8, 12.4 Hz, 1H), 2.04 (s, 3H), 1.79 (t, J=12.4 Hz); HRMS (ESI-TOF, M−H−) C$_{44}$H$_{71}$N$_4$O$_{33}$ calcd for 1183.4001, found 1183.4056.

D-7. 9'-Azido_SSEA4-allyl (R1=OH, RN=NHAc, R10=N$_3$)

$^1$H NMR (400 MHz, D$_2$O) δ 5.96 (m, 1H), 5.36 (dd, J=1.6, 17.3 Hz, 1H), 5.26 (dd, J=1.6, 10.4 Hz, 1H), 4.90 (d, J=3.6 Hz, 1H), 4.68 (d, J=8.4 Hz, 1H), 4.55-4.47 (m, 3H), 4.41-4.35 (m, 2H), 4.25-4.14 (m, 3H), 4.10-3.41 (m, 34 H), 3.31 (t, J=6.8 Hz, 1H), 2.72 (dd, J=4.8, 12.8 Hz, 1H), 2.02 (s, 3H), 1.79 (t, J=12.0 Hz, 1H).

D-8. NHBz_SSEA4-allyl (R1=OH, RN=NHBz, R10=OH)

$^1$H NMR (400 MHz, D$_2$O) δ 7.76-7.73 (m, 2H), 7.59 (m, 1H), 7.51-7.46 (m, 2H), 5.90 (m, 1H), 5.30 (dd, J=1.6, 17.2 Hz, 1H), 5.25 (dd, J=1.6, 10.8 Hz, 1H), 4.89 (d, J=3.6 Hz, 1H), 4.67 (d, J=8.8 Hz, 1H), 4.55-4.45 (m, 3H), 4.39-4.38 (m, 2H), 4.24-3.50 (m, 34H), 3.30 (t, J=8.0 Hz, 1H), 2.77 (dd, J=4.4, 12.4 Hz, 1H), 2.01 (s, 3H), 1.90 (t, J=12.4 Hz, 1H).

E: Oxidation Reaction for SSEA4 Analog-aldehyde

Scheme 6.

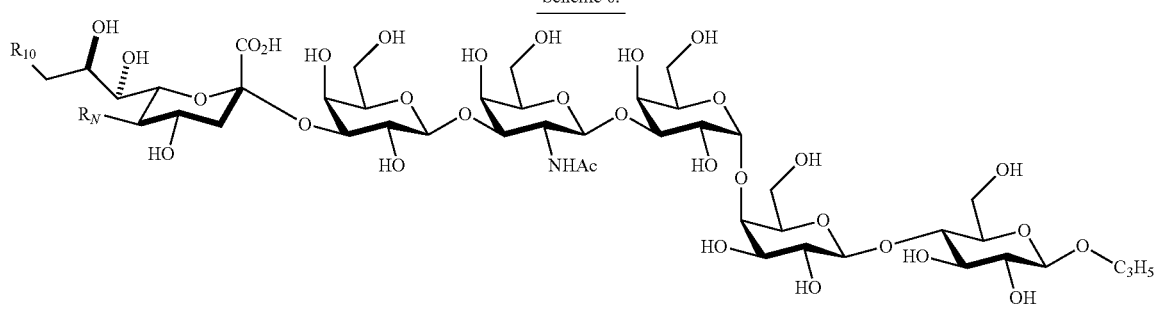

SSEA4 analogs-allyl

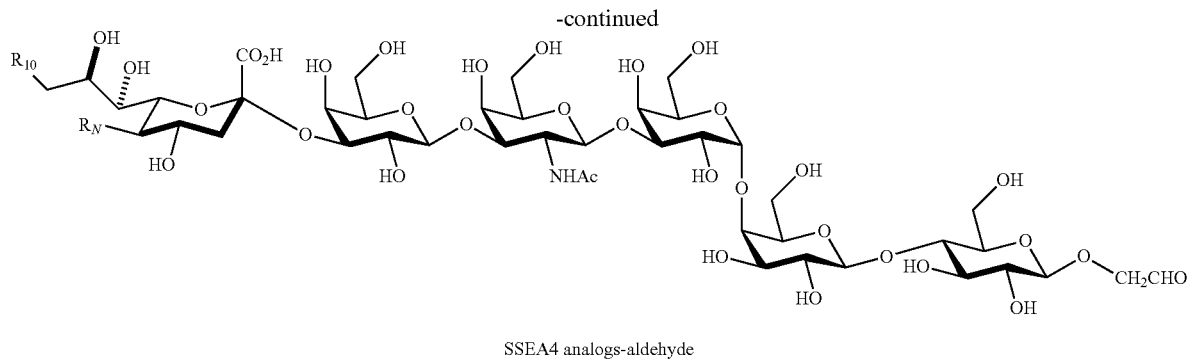

SSEA4 analogs-aldehyde

In certain exemplary embodiments, a stirred solution of the SSEA4 analogs-allyl in methanol and H₂O was ozonolysis for 15 minutes under $O_3$ gas atmosphere at −70° C. The reaction mixture was quenched by dimethyl sulfide (Me₂S) and then the solution was evaporated in vacuo. The desired SSEA4 analogs-aldehyde was then purified by G15. (Scheme 6)

¹H NMR of SSEA4 analogs-aldehyde

E-1: SSEA4-aldehyde (RN=NHAc, R10=OH)
¹H NMR (400 MHz, D₂O) δ 5.19 (t, J=4.9 Hz, 1H), 4.89 (d, J=3.9 Hz, 1H), 4.66 (d, J=8.4 Hz, 1H), 4.54-4.45 (m, 3H), 4.36 (t, J=6.5 Hz, 1H), 4.25-4.20 (m, 1H), 4.15 (d, J=3.1 Hz, 1H), 4.08-3.47 (m, 32H), 3.37-3.30 (m, 1H), 2.73 (dd, J=12.4, 4.6 Hz, 1H), 2.00 (d, J=0.9 Hz, 6H), 1.76 (t, J=12.1 Hz, 1H).

E-2: Neu5Gc_SSEA4-aldehyde (RN=NHGc, R10=OH)
¹H NMR (400 MHz, D₂O) δ 5.20 (t, J=4.9 Hz, 1H), 4.91 (d, J=3.9 Hz, 1H), 4.68 (d, J=8.5 Hz, 1H), 4.52 (dt, J=8.5, 4.5 Hz, 3H), 4.38 (t, J=6.5 Hz, 1H), 4.27-4.22 (m, 1H), 4.17 (d, J=3.1 Hz, 1H), 4.13-3.51 (m, 34H), 3.38-3.32 (m, 1H), 2.76 (dd, J=12.4, 4.6 Hz, 1H), 2.02 (s, 3H), 1.80 (t, J=12.1 Hz, 1H).

E-3: Ac-Fluoride_SSEA4-aldehyde (RN=NHCOCH₂F, R10=OH)
¹H NMR (400 MHz, D₂O) δ 5.21 (t, J=4.9 Hz, 1H), 4.90 (d, J=46.4 Hz, 2H), 4.69 (d, J=8.5 Hz, 1H), 4.52 (t, J=8.0 Hz, 3H), 4.38 (t, J=6.4 Hz, 1H), 4.24 (d, J=3.1 Hz, 1H), 4.17 (d, J=3.2 Hz, 1H), 4.10-3.45 (m, 33H), 3.40-3.32 (m, 1H), 2.78 (dd, J=12.4, 4.6 Hz, 1H), 2.03 (s, 3H), 1.81 (t, J=12.2 Hz, 1H).

E-4: Ac-Phenyl_SSEA4-aldehyde (RN=NHCOCH₂Ph, R10=OH)
¹H NMR (400 MHz, D₂O) δ 7.48-7.27 (m, 5H), 5.22 (t, J=4.9 Hz, 1H), 4.92 (d, J=4.0 Hz, 1H), 4.69 (d, J=8.4 Hz, 1H), 4.56-4.49 (m, 3H), 4.39 (t, J=6.5 Hz, 1H), 4.26 (m, 1H), 4.18 (m, 1H), 4.10-3.45 (m, 34H), 3.43-3.34 (m, 1H), 2.76 (dd, J=12.4, 4.6 Hz, 1H), 2.03 (s, 3H), 1.78 (t, J=12.3 Hz, 1H).

E-5: Ac-Azido_SSEA4-aldehyde (RN=NHCOCH₂N₃, R10=OH)
¹H NMR (400 MHz, D₂O) δ 5.20 (t, J=4.9 Hz, 1H), 4.90 (d, J=3.9 Hz, 1H), 4.68 (d, J=8.5 Hz, 1H), 4.54-4.48 (m, 3H), 4.38 (t, J=6.4 Hz, 1H), 4.24 (d, J=3.1 Hz, 1H), 4.17 (d, J=3.1 Hz, 1H), 4.13-3.51 (m, 34H), 3.39-3.32 (m, 1H), 2.75 (dd, J=12.4, 4.6 Hz, 1H), 2.02 (s, 3H), 1.79 (t, J=12.2 Hz, 1H).

E-6: 9'-Azido_SSEA4-aldehyde (RN=NHAc, R10=N₃)
¹H NMR (400 MHz, D₂O) δ 5.20 (t, J=4.9 Hz, 1H), 4.91 (d, J=3.9 Hz, 1H), 4.69 (d, J=8.5 Hz, 1H), 4.52 (t, J=8.0 Hz, 3H), 4.38 (t, J=6.4 Hz, 1H), 4.24 (d, J=3.1 Hz, 1H), 4.17 (d, J=3.2 Hz, 1H), 4.10-3.45 (m, 32H), 3.39-3.32 (m, 1H), 2.74 (dd, J=12.5, 4.6 Hz, 1H), 2.03 (d, J=2.1 Hz, 6H), 1.77 (t, J=12.1 Hz, 1H).

E-7: NHBz_SSEA4-aldehyde (RN=NHBz, R10=OH)
¹H NMR (400 MHz, D₂O) δ 7.83-7.76 (m, 2H), 7.63 (t, J=7.3 Hz, 1H), 7.53 (t, J=7.7 Hz, 2H), 5.21 (t, J=4.9 Hz, 1H), 4.92 (d, J=3.8 Hz, 1H), 4.70 (d, J=8.5 Hz, 1H), 4.57-4.49 (m, 3H), 4.39 (t, J=6.5 Hz, 1H), 4.26 (d, J=3.1 Hz, 1H), 4.19 (d, J=3.3 Hz, 1H), 4.16-3.52 (m, 32H), 3.40-3.34 (m, 1H), 2.82 (dd, J=12.4, 4.6 Hz, 1H), 2.04 (d, J=4.7 Hz, 3H), 1.87 (t, J=12.1 Hz, 1H).

Example 3

Synthesis of SSEA3/SSEA4 Analog CRM197-conjugates Via Sulfo-EMCS Crosslink

Scheme 7

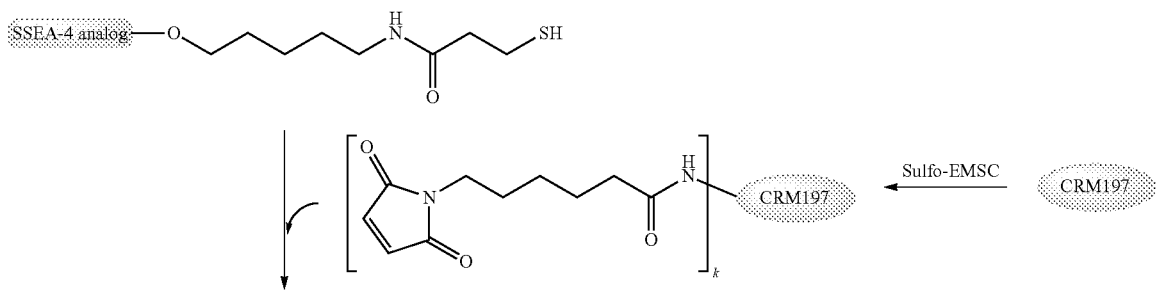

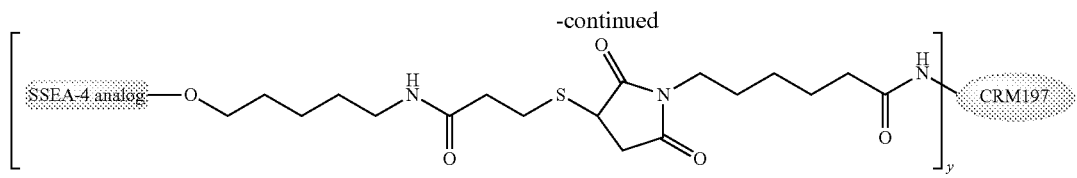

General Methods:

Step A. To modify SSEA3 analog-NH2 or SSEA4 analog-NH2 into SSEA3 analog-SH or SSEA4-analog-SH To synthesize SSEA3/4 analog CRM197-conjugates, the amine-terminated SSEA3/4 analogs were reacted with the DTSSP linker in PBS buffer (pH 7.4) at room temperature. To monitor the pH value of solution by pH paper, and add some NaOH solution to the solution when the solution became neuter or acid. After the reaction was stirred at room temperature for 12 hours, DTT was added to the solution at room temperature. The solution was kept stirring at 40° C., and then the solvent was removed under reduced pressure. The residue was purified by LH-20 column chromatography to give SSEA3/4 analog-SH.

Step B: To modify CRM197 into CRM197-maleimide.

After the salt of commercial CRM197 (1.0 mg) was removed via alternate dissolving in water and dialyzing (Amicon Ultra-0.5, 10 kDa,), the residue was dissolved in PBS buffer (pH 6.5, 1.0 mL) and transferred into a sample vial. Sulfo-EMCS (1.0 mg, $8.22 \times 10^{-6}$ mol) was added to the solution, and then the reaction was kept stirring at room temperature for 2 hours. The mixture was purified by Amicon Ultra-0.5 (10 kDa). After using MALDI-TOF to check the molecular weight and BCA assay to calculate the amount of protein, the CRM197-maleimid was stored in PBS buffer (pH 7.2, 1.0 mg/mL) for next step. According to the data of MALDI-TOF, the amount of maleimid function groups could be calculated. For example, when the molecular weight of CRM197-maleimid was 61841, the numbers of maleimide function groups on CRM197-maleimid were (61841-58326)/193=18.2.

Step C: The Synthesis of SSEA3/4 analog-CRM197 Conjugates

The CRM197-maleimids were dissolved in PBS buffer (pH 7.2, the concentration was 1.0 mg/mL) and then different amount of SSEA3/4 analog-SH (5.0 mg/mL in PBS buffer, pH 7.2) were added into the solution. The mixtures were stirred at room temperature for 2 hours. The SSEA3/4 analog-CRM197 conjugates were purified by using Amicon Ultra-0.5 (10 kDa) to remove the nonreactive SSEA3/4 analog-SH and sodium phosphate salt via dialysis. The obtained SSEA3/4 analog-CRM197 conjugates could be characterized by MALDI-TOF analysis to determine the carbohydrate incorporation rate. The nonreactive SSEA3/4 analog-SH could be recovered after reacting with DTT and purifying by LH-20 column chromatography.

TABLE 1

Carbohydrate incorporation rate of SSEA4 analog with CRM-197 via Sulfo-EMCS

| Code | Sugar | Molecular weight after glycosylation | (y) average incorporation rate |
| --- | --- | --- | --- |
| M1 | SSEA4 | 75465 | 8.84 |
| M2 | Neu5Gc_SSEA4 | 70750 | 5.83 |
| M3 | Ac-Alkynyl_SSEA4 | 68965 | 5.94 |
| M4 | Ac-Fluoride_SSEA4 | 69190 | 4.59 |
| M5 | Ac-Phenyl_SSEA4 | 75454 | 8.10 |
| M6 | Ac-Azido_SSEA4 | 70274 | 5.30 |
| M7 | 9'-Azido_SSEA4 | 76596 | 9.87 |
| M8 | Glc-azido_SSEA4 | 73047 | 8.00 |

Example 4

Syntheses of SSEA4-Gc-CRM197 Conjugates Via Sulfo-EMCS Crosslink

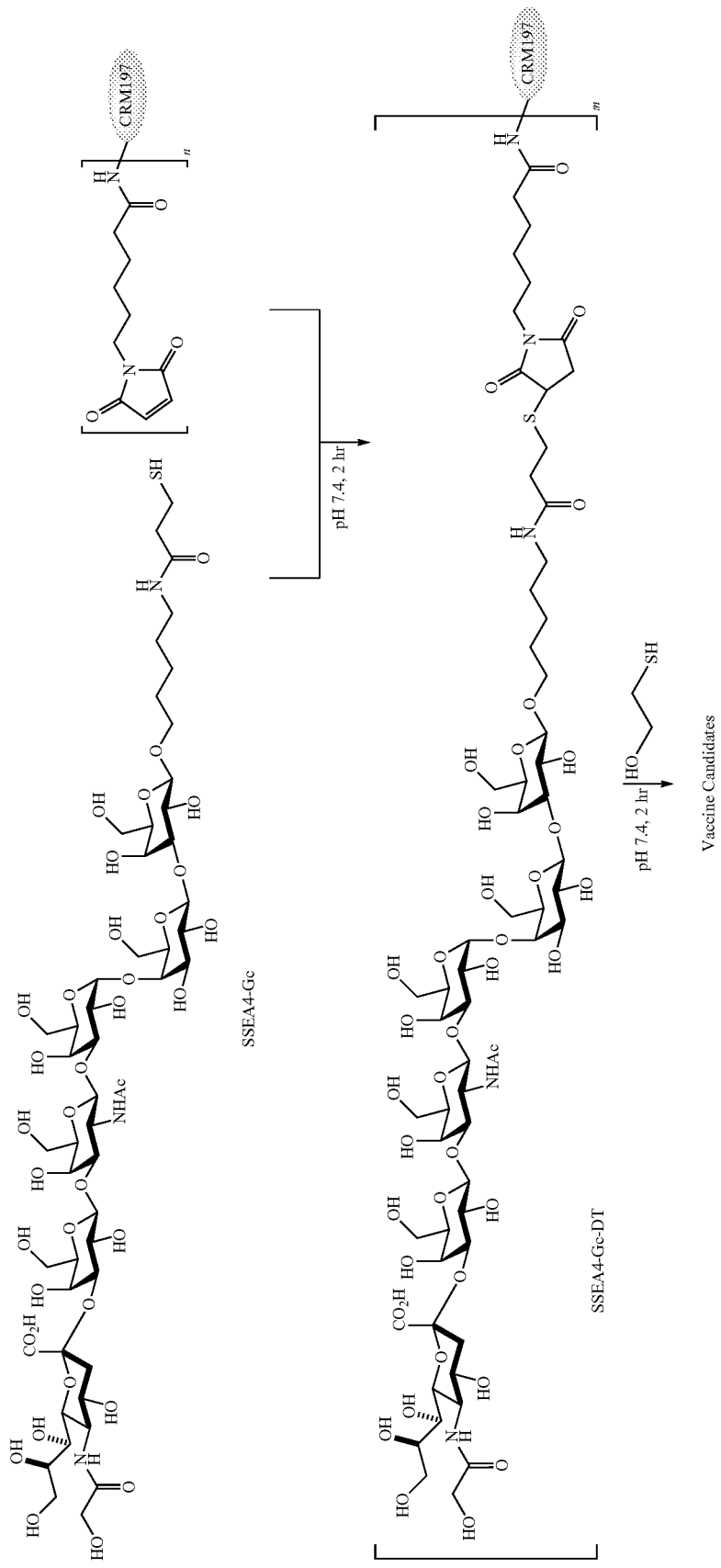

Step A: To modify SSEA4-Gc-NH2 into SSEA4-Gc-SH

DTSSP (5.0 mg, $8.22 \times 10^{-6}$ mol) was added to a flask of SSEA4-Gc-NH2 (5.0 mg, $4.01 \times 10^{-6}$ mol) in PBS buffer (pH 7.4, 1.0 mL) at room temperature. To monitor the pH value of solution by pH paper, NaOH (1 M/water) was added to the solution when the solution became neuter or acid. After the reaction was stirred at room temperature for 12 hours, DTT (5.0 mg, $32.41 \times 10^{-6}$ mol) was added to the solution at room temperature. The solution was kept stirring at 40° C. for 1 hour, and then the solvent was removed under reduced pressure. The residue was purified by LH-20 column chromatography to give SSEA4-Gc-SH (5.0 mg, 93%)

Step B: To modify CRM197 into CRM197-maleimide.

After the salt of commercial CRM197 (1.0 mg) was removed via alternate dissolving in water and dialyzing (Amicon Ultra-0.5, 10 kDa,), the residue was dissolved in PBS buffer (pH 6.5, 1.0 mL) and transferred into a sample vial. Sulfo-EMCS (1.0 mg, $8.22 \times 10^{-6}$ mol) was added to the solution, and then the reaction was kept stirring at room temperature for 2 hours. The mixture was purified by Amicon Ultra-0.5 (10 kDa). After using MALDI-TOF to check the molecular weight and BCA assay to calculate the amount of protein, the CRM197-maleimid was stored in PBS buffer (pH 7.2, 1.0 mg/mL) for next step. According to the data of MALDI-TOF, the amount of maleimid function groups could be calculated. For example, when the molecular weight of CRM197-maleimid was 61841, the numbers of maleimide function groups on CRM197-maleimid were (61841−58326)/193=18.2.

The CRM197-maleimids were dissolved in PBS buffer (pH 7.2, the concentration was 1.0 mg/mL) and then different amount of SSE4Gc-SH (5.0 mg/mL in PBS buffer, pH 7.2) were added into the solution. The mixtures were stirred at room temperature for 2 hours. The SSEA4-Gc-CRM197 conjugates were purified by using Amicon Ultra-0.5 (10 kDa) to remove the nonreactive SSEA4-Gc-SH and sodium phosphate salt via dialysis. The obtained SSEA4-Gc-CRM197 conjugates could be characterized by MALDI-TOF analysis to determine the carbohydrate incorporation rate as showing in Table 2. The nonreactive SSEA4-Gc-SH could be recovered after reacting with DTT and purifying by LH-20 column chromatography.

Step C: To trap the nonreactive maleimides of CRM197-maleimide

The SSEA4-Gc-CRM197 conjugates were dissolved in PBS buffer (pH 7.2, the concentration was 1.0 mg/mL) and 10.0 equivalent of 2-mercaptoethanol (5 mg/mL, PBS buffer, pH 7.2) were added to the solution. The mixtures were stirred at room temperature for 2 hours. The SSEA4-Gc-CRM197 conjugates were purified by using Amicon Ultra-0.5 (10 kDa) to remove the nonreactive 2-mercaptoethanol and sodium phosphate salt via dialysis and then lyophilized to a white powder.

TABLE 2

Conjugation of CRM197 with SSEA4-Gc

| | CRM197 (μg) | Number of Linkers | Amount of Linkers (mol) | PBS Buffer (pH 7.4, μL) | SSEA4-Gc (5 mg/mL) | Reaction Time | Number of Sugars | HSC$_2$H$_4$OH (5 mg/mL) 10.0 eq. | CRM197 (μg) |
|---|---|---|---|---|---|---|---|---|---|
| 1 | 1388 | 21.9 | $5.21 \times 10^{-7}$ | 1000 | 28.1 μL (0.2 eq.) | 2 hr | 2.0 | 81.4 μl | 1550.4 |
| 2 | 694 | 21.9 | $2.61 \times 10^{-7}$ | 500 | 28.2 μL (0.4 eq.) | 2 hr | 4.2 | 40.8 μL | 657.4 |
| 3 | 694 | 21.9 | $2.61 \times 10^{-7}$ | 500 | 56.4 μL (0.8 eq.) | 2 hr | 6.5 | 40.8 μL | 665.0 |
| 4 | 694 | 21.9 | $2.61 \times 10^{-7}$ | 500 | 84.5 μL (1.2 eq.) | 2 hr | 6.9 | 40.8 μL | 627.0 |
| 5 | 694 | 21.9 | $2.61 \times 10^{-7}$ | 500 | 140.9 μL (2.0 eq.) | 2 hr | 7.1 | 40.8 μL | 615.6 |
| 6 | 694 | 21.9 | $2.61 \times 10^{-7}$ | 500 | 281.8 μL (4.0 eq.) | 2 hr | 7.0 | 40.8 μL | 665.0 |
| 7 | 694 | 21.9 | $2.61 \times 10^{-7}$ | 500 | 704.4 μL (10.0 eq.) | 2 hr | 6.8 | 40.8 μL | 695.4 | a) M.W of CRM197 = 58326 → 1000 μg = $0.1715 \times 10^{-7}$ mol
b) M.W. of SSEA4-Gc-SH = 1349.479 → 5 mg/mL = $37.051 \times 10^{-7}$ mol/mL
c) M.W. of 2-Mercaptoethanol = 78.13 → 5 mg/mL = $639.91 \times 10^{-7}$ mol/mL Example 5

SSEA4 Analog-CRM197 Conjugate Via SBAP Crosslink

Scheme 9.

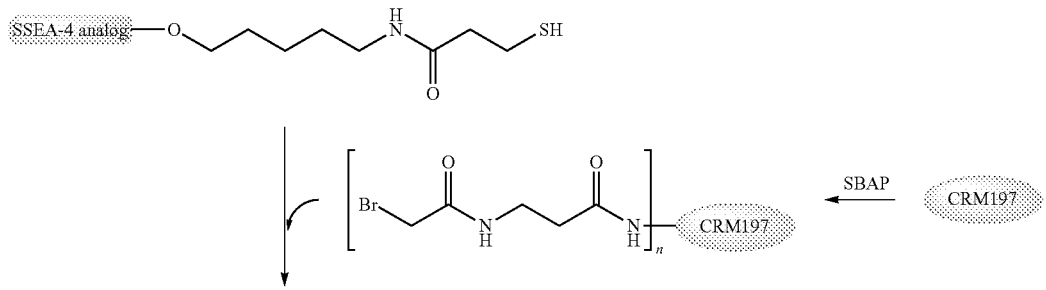

-continued

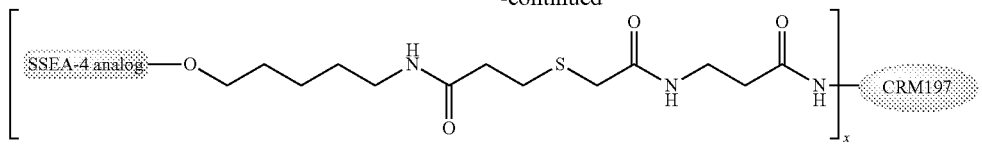

CRM-197 was dissolved in 0.1 M phosphate buffer pH 7.4 (~1 mg/ml), and SBAP (1.0 mg) was added to the solution. The solution was stirred gently for 2 hrs at room temperature. The mixture was then diluted with PBS buffer and centrifuge against 5 changes of 0.1 M phosphate buffer pH 7.4 by Amicon Ultra-0.5 (10 kDa, 2×). The obtained modified CRM-197 can be characterized by MALDI-TOF (positive mode, matrix was sinapinic acid, $H_2O$) analysis to determine the SBAP incorporation rate.

Modified CRM-197 was dissolved in 0.1 M phosphate buffer pH 8.0 (~1 mg/ml), and SSEA4-SH analog was added to the solution. The mixture was stirred for 1 day at room temperature. The mixture was then diluted with PBS buffer and centrifuge against 5 changes of 0.1 M PBS buffer pH 7.4 by Amicon Ultra-0.5 (10 kDa, 2×). The obtained sugar-protein conjugate could be characterized by MALDI-TOF (positive mode, matrix was sinapinic acid, $H_2O$) analysis to determine the carbohydrate incorporation rate. (Scheme 9)

TABLE 3

Carbohydrate incorporation rate of SSEA4 analog with CRM-197 via SBAP

| Code | Sugar | Molecular weight after glycosylation | (x) average incorporation rate |
|---|---|---|---|
| S1 | SSEA4 | 68212 | 4.79 |
| S2 | Neu5Gc__SSEA4 | 67651 | 4.84 |
| S3 | Ac-Alkynyl__SSEA4 | 70308 | 5.70 |
| S4 | Ac-Fluoride__SSEA4 | 69309 | 5.01 |
| S5 | Ac-Phenyl__SSEA4 | 68891 | 5.05 |
| S6 | Ac-Azido__SSEA4 | 68359 | 4.50 |
| S7 | 5'-Azido__SSEA4 | 71638 | 7.06 |
| S8 | 9'-Azido__SSEA4 | 72545 | 7.90 |
| S9 | Glc-azido__SSEA4 | 67131 | 3.9 |
| S10 | NHBz__SSEA4 | 69636 | 5.50 |

Example 6

SSEA4 Analog-CRM197 Conjugate Via Reductive Amination Crosslink

Scheme 10

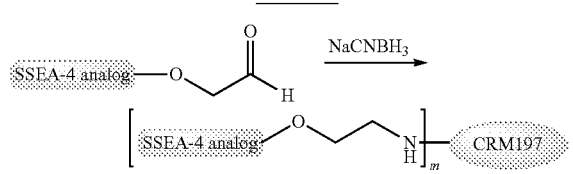

In certain embodiments, CRM197 was dissolved in 0.1 M phosphate buffer (pH 6-9) (~1 mg/ml), and enough quantity SSEA4-aldehyde analogs and $NaCNBH_3$ were added to the solution. The solution was stirred gently for 3 days at room temperature. The mixture was then diluted with deionized water and centrifuge against 5 changes of 0.1 M phosphate buffer pH 7.4 by Amicon Ultra-0.5 (10 kDa, 2×). The obtained sugar-protein conjugate was characterized by MALDI-TOF (positive mode, matrix was sinapinic acid, $H_2O$) analysis to determine the carbohydrate incorporation rate. (Scheme 10)

TABLE 4

Carbohydrate incorporation rate of SSEA4 analog with CRM-197 via reductive amination

| Code | Sugar | Molecular weight after glycosylation | (m) average incorporation rate |
|---|---|---|---|
| R1 | SSEA4 | 69025 | 8.89 |
| R2 | Neu5Gc__SSEA4 | 65154 | 5.6 |
| R3 | Ac-Fluoride__SSEA4 | 69315 | 9 |
| R4 | Ac-Phenyl__SSEA4 | 71329 | 10.1 |
| R5 | Ac-Azido__SSEA4 | 67765 | 7.6 |
| R6 | 9'-Azido__SSEA4 | 67635 | 7.58 |
| R7 | NHBz__SSEA4 | 67124 | 6.95 |

Example 7

Immunization Determination of the SSEA4 Analog-CRM197 Conjugates

Exemplary Method

To demonstrate the efficacy/immunogenicity of the SSEA4 analog CRM197 conjugates (S1~S10), female C57BL/6 mice (n=5 for each group) were vaccinated intramuscularly with 0.5 µg of SSEA4 analog CRM197-conjugates combining the use of 2.0 µg of glycolipid adjuvant. Control mice were given only phosphate buffer saline with 2.0 µg of glycolipid adjuvant. The vaccination was conducted at biweekly intervals for 2 months, and the antisera from the immunized mice were collected one week after each vaccination. The antibody titers against SSEA4 were examined by ELISA using SSEA4 immobilized 96-well titer plates. ELISA was conducted using SSEA4 immobilized 96-well titer plate. Briefly, the diluted antisera were incubated with the immobilized SSEA4 at room temperature for 2 hr. After the washing cycle, the captured anti-SSEA4 antibodies were then detected using HPR-conjugated anti-IgG or IgM specific antibody.

To determine if the glycan-protein conjugation method would interfere the immune response, native SSEA4 was conjugated with CRM197 through EMCS linker (Ml), SBAP linker (51) or reductive amination (R1) and used for immunogenicity study as described above.

Representative Result

Figure 3A:
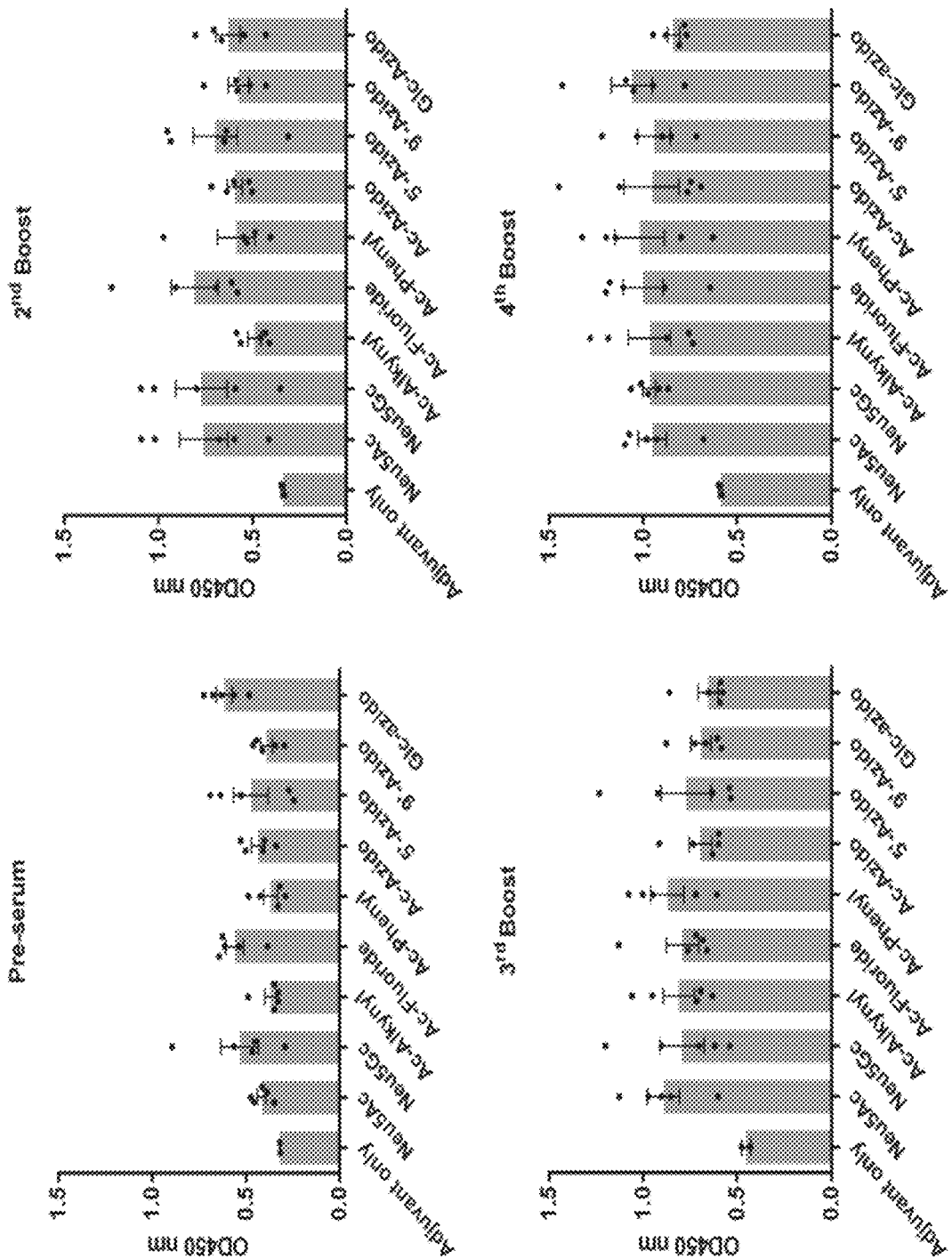
FIG. 3A: Native SSEA4, as well as all eight SSEA4 analogs, could elicit IgG antibodies against SSEA4 when combining the use of Gal-C34.
Figure 3B:
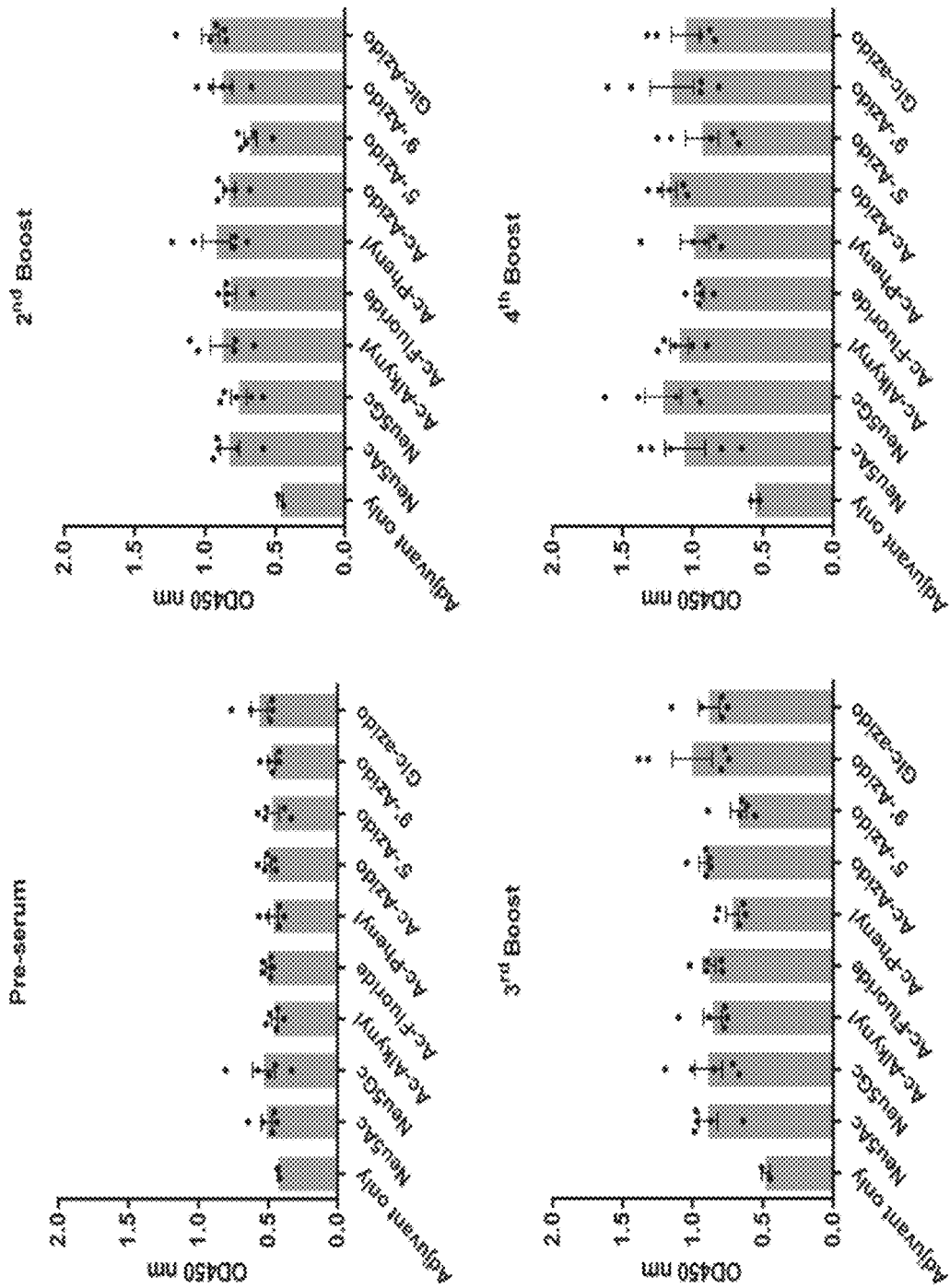
FIG. 3B: Native SSEA4, as well as all eight SSEA4 analogs, could elicit IgM antibodies against SSEA4 when combining the use of Gal-C34.
Figure 4A:
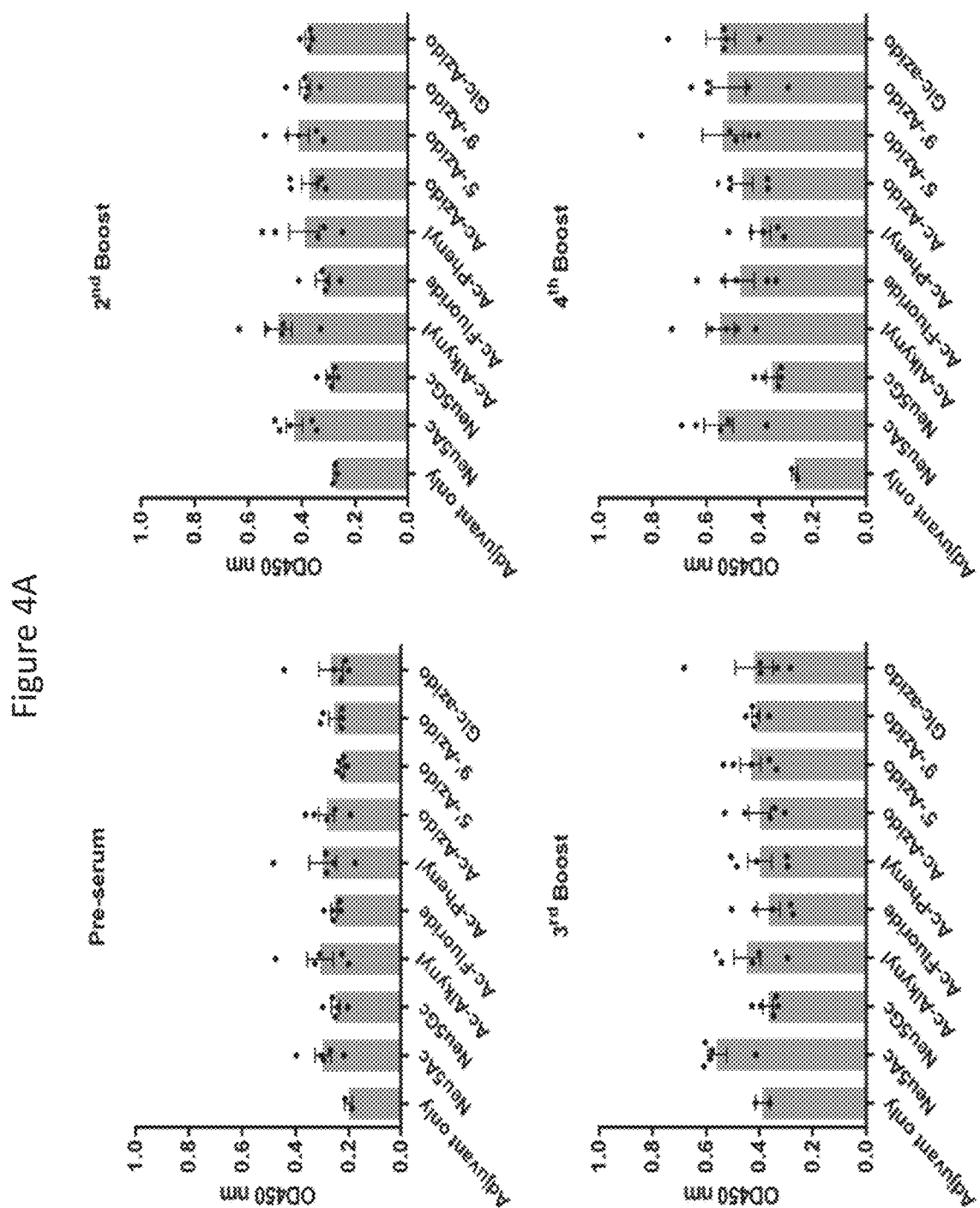
FIG. 4A: Native SSEA4, as well as all eight SSEA4 analogs, could elicit IgG antibodies against SSEA4 when combining the use of Glc-C34.
Figure 4B:
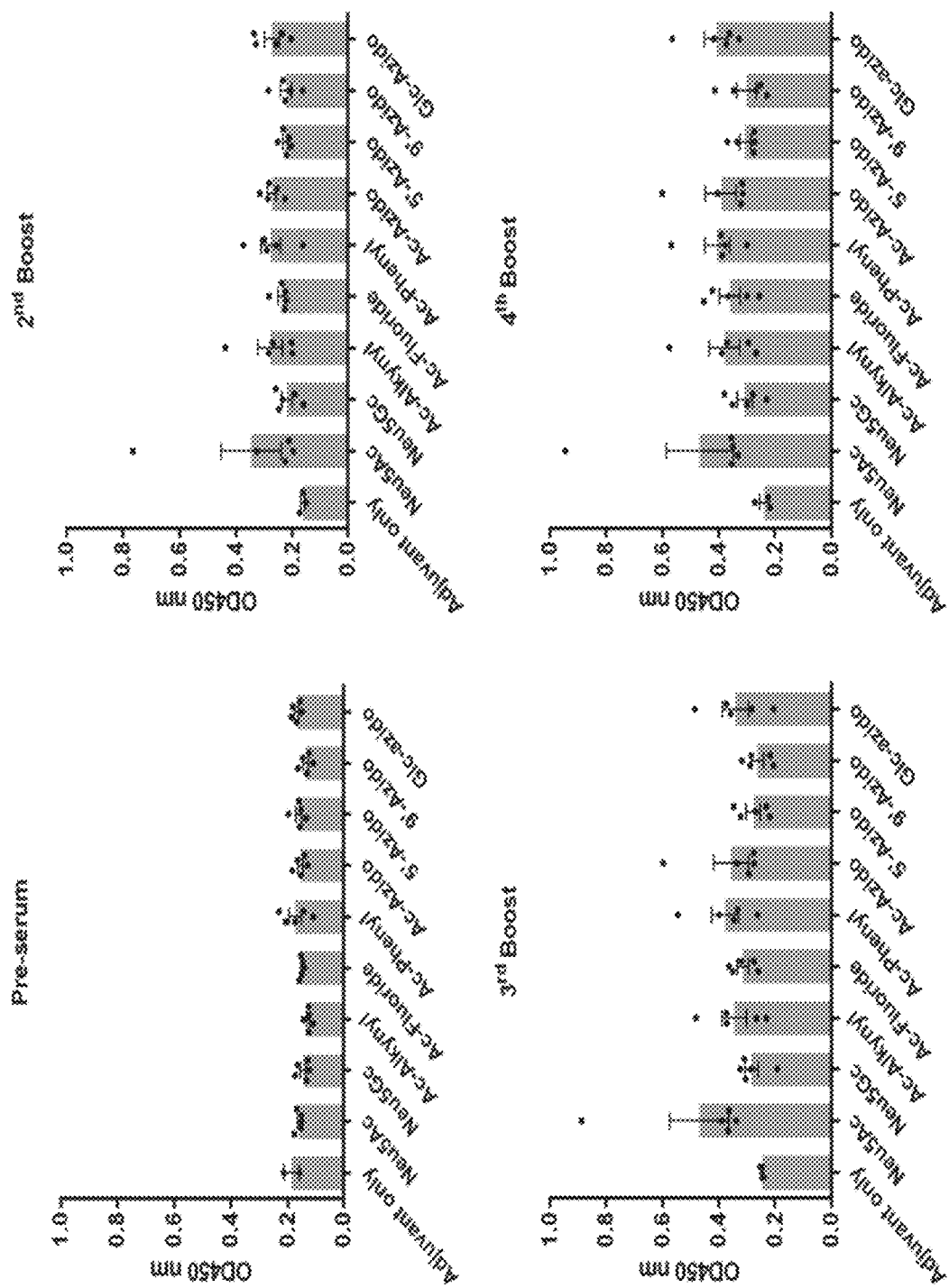
FIG. 4B: Native SSEA4, as well as all eight SSEA4 analogs, could elicit IgM antibodies against SSEA4 when combining the use of Glc-C34.

After four times of immunization, native SSEA4, as well as all eight SSEA4 analogs, could positively elicit both IgG (FIG. 3A) and IgM (FIG. 3B) antibodies against SSEA4 when combining the use of Gal-C34 adjuvant. There is no significant difference in the titers of anti-SSEA4 IgG and IgM antibodies among different analog groups. In addition, Glc-C34 can also be used as vaccine adjuvant for inducing both IgG (FIG. 4A) and IgM (FIG. 4B) antibodies against SSEA4 when co-administering with native SSEA4 and the other analogs.

Figure 5:
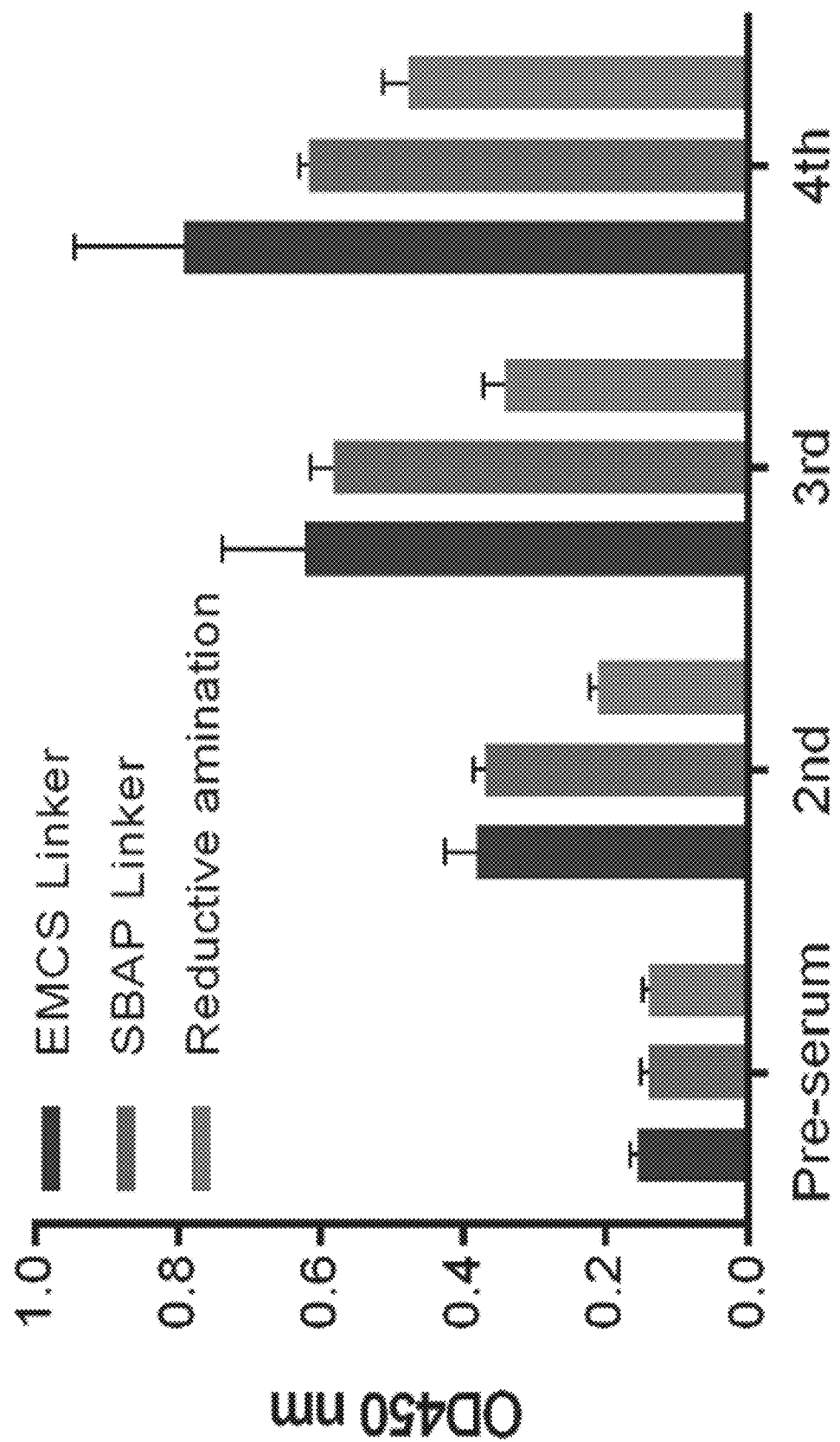
FIG. 5: The glycan-protein conjugation method affects the immune response.

Furthermore, the results shown in FIG. 5 indicated that the glycan-protein conjugation method can affect the immune response. Combining the use of Gal-C34, the SSEA4-EMCS-CRM197 (Ml) elicited a higher anti-SSEA4 IgG antibody titer when comparing to SSEA4-SBAP-CRM197 (S1) and SSEA4-CRM197 (conjugated through reductive amination, R1).

Example 8

Immunogenicity Study of the SSEA4 Analogs CRM197-conjugates

To demonstrate the immunogenicity of the SSEA4 analog CRM197-conjugates, five female BALB/c mice were immunized intramuscularly with 2 µg of SSEA4 analog CRM197-conjugates and 2 µg of the glycolipid adjuvant C34 three times at biweekly intervals. In the previous study, the anti-GH antibodies titer was low with SSEA4 analog-protein conjugates alone without any adjuvants. The antisera from each immunogen were obtained ten days after the third immunization and were tested on the glycan microarray containing 94 chemically synthesized glycans, including globo series glycans and other tumor-associated carbohydrate antigens. Because some chemical modifications were carried out on the glycan, some functional linkers were also included in the glycan array to check the cross reactivity.

Antibodies induced by the SSEA4-Gc CRM197-conjugates were specifically recognized by SSEA4-Gc, native SSEA4 or SSEA4 tetrasaccharide fragments but not by other TACAs and functional linkers. The sera obtained from the glycoconjugates induced high IgG antibody titers, indicating a T-cell-dependent immune response. Interestingly, no significant IgM production was observed for SSEA4-Gc or native SSEA4. Regarding the IgG level against GloboH, the titers of antibodies induced by SSEA4-Gc CRM197 was much higher than the nature form native SSEA4-CRM197 conjugate. Among them the 6.9 molecule of SSEA4-Gc conjugated with one molecule of CRM197 can induce the highest antibody titers.

Mice Dosage and Immunization Schedule

For comparing the immunogenicity of SSEA4 analog CRM197, ten groups of five mice (8-week-old female Balb/c mice, BioLASCO, Taiwan) were immunized intramuscularly with glycolipid C34. Three immunizations were given at 2-week intervals. Each vaccination contained 2 µg SSEA4 analog and 2 µg C34. Control mice were injected with phosphate buffer saline (PBS). Mice were bled before the first immunization (preimmune) and 10 days after the third immunization. All of the sera were obtained by centrifugation at 4,000×g for 10 min. The serologic responses were analyzed by glycan microarray.

Serologic Assay with Glycan Array

Mouse sera were diluted with 1% BSA/PBST buffer (PBST buffer: PBS and 0.05% Tween-20, pH 7.4). The glycan microarray was blocked with Superblock blocking buffer (Pierce) for 1 h at 4° C. and washed three times with PBST buffer before use. The serum dilutions were then introduced to the glycan microarray and incubated at 4° C. for 1 h. Excess serum antibodies were washed out and the microarrays were incubated individually with Alexa Fluor 647-conjugated goat anti-mouse IgG antibody or DyLight 649-conjugated goat anti-mouse IgM antibody as the 2nd antibody at 4° C. in dark for 1 h. The slides were then washed three times with PBST and scanned at 635 nm wavelength with a microarray fluorescence chip reader (GenePix 4300 A; Molecular Devices Corporation) and scanned images were analyzed with GenePix Pro-6.0 analysis software (Axon Instruments, Union City, Calif., USA).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

We claim:

1. An immunogenic composition comprising:
(a) a glycan conjugate including a carrier and one or more glycans, and optionally
(b) an adjuvant;
wherein each of the one or more glycans is conjugated with the carrier through a linker,
and the glycan conjugate has the structure depicted in formula (III):

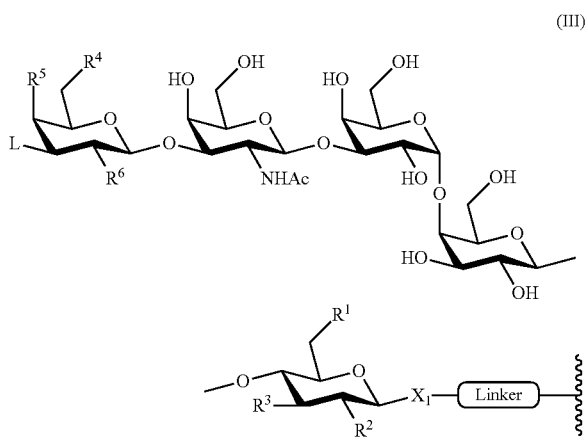

wherein:
$X_1$ is selected from —OR, wherein R is selected from a hydroxyl protecting group, optionally substituted $C_{1-10}$ alkyl, optionally substituted aryl, optionally substituted acyl, and optionally substituted imidoyl; or
$X_1$ is selected from —SR, wherein R is selected from a thiol protecting group, optionally substituted $C_{1-10}$ alkyl, optionally substituted aryl, optionally substituted acyl, and optionally substituted imidoyl;
each instance of $R^1$, $R^2$, $R^3$, $R^4$, and $R^5$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;

$R^6$ is selected from hydrogen, halogen, optionally substituted alkyl, optionally substituted alkenyl, optionally substituted alkynyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;

L is —OH;

each instance of $R^A$ is independently selected from hydrogen, optionally substituted alkyl, optionally substituted alkenyl, optionally substituted alkynyl, optionally substituted heterocyclyl, and optionally substituted aryl;

wherein, when $R^6$ is —$OR_A$, $R_A$ is not substituted heterocycle;

each instance of $R^B$ is independently selected from hydrogen, optionally substituted alkyl, optionally substituted alkenyl, optionally substituted alkynyl, optionally substituted heterocyclyl, and optionally substituted aryl; and provided the glycan conjugate is not one of the formula (III-a):

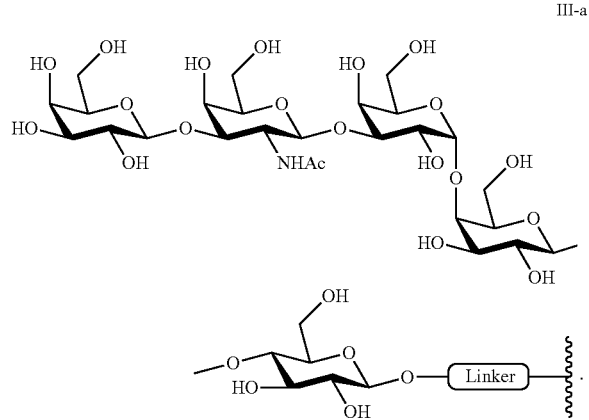

2. An immunogenic composition comprising:
(a) a glycan conjugate including a carrier and one or more glycans, and optionally
(b) an adjuvant;
wherein each of the one or more glycans is conjugated with the carrier through a linker,
and the glycan conjugate has the structure depicted in formula (III):

wherein:
$X_1$ is selected from —OR, wherein R is selected from a hydroxyl protecting group, optionally substituted $C_{1-10}$ alkyl, optionally substituted aryl, optionally substituted acyl, and optionally substituted imidoyl; or
$X_1$ is selected from —SR, wherein R is selected from a thiol protecting group, optionally substituted $C_{1-10}$ alkyl, optionally substituted aryl, optionally substituted acyl, and optionally substituted imidoyl;

each instance of $R^1$, $R^2$, $R^3$, $R^4$, and $R^5$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;

$R^6$ is selected from hydrogen, halogen, optionally substituted alkyl, optionally substituted alkenyl, optionally substituted alkynyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;

L is selected from hydrogen, halogen, optionally substituted alkyl, optionally substituted alkenyl, optionally substituted alkynyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, —$NHSO_2R^B$, and substituted heterocyclyl;

each instance of $R^A$ is independently selected from hydrogen, optionally substituted alkyl, optionally substituted alkenyl, optionally substituted alkynyl, optionally substituted heterocyclyl, and optionally substituted aryl;

each instance of $R^B$ is independently selected from hydrogen, optionally substituted alkyl, optionally substituted alkenyl, optionally substituted alkynyl, optionally substituted heterocyclyl, and optionally substituted aryl;

wherein at least one instance of $R^1$, $R^2$, $R^3$, $R^4$, $R^5$ and $R^6$ is selected from —$N_3$ or —F.

3. An immunogenic composition comprising:
(a) a glycan conjugate including a carrier and one or more glycans, and optionally
(b) an adjuvant;
wherein each of the one or more glycans is conjugated with the carrier through a linker,
and the glycan conjugate has the structure depicted in formula (IV):

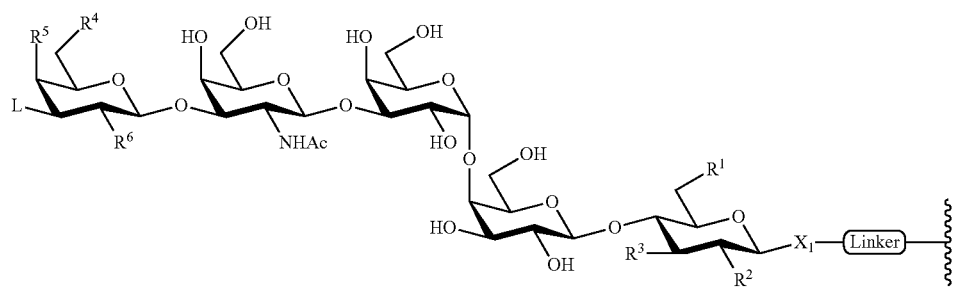

(III)

(IV)

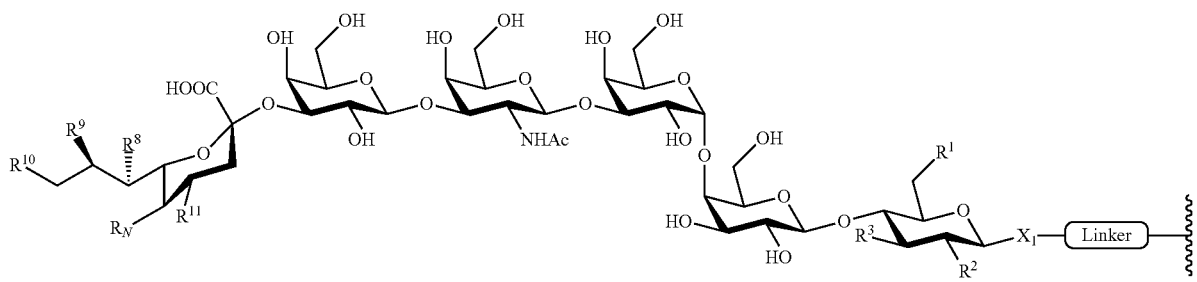

wherein:
  X₁ is selected from —OR, wherein R is selected from a hydroxyl protecting group, optionally substituted $C_{1-10}$ alkyl, optionally substituted aryl, optionally substituted acyl, and optionally substituted imidoyl; or
  X₁ is selected from —SR, wherein R is selected from a thiol protecting group, optionally substituted $C_{1-10}$ alkyl, optionally substituted aryl, optionally substituted acyl, and optionally substituted imidoyl;
  each instance of $R^1$, $R^2$, $R^3$, $R^8$, $R^9$, $R^{10}$, and $R^{11}$ is independently selected from hydrogen, halogen, optionally substituted alkyl, optionally substituted alkenyl, optionally substituted alkynyl, optionally substituted heterocyclyl, optionally substituted aryl, —N₃, —NO₂, —N($R^B$)₂, —N($R^A$)C(O)$R^A$, —O$R^A$, —OC(O)$R^A$, —S$R^A$, —C(O)N($R^B$)₂, —CN, —C(O)$R^A$, —C(O)O$R^A$, —S(O)$R^A$, —SO₂$R^A$, —SO₂N($R^B$)₂, and —NHSO₂$R^B$;
  $R^N$-is selected from —N₃, —NO₂, —N($R^B$)₂, —N($R^A$)C(O)$R^A$, —O$R^A$, —OC(O)$R^A$, —S$R^A$, —C(O)N($R^B$)₂, —CN, —C(O)$R^A$, —C(O)O$R^A$, —S(O)$R^A$, —SO₂$R^A$, —SO₂N($R^B$)₂, and —NHSO₂$R^B$;
  each instance of $R^A$ is independently selected from hydrogen, optionally substituted alkyl, optionally substituted alkenyl, optionally substituted alkynyl, optionally substituted heterocyclyl, and optionally substituted aryl; and
  each instance of $R^B$ is independently selected from hydrogen, optionally substituted alkyl, optionally substituted alkenyl, optionally substituted alkynyl, optionally substituted heterocyclyl, and optionally substituted aryl; and
  provided the glycan conjugate is not formula (III-b):

III-b

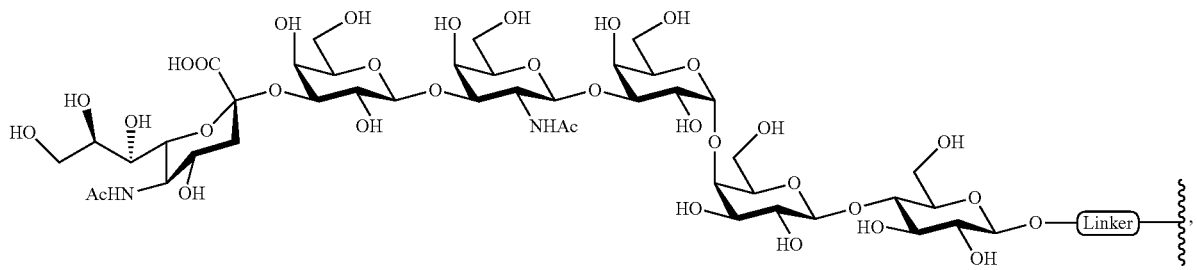

and
wherein at least one instance of $R^1$, $R^2$, $R^3$, $R^8$, $R^9$, $R^{10}$, $R^{11}$ and $R_N$ is selected from —N₃ or —F.

4. The immunogenic composition of claim 3 wherein the glycan conjugate has the following structure:

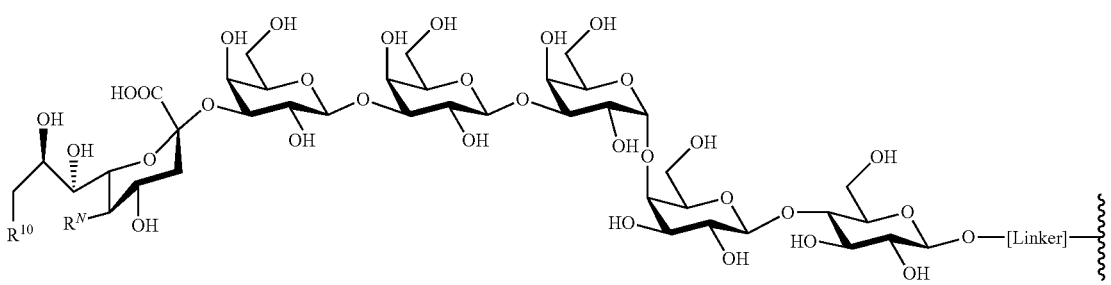

wherein:
R$^{10}$ is selected from hydrogen, halogen, optionally substituted alkyl, optionally substituted alkenyl, optionally substituted alkynyl, optionally substituted heterocyclyl, optionally substituted aryl, —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$; wherein R$^{12}$ is H, OH, or halogen;

R$_N$ is selected from —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$;

each instance of R$^A$ is independently selected from hydrogen, optionally substituted alkyl, optionally substituted alkenyl, optionally substituted alkynyl, optionally substituted heterocyclyl, and optionally substituted aryl; and each instance of R$^B$ is independently selected from hydrogen, optionally substituted alkyl, optionally substituted alkenyl, optionally substituted alkynyl, optionally substituted heterocyclyl, and optionally substituted aryl.

5. The immunogenic composition of any of claim 1, 2, 4 or 3, wherein the carrier is a protein, a lipid, a lipolyzed protein, a virus, a peptide, or a dendrimer of glycopeptides.

6. The immunogenic composition of claim 5, wherein the carrier is a protein selected from the group consisting of tetanus toxoid (TT), diphtheria toxoid (DT), diphtheria toxin cross-reacting material 197 (CRM197), fragment C of TT, Keyhole limpet hemocyanin (KLH), bovine serum albumin (BSA), protein D, outer-membrane protein (OMP) and pneumolysin.

7. The immunogenic composition of claim 6, wherein the carrier protein is selected from the group consisting of TT, DT and CRM197.

8. The immunogenic composition of claim 7, wherein the glycan conjugate is of the formula (IV-a) or (IV-b):

9. The immunogenic composition of any of claim 1, 2, 4, or 3, wherein the linker is a hetero- or homo-bifunctional linker.

10. The immunogenic composition of any one of claim 1, 2, 4, or 3, wherein the adjuvant is a glycolipid capable of binding a CD1d molecule on a dendritic cell.

11. The immunogenic composition of any one of claim 1, 2, 4, or 3, wherein the adjuvant is C34, 7DW8-5, C17, C23, Gluco-C34, Aluminum salt, Squalene, MF59, or QS-21.

12. The immunogenic composition of any one of claim 1, 2, 4, or 3, wherein the immunogenic composition is capable of eliciting an immune response against a cancer cell.

13. The immunogenic composition of claim 12, wherein the cancer cell is selected from the group consisting of a brain cancer cell, a lung cancer cell, a breast cancer cell, an oral cancer cell, an esophagus cancer cell, a stomach cancer cell, a liver cancer cell, a bile duct cancer cell, a pancreatic cancer cell, a colon cancer cell, a kidney cancer cell, a bone cancer cell, a skin cancer cell, a cervical cancer cell, an ovarian cancer cell, and a prostate cancer cell.

14. The immunogenic composition of claim 12, wherein the immune response includes generation of antibodies that specifically bind to one or more of the antigens selected from the group consisting of SSEA3 and SSEA4.

15. The immunogenic composition of claim 14, wherein the antibodies neutralize one or more of SSEA3 and SSEA4 antigen expressed on the surface of cancer cells or cancer stem cells.

16. The immunogenic composition of claim 14, wherein the antibodies predominantly includes IgG antibodies.

17. A cancer vaccine, comprising a therapeutically effective amount of the immunogenic composition of any one of claim 1, 2, 4, or 3 and a pharmaceutically acceptable excipient.

(IV-a)

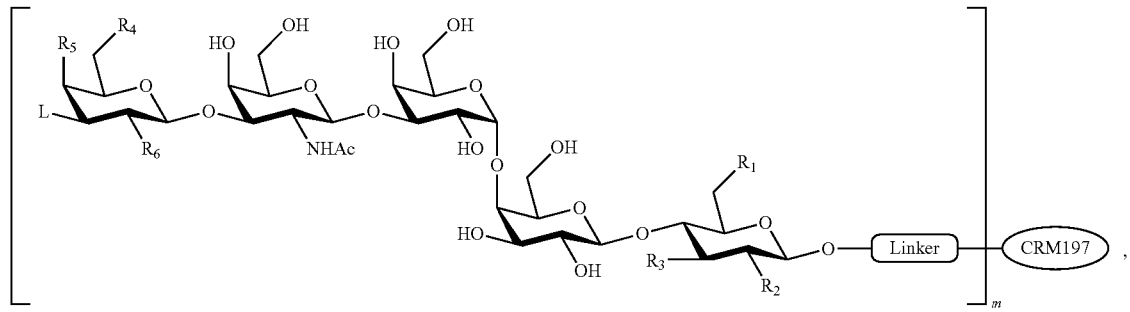

wherein L is —OH, and at least one instance of R$^1$, R$^2$, R$^3$, R$^4$, R$^5$, and R$^6$ is selected from —N$_3$ or —F; or (IV-b)

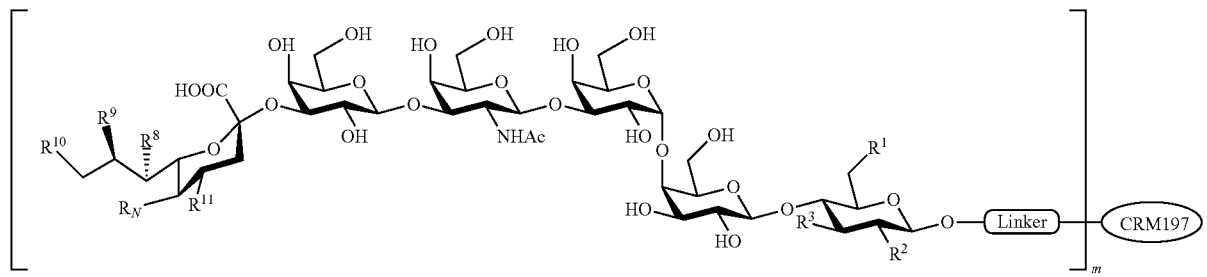

wherein m is an integer of 1 to 40, inclusive,
at least one instance of R$^1$, R$^2$, R$^3$, R$^8$, R$^9$, R$^{10}$, R$^{11}$ and R$_N$ is selected from —N$_3$ or —F.

18. The cancer vaccine of claim 17, wherein the cancer vaccine is able to induce an anti-cancer immune response in a subject.

19. A method of treating cancer in a subject in need thereof, wherein the method comprises administering a therapeutically effective amount of the immunogenic composition of any one of claim 1, 2, 4, or 3.

20. The method of claim 19 wherein the vaccine is co-administered in combination with another therapeutic agent.

21. The method of claim 19, wherein the cancer is selected from the group consisting of brain cancer, lung cancer, breast cancer, oral cancer, esophageal cancer, stomach cancer, liver cancer, bile duct cancer, pancreatic cancer, colon cancer, kidney cancer, bone cancer, skin cancer, cervical cancer, ovarian cancer, and prostate cancer.

22. The method of claim 21, wherein the cancer cell expresses SSEA3 and/or SSEA4 antigen on the surface of the cell.

23. The method of claim 22, wherein the subject is a human.

24. The method of claim 19, wherein the immunogenic composition or the cancer vaccine is administered subcutaneously.

25. A method for making the immunogenic composition of claim 1, the method comprising:
providing a carrier;
conjugating one or more glycan to the carrier by a conjugation reaction;
wherein the glycan has the structure depicted in formula (III):

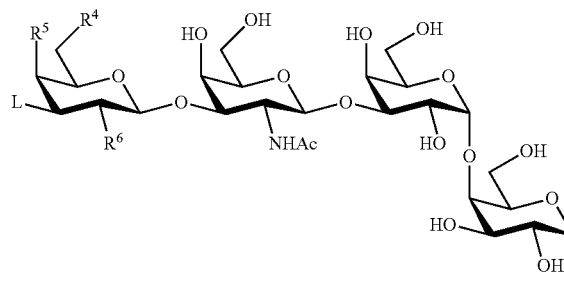

(III)

wherein:
X$_1$ is selected from —OR, wherein R is selected from a hydroxyl protecting group, optionally substituted C$_{1-10}$ alkyl, optionally substituted aryl, optionally substituted acyl, and optionally substituted imidoyl; or
X$_1$ is selected from —SR, wherein R is selected from a thiol protecting group, optionally substituted C$_{1-10}$ alkyl, optionally substituted aryl, optionally substituted acyl, and optionally substituted imidoyl;
each instance of R$^1$, R$^2$, R$^3$, R$^4$, and R$^5$ is independently selected from hydrogen, halogen, optionally substituted alkyl, optionally substituted alkenyl, optionally substituted alkynyl, optionally substituted heterocyclyl, optionally substituted aryl, —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$;

R$^6$ is selected from hydrogen, halogen, optionally substituted alkyl, optionally substituted alkenyl, optionally substituted alkynyl, optionally substituted aryl, —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$;

L is selected from —OH or of the formula:

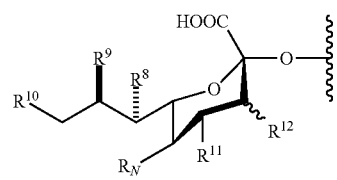

wherein R$^8$, R$^9$, R$^{10}$, R$^{11}$, and R$^{12}$ are independently selected from: hydrogen, halogen, optionally substituted alkyl, optionally substituted alkenyl, optionally substituted alkynyl, optionally substituted aryl, —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_{2R}{}^B$;

R$_N$ is selected from —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_{2R}$R$^B$;

each instance of R$^A$ is independently selected from hydrogen, optionally substituted alkyl, optionally substituted alkenyl, optionally substituted alkynyl, optionally substituted heterocyclyl, and optionally substituted aryl;

wherein, when R$^6$ is —OR$_A$, R$_A$ is not substituted heterocycle;

each instance of R$^B$ is independently selected from hydrogen, optionally substituted alkyl, optionally substituted alkenyl, optionally substituted alkynyl, optionally substituted heterocyclyl, and optionally substituted aryl; and provided the glycan is not of the formulae (I-a) or (I-b):

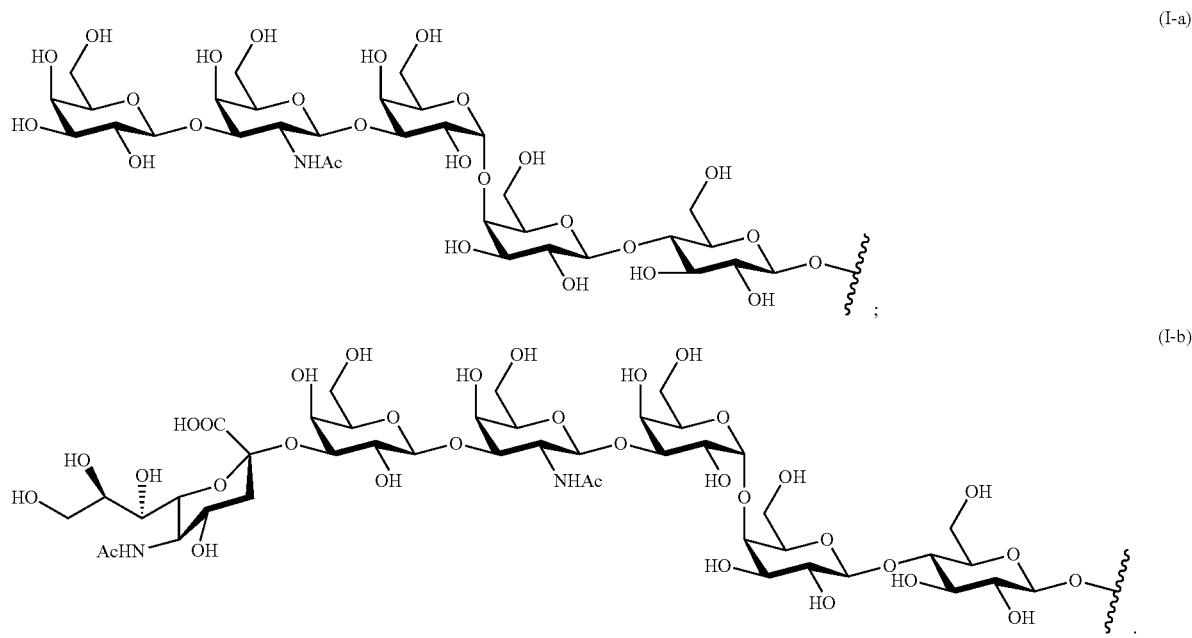

26. A compound having the formula (I):

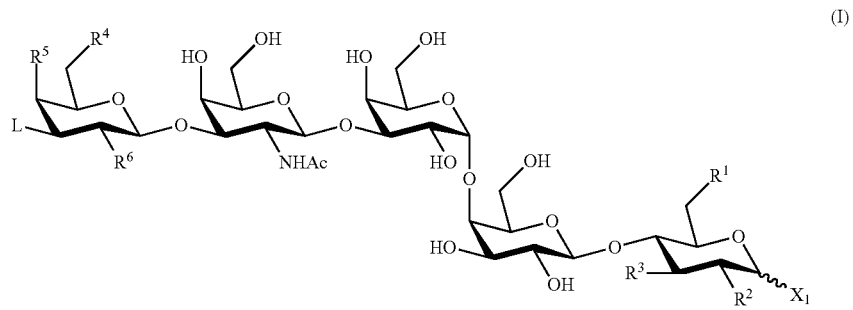

or a salt thereof,
wherein:
  $X_1$ is selected from —OR, wherein R is selected from a hydroxyl protecting group, optionally substituted $C_{1-10}$ alkyl, optionally substituted aryl, optionally substituted acyl, and optionally substituted imidoyl; or
  $X_1$ is selected from —SR, wherein R is selected from a thiol protecting group, optionally substituted $C_{1-10}$ alkyl, optionally substituted aryl, optionally substituted acyl, and optionally substituted imidoyl;
  each instance of $R^1$, $R^2$, $R^3$, $R^4$, and $R^5$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;
  $R^6$ is selected from hydrogen, halogen, optionally substituted alkyl, optionally substituted alkenyl, optionally substituted alkynyl, optionally substituted aryl, —$N_3$, —$NO_2$, —$N(R^B)_2$, —$N(R^A)C(O)R^A$, —$OR^A$, —OC(O) $R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;
  L is selected from hydrogen, halogen, optionally substituted alkyl, optionally substituted alkenyl, optionally substituted alkynyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, —$NHSO_2R^B$, and substituted heterocyclyl;
  each instance of $R^A$ is independently selected from hydrogen, optionally substituted alkyl, optionally substituted alkenyl, optionally substituted alkynyl, optionally substituted heterocyclyl, and optionally substituted aryl;
  wherein, when $R^6$ is —$OR_A$, $R_A$ is not substituted heterocycle;
  each instance of $R^B$ is independently selected from hydrogen, optionally substituted alkyl, optionally substituted alkenyl, optionally substituted alkynyl, optionally substituted heterocyclyl, and optionally substituted aryl; and
  provided the compound is not one of the formulae (I-a) or (I-b):

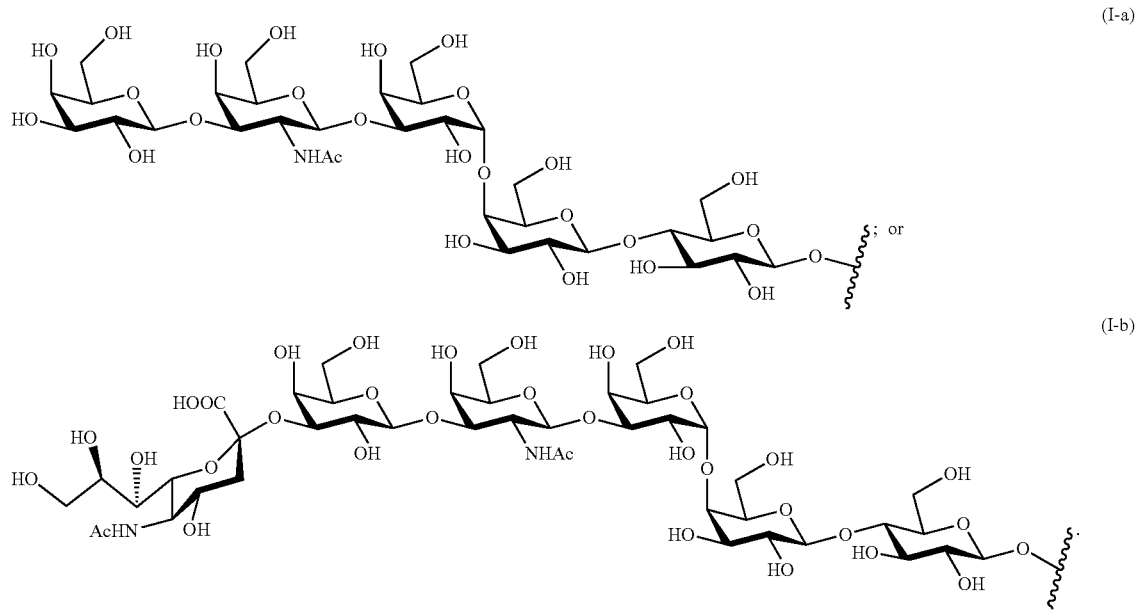

(I-a); or (I-b).

27. The compound of claim 26 wherein L is —OH.

28. The compound of claim 26 wherein L is of the formula:

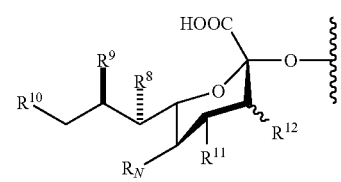

wherein:
each instance of $R^8$, $R^9$, $R^{10}$ and $R^{11}$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$; wherein $R^{12}$ is H, OH, or halogen;

$R_N$ is selected from —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$ —$SO_2R^A$, —$SO_2N(R^B)_2$, and —$NHSO_2R^B$;

each instance of $R^A$ is independently selected from hydrogen, optionally substituted alkyl, optionally substituted alkenyl, optionally substituted alkynyl, optionally substituted heterocyclyl, and optionally substituted aryl; and each instance of $R^B$ is independently selected from hydrogen, optionally substituted alkyl, optionally substituted alkenyl, optionally substituted alkynyl, optionally substituted heterocyclyl, and optionally substituted aryl.

29. The compound of claim 26 wherein the compound is of Formula (II):

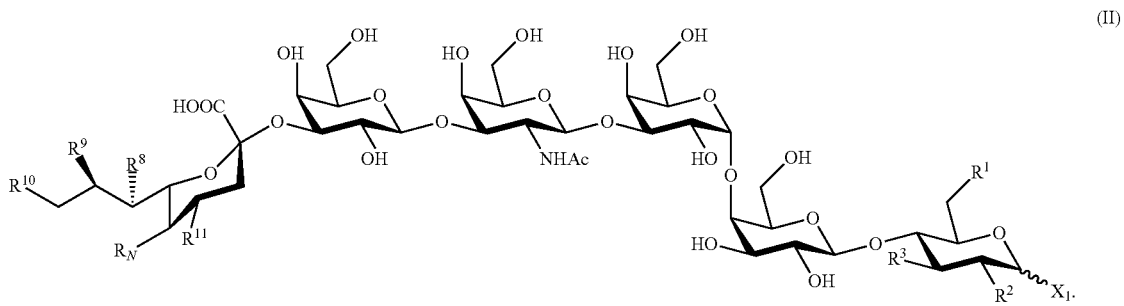

(II)

30. The compound of claim 29, wherein at least one instance of $R^1$, $R^2$, $R^3$, $R^8$, $R^9$, $R^{10}$ and $R^{11}$ is —F.

31. The compound of claim 29, wherein at least one instance of $R^1$, $R^2$, $R^3$, $R^8$, $R^9$, $R^{10}$ and $R^{11}$ is —$N_3$.

32. The method of treating hyperproliferative disease or condition comprising the administering to a subject in need thereof a therapeutically effective amount of the compound of claim 26 or 29.

33. The immunogenic composition of claim 1, wherein at least one instance of $R^1, R^2, R^3, R^4, R^5$, and $R^6$ is aryloxy.

34. The immunogenic composition of claim 33, wherein aryloxy is O-phenyl.

35. The method of claim 25, wherein at least one instance of $R^1$, $R^2$, $R^3$, $R^4$, $R^5$, $R^6$, and L is aryloxy.

36. The method of claim 35, wherein aryloxy is O-phenyl.

37. The compound of claim 26, wherein at least one instance of $R^1$, $R^2$, $R^3$, $R^4$, $R^5$, $R^6$, and L is aryloxy.

38. The compound of claim 37, wherein aryloxy is O-phenyl.

39. The immunogenic composition of any of claim 1, 2, 3 or 4, wherein the linker is a hetero- or homo-bifunctional linker; the adjuvant is selected from the group consisting of: C34, 7DW8-5, C17, C23, Gluco-C34, Aluminum salt, Squalene, MF59, and QS-21; and the carrier protein is selected from the group consisting of TT, DT and CRM197.

40. A cancer vaccine, comprising a therapeutically effective amount of the immunogenic composition of claim 39 and a pharmaceutically acceptable excipient.

41. The immunogenic composition of claim 3, wherein $R^N$ is selected from —OH, —NHC(O)C$_2$H$_4$C≡CH, —NHC(O)CH$_2$F, —NHC(O)CH$_2$Ph, —NHC(O)CH$_2$N$_3$, or —N$_3$.

42. The immunogenic composition of claim 3, wherein $R^{10}$ is selected from —OH, halogen, aryl, substituted aryl, alkynyl, substituted alkynyl, or —N$_3$.

43. The immunogenic composition of any of claim 41 or 42, wherein when $R^N$ is —OH, $R^{10}$ is —N$_3$.

* * * * *